US009096501B2

(12) United States Patent
Lawrence et al.

(10) Patent No.: US 9,096,501 B2
(45) Date of Patent: Aug. 4, 2015

(54) PLASMINOGEN ACTIVATOR INHIBITOR-1 INHIBITORS AND METHODS OF USE THEREOF TO MODULATE LIPID METABOLISM

(71) Applicant: THE REGENTS OF THE UNIVERSITY OF MICHIGAN, Ann Arbor, MI (US)

(72) Inventors: Daniel A. Lawrence, Ann Arbor, MI (US); Dudley Strickland, Brookville, MD (US); Jacqueline Cale, Minneapolis, MN (US); Enming Joe Su, Ann Arbor, MI (US); Cory Emal, Ann Arbor, MI (US); Mark Warnock, Brighton, MI (US)

(73) Assignees: THE REGENTS OF THE UNIVERSITY OF MICHIGAN, Ann Arbor, MI (US); UNIVERSITY OF MARYLAND, BALTIMORE, Baltimore, MD (US); EASTERN MICHIGAN UNIVERSITY, Ypsilanti, MI (US)

( * ) Notice: Subject to any disclaimer, the term of this patent is extended or adjusted under 35 U.S.C. 154(b) by 0 days.

(21) Appl. No.: 14/284,021

(22) Filed: May 21, 2014

(65) Prior Publication Data
US 2014/0343321 A1 Nov. 20, 2014

Related U.S. Application Data

(62) Division of application No. 12/104,409, filed on Apr. 16, 2008, now Pat. No. 8,759,327.

(60) Provisional application No. 60/912,071, filed on Apr. 16, 2007.

(51) Int. Cl.
C07C 311/29 (2006.01)
C07C 69/88 (2006.01)
C07C 271/22 (2006.01)
C07H 13/08 (2006.01)
G01N 33/92 (2006.01)

(52) U.S. Cl.
CPC ............. C07C 311/29 (2013.01); C07C 69/88 (2013.01); C07C 271/22 (2013.01); C07H 13/08 (2013.01); G01N 33/92 (2013.01); C07C 2101/14 (2013.01); G01N 2333/8132 (2013.01); G01N 2500/02 (2013.01)

(58) Field of Classification Search
CPC .... C07C 311/29; C07C 271/22; C07C 69/88; C07C 2101/14
See application file for complete search history.

(56) References Cited

U.S. PATENT DOCUMENTS

| 6,528,655 | B1 | 3/2003 | N'Zemba et al. | |
| 7,351,730 | B2 | 4/2008 | Mayer et al. | |
| 2006/0058243 | A1 | 3/2006 | Chen et al. | |
| 2009/0069302 | A1* | 3/2009 | Szewczyk et al. | ............ 514/218 |

FOREIGN PATENT DOCUMENTS

| EP | 1124157 A2 | 8/2001 |
| WO | WO-03/055843 A1 | 7/2003 |
| WO | WO-2005/000330 A2 | 1/2005 |
| WO | WO-2007/127505 A2 | 11/2007 |

OTHER PUBLICATIONS

Alessi et al., Production of plasminogen activator inhibitor 1 by human adipose tissue: possible link between visceral fat accumulation and vascular disease. *Diabetes*. 46: 860-7 (1997).
Berkenpas et al., Molecular evolution of plasminogen activator inhibitor-1 functional stability. *EMBO J.* 14: 2969-77 (1995).
Biemond, Thrombolysis and reocclusion in experimental jugular vein and coronary artery thrombosis. Effects of a plasminogen activator inhibitor type 1-neutralizing monoclonal antibody. *Circulation*. 91: 1175 (1995).
Booth, Fibrinolysis and thrombosis. *Baillieres Best. Pract. Res. Clin. Haematol.* 12: 423-33 (1999).
Boucher et al., LRP: role in vascular wall integrity and protection from atherosclerosis. *Science*. 300: 329-32 (2003).
Bu, Receptor-associated protein: a specialized chaperone and antagonist for members of the LDL receptor gene family. *Curr. Opin. Lipidol.* 9: 149-55 (1998).
Butenas et al., Ultrasensitive fluorogenic substrates for serine proteases. *Thromb. Haemost.* 78: 1193-1201 (1997).
Cao et al., A specific role of integrin Mac-1 in accelerated macrophage efflux to the lymphatics. *Blood*. 106: 3234-41 (2005).
Cao et al., Endocytic receptor LRP together with tPA and PAI-1 coordinates Mac-1-dependent macrophage migration. *EMBO J.* 25: 1860-70 (2006).
Chmielewska et al., Evidence for a rapid inhibitor to tissue plasminogen activator in plasma. *Thromb. Res.* 31: 427-36 (1983).
Cigolini et al., Expression of plasminogen activator inhibitor-1 in human adipose tissue: a role for TNF-alpha? *Atherosclerosis*. 143: 81-90 (1999).
Clausen et al., Conditional gene targeting in macrophages and granulocytes using LysMcre mice. *Transgenic Res.* 8: 265-77 (1999).

(Continued)

Primary Examiner — Dennis Heyer
(74) Attorney, Agent, or Firm — Marshall, Gerstein & Borun LLP

(57) ABSTRACT

The invention relates to plasminogen activator-1 (PAI-1) inhibitor compounds and uses thereof in the treatment of any disease or condition associated with elevated PAI-1. The invention includes, but is not limited to, the use of such compounds to modulate lipid metabolism and treat conditions associated with elevated PAI-1, cholesterol, or lipid levels.

6 Claims, 26 Drawing Sheets

(56) References Cited

OTHER PUBLICATIONS

Colucci et al., Generation in plasma of a fast-acting inhibitor of plasminogen activator in response to endotoxin stimulation. *J. Clin. Invest.* 75: 818-24 (1985).

Crandall et al., Modulation of adipose tissue development by pharmacological inhibition of PAI-1. *Arterioscler. Thromb. Vasc. Biol.* 26: 2209-15 (2006).

Crandall et al., Release of PAI-1 by human preadipocytes and adipocytes independent of insulin and IGF-1. *Biochem. Biophys. Res. Commun.* 279: 984-8 (2000).

Crandall et al., Characterization and comparative evaluation of a structurally unique PAI-1 inhibitor exhibiting oral in-vivo efficacy. *J. Thromb. Haemost.* 2: 1422-1428 (2004).

Cuchel et al., Macrophage reverse cholesterol transport: key to the regression of atherosclerosis? *Circulation*. 113: 2548-55 (2006).

Czekay et al., Plasminogen activator inhibitor-1 detaches cells from extracellular matrices by inactivating integrins. *J. Cell. Biol.* 160: 781-91 (2003).

Daci et al., Mice lacking the plasminogen activator inhibitor 1 are protected from trabecular bone loss induced by estrogen deficiency. *J. Bone Miner. Res.* 15: 1510-6. (2000).

De et al., Plasminogen activator inhibitor-1: a common denominator in obesity, diabetes and cardiovascular disease. *Curr. Opin. Pharmacol.* 5: 149-54 (2005).

De Taeye et al., Bone marrow plasminogen activator inhibitor-1 influences the development of obesity. *J. Biol. Chem.* 281: 32796-805 (2006).

Deng et al., Is plasminogen activator inhibitor-1 the molecular switch that governs urokinase receptor-mediated cell adhesion and release? *J. Cell. Biol.* 134: 1563-71 (1996).

Durand et al., Plasminogen activator inhibitor-I and tumour growth, invasion, and metastasis. *Thromb. Haemost.* 91: 438-49 (2004).

Eck et al., Role of the macrophage very-low-density lipoprotein receptor in atherosclerotic lesion development. *Artherosclerosis*. 183: 230-7 (2005).

Ehrlich et al., Elucidation of structural requirements on plasminogen activator inhibitor 1 for binding to heparin. *J. Biol. Chem.* 267: 11606-11 (1992).

Eitzman et al., Lack of plasminogen activator inhibitor-1 effect in a transgenic mouse model of metastatic melanoma. *Blood*. 87: 4718-22 (1996).

Eitzman et al., Bleomycin-induced pulmonary fibrosis in transgenic mice that either lack or overexpress the murine plasminogen activator inhibitor-1 gene. *J. Clin. Invest.* 97: 232-7 (1996).

Elokdah et al., Tiplaxtinin, a novel, orally efficacious inhibitor of plasminogen activator inhibitor-1: design, synthesis, and preclinical characterization. *J. Med. Chem.* 47: 3491-4 (2004).

Erickson et al., Detection and partial characterization of an inhibitor of plasminogen activator in human platelets. *J. Clin. Invest.* 74: 1465-72 (1984).

Farkas et al., The recycling of apolipoprotein E in primary cultures of mouse hepatocytes. Evidence for a physiologic connection to high density lipoprotein metabolism. *J. Biol. Chem.* 278: 9412-7 (2003).

Fay et al., Platelets inhibit fibrinolysis in vitro by both plasminogen activator inhibitor-1-dependent and -independent mechanisms. *Blood*. 83: 351-6 (1994).

Fay et al., Brief report: complete deficiency of plasminogen-activator inhibitor type 1 due to a frame-shift mutation. *N. Engl. J. Med.* 327: 1729-33 (1992).

Giltay et al., Visceral fat accumulation is an important determinant of PAI-1 levels in young, nonobese men and women: modulation by cross-sex hormone administration. *Arterioscler. Thromb. Vasc. Biol.* 18: 1716-22 (1998).

Gorlatova et al., Mechanism of inactivation of plasminogen activator inhibitor-1 by a small molecule inhibitor. *J. Biol. Chem.* 282: 9288-96 (2007).

Gottschling-Zeller et al., Troglitazone reduces plasminogen activator inhibitor-1 expression and secretion in cultured human adipocytes. *Diabetologia*. 43: 377-83 (2000).

Hagglof et al., The reactive-center loop of active PAI-1 is folded close to the protein core and can be partially inserted. *J. Mol. Biol.* 335: 823-32 (2004).

Hamsten et al., Increased plasma levels of a rapid inhibitor of tissue plasminogen activator in young survivors of myocardial infarction. *N. Engl. J. Med.* 313: 1557-63 (1985).

Hasty et al., The recycling of apolipoprotein E in macrophages: influence of HDL and apolipoprotein A-I. *Lipid Res.* 46: 1433-9 (2005).

Heeren et al., Recycling of apoprotein E is associated with cholesterol efflux and high density lipoprotein internalization. *J. Biol. Chem.* 278: 14370-8 (2003).

Hekman et al., Bovine plasminogen activator inhibitor 1: specificity determinations and comparison of the active, latent, and guanidine-activated forms. *Biochemistry*. 27: 2911-8 (1988).

Hekman et al., Endothelial cells produce a latent inhibitor of plasminogen activators that can be activated by denaturants. *J. Biol. Chem.* 260: 11581-7 (1985).

Hennan et al., Evaluation of PAI-039 [{1-benzyl-5-[4-(trifluoromethoxy)phenyl]-1H-indol-3-yl}(oxo)acetic acid], a novel plasminogen activator inhibitor-1 inhibitor, in a canine model of coronary artery thrombosis. *J. Pharmacol. Exp. Ther.* 314: 710-6 (2005).

Herz et al., LDL receptor-related protein internalizes and degrades uPA-PAI-1 complexes and is essential for embryo implantation. *Cell*. 71: 411-21 (1992).

Horn et al., Plasminogen activator inhibitor 1 contains a cryptic high affinity receptor binding site that is exposed upon complex formation with tissue-type plasminogen activator. *Thromb. Haemost.* 80: 822-8 (1998).

Huber et al., Implications of the three-dimensional structure of alpha 1-antitrypsin for structure and function of serpins. *Biochemistry*. 28: 8951-66 (1989).

Huber et al., Plasminogen activator inhibitor type-1 (part one): basic mechanisms, regulation, and role for thromboembolic disease. *J. Thromb. Thrombolysis*. 11: 183-93 (2001).

Huntington et al., Structure of a serpin-protease complex shows inhibition by deformation. *Nature*. 407: 923-6 (2000).

Huntington et al., The serpins: nature's molecular mousetraps. *Sci. Prog.* 84: 125-36 (2001).

Hussain et al., The mammalian low-density lipoprotein receptor family. *Annu. Rev. Nutr.* 19: 141-72 (1999).

Jensen et al., The vitronectin binding area of plasminogen activator inhibitor-1, mapped by mutagenesis and protection against an inactivating organochemical ligand. *FEBS Lett.* 521: 91-4 (2002).

Kannel, Overview of hemostatic factors involved in atherosclerotic cardiovascular disease. *Lipids*. 40: 1215-20 (2005).

Kazi et al., Structure-activity relationships of synthetic analogs of (−)-epigallocatehin-3-gallate as proteasome inhibitors, *Anticancer Research*. 24: 943-54 (2004).

Keijer et al., On the target specificity of plasminogen activator inhibitor 1: the role of heparin, vitronectin, and the reactive site. *Blood*. 78: 1254-61 (1991).

Kockx et al., Apolipoprotein A-I-stimulated apolipoprotein E secretion from human macrophages is independent of cholesterol efflux. *J. Biol. Chem.* 279: 25966-77 (2004).

Kohler et al., Plasminogen-activator inhibitor type 1 and coronary artery disease. *N. Engl. J. Med.* 342: 1792-1801 (2000).

Krieger et al., Scavenger receptor class B type I is a multiligand HDL receptor that influences diverse physiologic systems. *J. Clin. Invest.* 108: 793-7 (2001).

Krishnamurti et al., Plasminogen activator inhibitor: a regulator of ancrod-induced fibrin deposition in rabbits. et al., *Blood*. 69: 798 (1987).

Lambers et al., Activation of human endothelial cell-type plasminogen activator inhibitor (PAI-1) by negatively charged phospholipids. *J. Biol. Chem.* 262: 17492-6 (1987).

Lawrence et al., Inactivation of plasminogen activator inhibitor by oxidants. *Biochemistry*. 25: 6351-5 (1986).

Lawrence et al., Engineering plasminogen activator inhibitor 1 mutants with increased functional stability. *Biochemistry*. 33: 3643-8 (1994).

(56) References Cited

OTHER PUBLICATIONS

Lawrence et al., Purification of active human plasminogen activator inhibitor 1 from *Escherichia coli*. Comparison with natural and recombinant forms purified from eucaryotic cells. *Eur. J. Biochem.* 186: 523-33 (1989).

Lawrence et al., Structure-function studies of the SERPIN plasminogen activator inhibitor type 1. Analysis of chimeric strained loop mutants. *J. Biol. Chem.* 265: 20293-301 (1990).

Lawrence et al., Localization of vitronectin binding domain in plasminogen activator inhibitor-1. *J. Biol. Chem.* 269: 15223-8 (1994).

Lawrence et al., Serpin reactive center loop mobility is required for inhibitor function but not for enzyme recognition. *J. Biol. Chem.* 269: 27657-62 (1994).

Lawrence et al., Serpin-protease complexes are trapped as stable acyl-enzyme intermediates. *J. Biol. Chem.* 270: 25309-12 (1995).

Lawrence et al., Characterization of the binding of different conformational forms of plasminogen activator inhibitor-1 to vitronectin. Implications for the regulation of pericellular proteolysis. *J. Biol. Chem.* 272: 7676-80 (1997).

Lawrence et al., Partitioning of serpin-proteinase reactions between stable inhibition and substrate cleavage is regulated by the rate of serpin reactive center loop insertion into beta-sheet A. *J. Biol. Chem.* 275: 5839-44 (2000).

Lawrence et al., Molecular Basis of Thrombosis and Hemostasis, Marcel Dekker Inc., New York, 517-43 (1995).

Le Lay et al., Regulation of ABCA1 expression and cholesterol efflux during adipose differentiation of 3T3-L1 cells. *J. Lipid Res.* 44: 1499-1507 (2003).

Levi, Inhibition of plasminogen activator inhibitor-1 activity results in promotion of endogenous thrombolysis and inhibition of thrombus extension in models of experimental thrombosis. *Circulation.* 85: 305-12 (1992).

Levin et al., Conversion of the active to latent plasminogen activator inhibitor from human endothelial cells. *Blood.* 70: 1090-8 (1987).

Liang et al., Plasminogen activator inhibitor-1 modulates adipocyte differentiation. *Am. J. Physiol. Endocrinol. Metab.* 290: E103-13 (2006).

Lijnen et al., On the role of plasminogen activator inhibitor-1 in adipose tissue development and insulin resistance in mice. *J. Thromb. Haemost.* 3: 1174-9 (2005).

Lindahl et al., Stability of plasminogen activator inhibitor 1 (PAI-1). *Thromb. Haemost.* 62: 748-51 (1989).

Liu et al., Highly purified scavenger receptor class B, type I reconstituted into phosphatidylcholine/cholesterol liposomes mediates high affinity high density lipoprotein binding and selective lipid uptake. *J. Biol. Chem.* 277: 34125-35 (2002).

Loskutoff et al., The adipocyte and hemostatic balance in obesity: studies of PAI-1. *Arterioscler. Thromb. Vasc. Biol.* 18:1-6 (1998).

Loskutoff et al., Detection of an unusually stable fibrinolytic inhibitor produced by bovine endothelial cells. *Proc. Natl. Acad. Sci. USA.* 80: 2956-60 (1983).

Lundgren et al., Elaboration of type-1 plasminogen activator inhibitor from adipocytes. A potential pathogenetic link between obesity and cardiovascular disease. *Circulation.* 93: 106-10 (1996).

Lupu et al., Localization and production of plasminogen activator inhibitor-1 in human healthy and atherosclerotic arteries. *Arterioscler. Thromb.* 13: 1090-1100 (1993).

Ma et al., Prevention of obesity and insulin resistance in mice lacking plasminogen activator inhibitor 1. *Diabetes.* 53: 336-46 (2004).

Mavri et al., Impact of adipose tissue on plasma plasminogen activator inhibitor-1 in dieting obese women. *Arterioscler. Thromb. Vasc. Biol.* 19: 1582-7 (1999).

Minor et al., Plasminogen activator inhibitor type 1 promotes the self-association of vitronectin into complexes exhibiting altered incorporation into the extracellular matrix. *J. Biol. Chem.* 277: 10337-45 (2002).

Morange et al., Glucocorticoids and insulin promote plasminogen activator inhibitor 1 production by human adipose tissue. *Diabetes.* 48: 890-5 (1999).

Mottonen et al., Structural basis of latency in plasminogen activator inhibitor-1. *Nature.* 355: 270-3 (1992).

Naski et al., Kinetics of inactivation of alpha-thrombin by plasminogen activator inhibitor-1. Comparison of the effects of native and urea-treated forms of vitronectin. *J. Biol. Chem.* 268: 12367-72 (1993).

Nordt, Differential regulation by troglitazone of plasminogen activator inhibitor type 1 in human hepatic and vascular cells. *J. Clin. Endocrin. Metabol.* 85: 1563-8 (2000).

Ny et al., Cloning and sequence of a cDNA coding for the human beta-migrating endothelialcell-type plasminogen activator inhibitor. *Proc. Natl. Acad. Sci. USA.* 83: 6776-80 (1986).

Ohashi et al., Reverse cholesterol transport and cholesterol efflux in atherosclerosis. *QJM.* 98: 845-56 (2005).

Podor et al., Type 1 plasminogen activator inhibitor binds to fibrin via vitronectin. *J. Biol. Chem.* 275: 19788-94 (2000).

Podor et al., New insights into the size and stoichiometry of the plasminogen activator inhibitor type-1.vitronectin complex. *J. Biol. Chem.* 275: 25402-10 (2000).

Podor et al., Incorporation of vitronectin into fibrin clots. Evidence for a binding interaction between vitronectin and gamma A/gamma' fibrinogen. *J. Biol. Chem.* 277: 7520-8 (2002).

Reilly, Both circulating and clot-bound plasminogen activator inhibitor-1 inhibit endogenous fibrinolysis in the rat. *Arterioscler. and Thromb.*. 11: 1276 (1991).

Renckens et al., The role of plasminogen activator inhibitor type 1 in the inflammatory response to local tissue injury. *J. Thromb. Haemost.* 3: 1018-25 (2005).

Robbie et al., Inhibitors of fibrinolysis are elevated in atherosclerotic plaque. *Arterioscler. Thromb. Vasc. Biol.* 16: 539-45 (1996).

Rohlmann et al., Inducible inactivation of hepatic LRP gene by cre-mediated recombination confirms role of LRP in clearance of chylomicron remnants. *J. Clin. Invest.* 101: 689-95 (1998).

Ross et al., Atherosclerosis—an inflammatory disease. *N. Engl. J. Med.* 340: 115-26 (1999).

Ruiz et al., The apoE isoform binding properties of the VLDL receptor reveal marked differences from LRP and the LDL receptor. *J. Lipid Res.* 46: 1721-31 (2005).

Sakamoto et al., TNF-alpha and insulin, alone and synergistically, induce plasminogen activator inhibitor-1 expression in adipocytes. *Am. J. Physiol.* 276: C1391-7 (1999).

Samad et al., Distribution and regulation of plasminogen activator inhibitor-1 in murine adipose tissue in vivo. Induction by tumor necrosis factor-alpha and lipopolysaccharide. *J. Clin. Invest.* 97: 37-46 (1996).

Samad et al., Tissue distribution and regulation of plasminogen activator inhibitor-1 in obese mice. *Mol. Med.* 2: 568-82 (1996).

Sawicki et al., A composite CMV-IE enhancer/beta-actin promoter is ubiquitously expressed in mouse cutaneous epithelium. *Exp. Cell Res.* 244: 367-9 (1998).

Schafer et al., Disruption of the plasminogen activator inhibitor 1 gene reduces the adiposity and improves the metabolic profile of genetically obese and diabetic ob/ob mice. *FASEB J.* 15: 1840-2 (2001).

Schneiderman et al., Increased type 1 plasminogen activator inhibitor gene expression in atherosclerotic human arteries. *Proc. Natl. Acad. Sci. USA.* 89: 6998-7002 (1992).

Seiffert et al., Constitutive and regulated expression of vitronectin. *Histol. Histopathol.* 12: 787-97 (1997).

Seiffert et al., The cell adhesion domain in plasma vitronectin is cryptic. *J. Biol. Chem.* 272: 13705-10 (1997).

Sharp et al., The active conformation of plasminogen activator inhibitor 1, a target for drugs to control fibrinolysis and cell adhesion. *Structure.* 7: 111-8 (1999).

Sherman et al., Saturation mutagenesis of the plasminogen activator inhibitor-1 reactive center. *J. Biol. Chem.* 267: 7588-95 (1992).

Shimomura et al., Enhanced expression of PAI-1 in visceral fat: possible contributor to vascular disease in obesity. *Nat. Med.* 2: 800-803 (1996).

Smith et al., Pivotal role of PAI-1 in a murine model of hepatic vein thrombosis. *Blood.* 107: 132-4 (2006).

Sprengers et al., Plasminogen activator inhibitors. *Blood.* 69: 381-7 (1987).

(56) References Cited

OTHER PUBLICATIONS

Stefansson et al., Plasminogen activator inhibitor-1 in tumor growth, angiogenesis and vascular remodeling. *Curr. Pharm. Des.* 9: 1545-64 (2003).
Stefansson et al., Plasminogen activator inhibitor-1 and vitronectin promote the cellular clearance of thrombin by low density lipoprotein receptor-related proteins 1 and 2. *J. Biol. Chem.* 271: 8215-20 (1996).
Stefansson et al., Plasminogen activator inhibitor-1 contains a cryptic high affinity binding site for the low density lipoprotein receptor-related protein. *J. Biol. Chem.* 273: 6358-66 (1998).
Stefansson et al., Inhibition of angiogenesis in vivo by plasminogen activator inhibitor-1. *J. Biol. Chem.* 276: 8135-41 (2001).
Stefansson et al., Mutants of plasminogen activator inhibitor-1 designed to inhibit neutrophil elastase and cathepsin G are more effective in vivo than their endogenous inhibitors. *J. Biol. Chem.* 279: 29981-7 (2004).
Stefansson et al., The serpin PAI-1 inhibits cell migration by blocking integrin alpha V beta 3 binding to vitronectin. *Nature.* 383: 441-3 (1996).
Stefansson et al., Old dogs and new tricks: proteases, inhibitors, and cell migration. *Sci. STKE.* 2003: pe24 (2003).
Stewart et al., Synthesis of 3-nitro-L-tyrosine peptides by means of active polyester intermediates derived from the nitrophenol side chain. *Australian J. Chem.* 3293:661-7 (1979).
Strandberg et al., The oxidative inactivation of plasminogen activator inhibitor type 1 results from a conformational change in the molecule and does not require the involvement of the P1' methionine. *J. Biol. Chem.* 266: 13852-8 (1991).
Suganami et al., A paracrine loop between adipocytes and macrophages aggravates inflammatory changes: role of free fatty acids and tumor necrosis factor alpha. *Arterioscler. Thromb. Vasc. Biol.* 25: 2062-8 (2005).
Takahashi et al., Purification and ATPase activity of human ABCA1. *J. Biol. Chem.* 281: 10760-8 (2006).
Takahashi et al., The very low density lipoprotein (VLDL) receptor—a peripheral lipoprotein receptor for remnant lipoproteins into fatty acid active tissues. *Mol. Cell. Biochem.* 248: 121-7 (2003).
Tomasini et al., Vitronectin. *Prog. Hemost. Thromb.* 10: 269-305 (1991).
Vague et al., Correlation between blood fibrinolytic activity, plasminogen activator inhibitor level, plasma insulin level, and relative body weight in normal and obese subjects. *Metabolism.* 35: 250-3 (1986).
van Mourik et al., Purification of an inhibitor of plasminogen activator (antiactivator) synthesized by endothelial cells. *J. Biol. Chem.* 259: 14914-21 (1984).
Vassiliou et al., A novel efflux-recapture process underlies the mechanism of high-density lipoprotein cholesteryl ester-selective uptake mediated by the low-density lipoprotein receptor-related protein. *Arterioscler. Thromb. Vasc. Biol.* 24: 1669-75 (2004).
Vaughan et al., Studies of recombinant plasminogen activator inhibitor-1 in rabbits. Pharmacokinetics and evidence for reactivation of latent plasminogen activator inhibitor-1 in vivo. *Circ. Res.* 67: 1281-6 (1990).
Vaughan, PAI-1 and atherothrombosis. *J. Thromb. Haemost.* 3: 1879-83 (2005).
Vezina et al., Apolipoprotein distribution in human lipoproteins separated by polyacrylamide gradient gel electrophoresis. *J. Lipid Res.* 29: 573-85 (1988).

Webb et al., Plasminogen activator inhibitor 1 functions as a urokinase response modifier at the level of cell signaling and thereby promotes MCF-7 cell growth. *J. Cell. Biol.* 152: 741-52 (2001).
Weisberg et al., Pharmacological inhibition and genetic deficiency of plasminogen activator inhibitor-1 attenuates angiotensin II/salt-induced aortic remodeling. *Arterioscler. Thromb. Vasc. Biol.* 25: 365-71 (2005).
Weiss et al., Neutrophils degrade subendothelial matrices in the presence of alpha-1-proteinase inhibitor. Cooperative use of lysosomal proteinases and oxygen metabolites. *J. Clin. Invest.* 73: 1297-1303 (1984).
Wilczynska et al., The inhibition mechanism of serpins. Evidence that the mobile reactive center loop is cleaved in the native protease-inhibitor complex. *J. Biol. Chem.* 270: 29652-5 (1995).
Xu et al., Conservation of critical functional domains in murine plasminogen activator inhibitor-1. *J. Biol. Chem.* 279: 17914-20 (2004).
Xu et al., Apolipoproteins of HDL can directly mediate binding to the scavenger receptor SR-BI, an HDL receptor that mediates selective lipid uptake. *J. Lipid Res.* 38: 1289-98 (1997).
Yepes et al., Plasminogen Activator Inhibitor-1, Hemostasis and Thrombosis: Basic Principles and Clinical Practice, Lippincott Williams & Wilkins, 365-80 (2006).
Zannis et al., Role of apoA-I, ABCA1, LCAT, and SR-BI in the biogenesis of HDL. *J. Mol. Med.* 84: 276-94 (2006).
Zhou et al., How vitronectin binds PAI-1 to modulate fibrinolysis and cell migration. *Nat. Struct. Biol.* 10: 541-4 (2003).
Boncoraglio et al., An effect of the PAI-1 4G/5G polymorphism on cholesterol levels may explain conflicting associatations with myocardial infarction and stroke. *Cerebrovascular Dis.* 22(2-3): 191-5 (2006).
Chen et al., 4G/5G promoter polymorphism of plasminogen activator inhibitor-1, lipid profiles, and ischemic stroke. *J. Lab. Clin. Med.* 142(2): 100-5 (2003).
Dichtl et al., In vivo stimulation by vascular plasminogen activator inhibitor-1 production by very low-density lipoprotein involves transcription factor binding to a VLDL-responsive element. *Thrombosis Haemastasis*, 84(4): 706-11 (2000).
Gaitatzis et al., Novel insights into siderophore formation in myxobacteria. *ChemBioChem*, 6:365-74 (2005).
International Preliminary Report on Patentability, PCT/US2008/60542, dated Oct. 20, 2009.
International Search Report and Written Opinion of the International Searching Authority, European Patent Office, PCT/US2008/60542, dated Nov. 21, 2008.
Jensen et al., Inhibition of plasminogen activator inhibitor-1 binding to endocytosis receptors of the low-density-lipoprotein receptor family by a peptide isolated from a phage display library. *Biochem. J.* 399(3): 387-96 (2006).
Lopes et al., PAI-1 polymorphisms modulate phenotypes associated with the metabolic syndrome in obese and diabetic Caucasian population. *Diabetologia.* 46(9): 1284-90 (2003).
Nilsson et al., VLDL activation of plasminogen activator inhibitor-1 (PAI-1) expression: Involvement of the VLDL receptor. *J. Lipid Res.* 40(5): 913-9 (1999).
Rodenburg et al., Binding of urokinase-type plasminogen activator-plasminogen activator inhibitor-1 complex to the endocytosis receptors alpha2-macroglobulin receptor/low-density lipoprotein receptor-related protein and very-low-density lipoprotein receptor involved basic residues in the inhibitor. *Biochem. J.* 329(Part 1): 55-63 (1998).

\* cited by examiner

FIGURE 1A

| Name | Formula | IC$_{50}$ pH 7.5 (µM) | IC$_{50}$ pH 8.5 (µM) | Structure |
|---|---|---|---|---|
| Hexachlorophene | $C_{13}H_6Cl_6O_2$ | 3.23±0.373 | 4.53±0.170 | 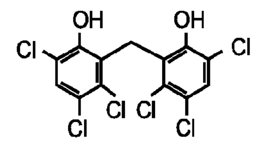 |
| Tannic Acid | $C_{76}H_{52}O_{46}$ | 7.15±0.39 | 0.0091±0.0015 | 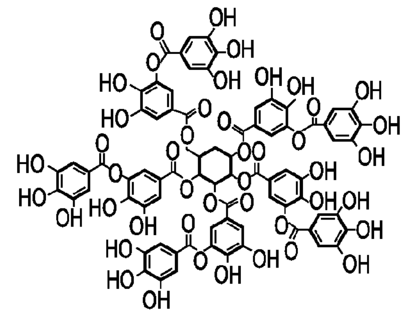 |
| Quinalizarin | $C_{14}H_8O_6$ | 18.1±0.7 | | 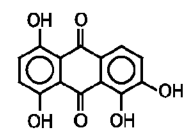 |
| Epigallocatechin 3,5 - Digallate | | 57.9±8.7 | | 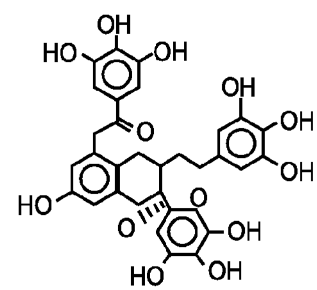 |

FIGURE 1B

| Name | Formula | IC$_{50}$ pH 7.5 (μM) | IC$_{50}$ pH 8.5 (μM) | Structure |
|---|---|---|---|---|
| (−)-Epigallocatechin Gallate | C$_{22}$H$_{18}$O$_{11}$ | 315.4±115.97 | 0.113±.029 | 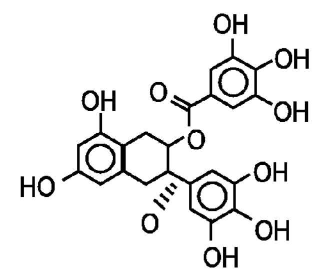 |
| 5-Nitrosalicylic Acid | C$_7$H$_5$NO$_5$ | 654.1±48.1 | | 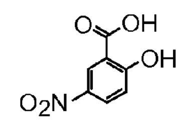 |
| Chlorogenic Acid | C$_{16}$H$_{18}$O$_9$, | 812±21 | 423.8±22.5 | 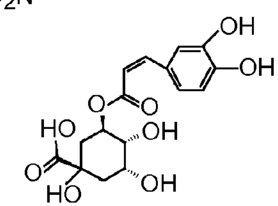 |
| Caffeic Acid | C$_9$H$_8$O$_4$ | 1720±250 | 1195±770 | 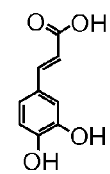 |

| Name | Formula | IC$_{50}$ pH 7.5 (μM) | IC$_{50}$ pH 8.5 (μM) | Structure |
|---|---|---|---|---|
| 3-Nitro-L-Tyrosine | C$_9$H$_{10}$N$_2$O$_5$ | 2912.49±438.30 | | 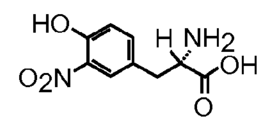 |
| 3-Chloro-L-Tyrosine | C$_9$H$_{10}$ClNO$_3$ | 4823.6±934.3 | | 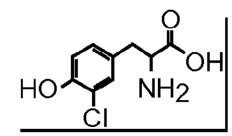 |
| Gallic Acid | C$_7$H$_6$O$_5$ | 8115±1857 | 225.2±238.8 | 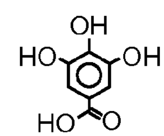 |
| 5-Chlorosalicylic Acid | C$_7$H$_5$ClO$_3$ | 10700±1100 | | 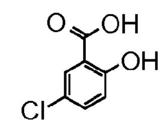 |
| Polyphenon-60 | | 215.53±26.27 μg/mL | 0.0004±0.0016 μg/mL | |

Tannic Acid

EGCG

Gallic Acid

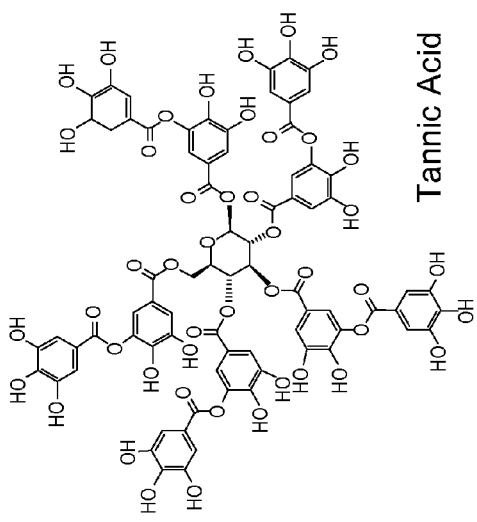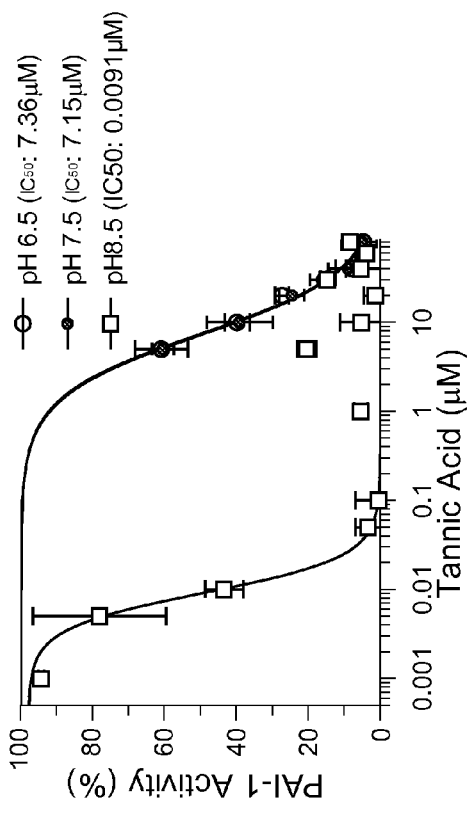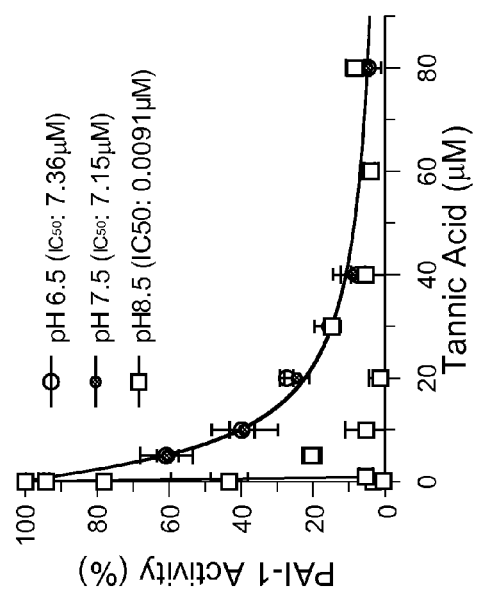
FIGURE 4A
FIGURE 4B
FIGURE 4C

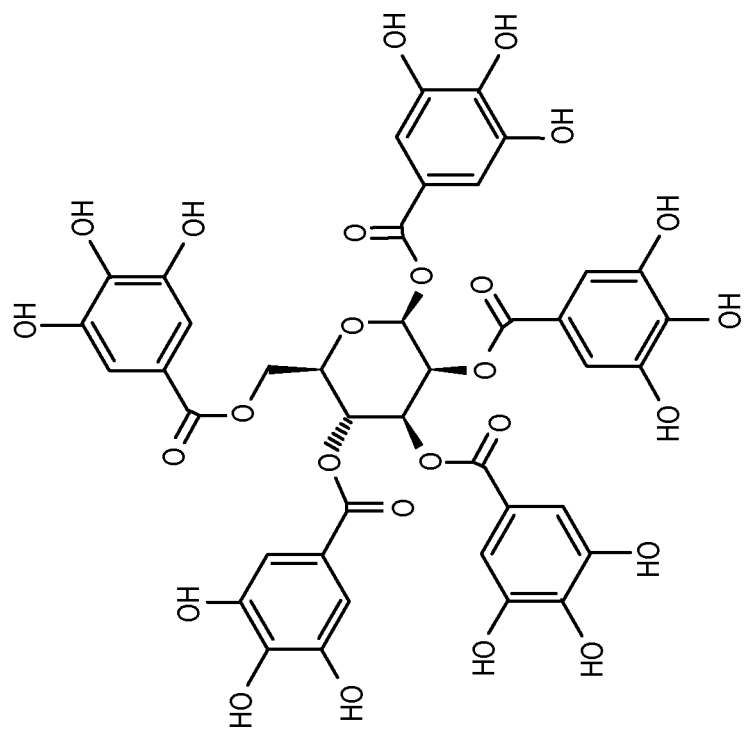
FIGURE 8B CDE-002 β-mannose
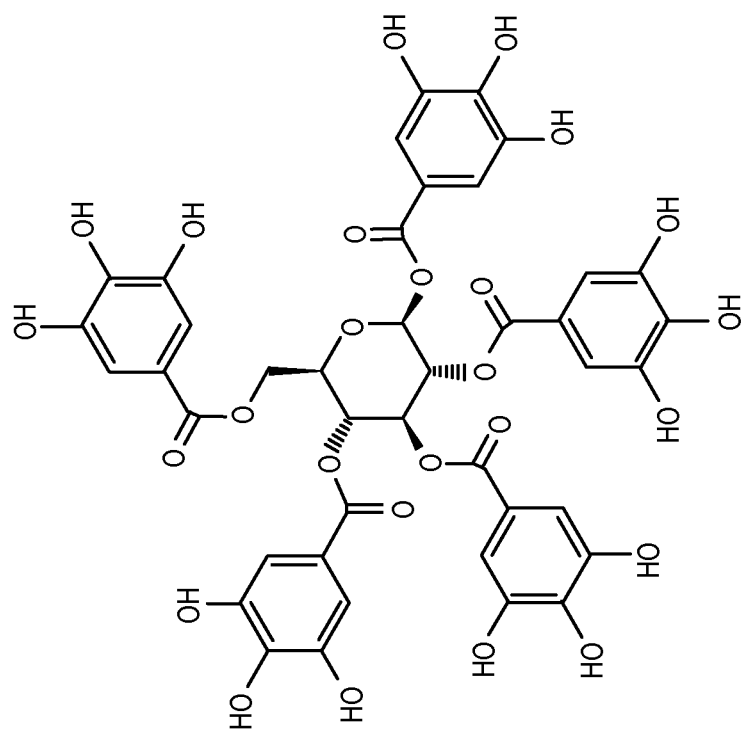
FIGURE 8A CDE-001 α/β-glucose

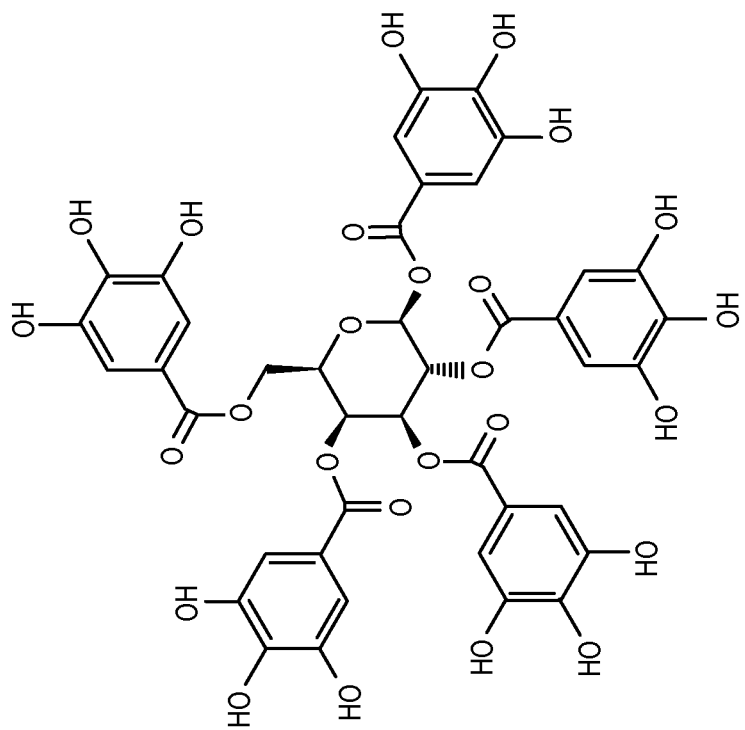
FIGURE 8D CDE-004 β-galactose
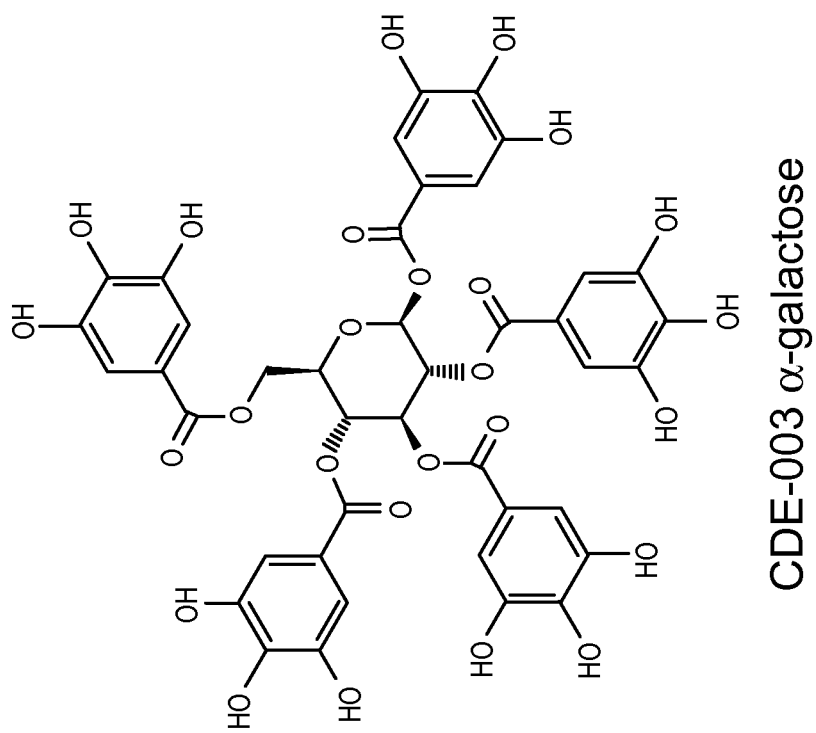
FIGURE 8C CDE-003 α-galactose CDE-007 α-galactose
Not inhibitory CDE-006 β-galactose
Not inhibitory

CDE-009
$C_{18}H_{18}O_{11}$

Exact Mass: 410.0849
Mol. Wt.: 410.3289
digalloyl diethylene glycol

CDE-011
$C_{22}H_{26}O_{13}$

Exact Mass: 498.1373
Mol. Wt.: 498.4340
digalloyl tetraethylene glycol

CDE-010)
possible Pd/C impurity

CDE-12
(repurified CDE-010)
possible Pd/C impurity $C_{20}H_{22}O_{12}$
Exact Mass: 454.1111
Mol. Wt.: 454.3815
digalloyl triethylene glycol CDE-013
$C_{17}H_{16}O_{10}$
Exact Mass: 380.0743
Mol. Wt.: 380.3029

PLASMINOGEN ACTIVATOR INHIBITOR-1 INHIBITORS AND METHODS OF USE THEREOF TO MODULATE LIPID METABOLISM

CROSS REFERENCE TO RELATED APPLICATIONS

This application is a divisional application of U.S. patent application Ser. No. 12/104,409 filed Apr. 16, 2008, which claims the benefit of U.S. Provisional Application No. 60/912,071 filed Apr. 16, 2007, the entire respective disclosures of which are incorporated herein by reference.

GOVERNMENT RIGHTS

This invention was made in part with government support under grant numbers HL055374 and HL054710 from the National Institute of Health. As such, the United States government has certain rights in the invention.

FIELD OF THE INVENTION

The invention generally relates to methods and compositions for modulating lipid metabolism. More particularly, the invention is directed to methods of identifying inhibitors of plasminogen activator inhibitor-1 (PAI-1) and the uses of such inhibitors in regulating lipid metabolism. The invention also relates to uses of these inhibitors for the treatment of many conditions, diseases or disorders associated with PAI-1 activity. Such conditions or disorders include, but are not limited to, inflammation, cell migration and migration-driven proliferation of cells, and angiogenesis or thrombosis. Such inhibitors are also contemplated to be useful for modulation of endogenous fibrinolysis, and in conjunction with pharmacologic thrombolysis.

BACKGROUND OF THE INVENTION

Plasminogen activator inhibitor-1 (PAI-1) is a 50 kDa single-chain glycoprotein (Loskutoff et al., Proc. Natl. Acad. Sci. USA 80:2956-2960, 1983; Chmielewska et al., Thromb. Res. 31:427-436, 1983) that is the principal inhibitor of both urokinase type plasminogen activator (uPA) and tissue type PA (tPA) (Fay et al., N. Engl. J. Med. 327:1729-1733, 1992; Fay et al., Blood 83:351-356, 1994; Yepes et al., "Plasminogen Activator Inhibitor-1," In Hemostasis and Thrombosis: Basic Principles and Clinical Practice, Robert W Colman et al., editors Lippincott Williams & Wilkins, pp. 365-380, 2006). PAI-1 inhibits tPA and uPA with second-order rate constants $\sim 10^7 \, M^{-1}s^{-1}$, a value that is 10-1000 times faster than the rates of PA inhibition by other PAIs (Sprengers et al., Blood 69:381-387, 1987; Lawrence et al., J. Biol. Chem. 265:20293-20301, 1990; Lawrence et al., In Molecular Basis of Thrombosis and Hemostasis. K. A. High, and Roberts, H. R., editors. Marcel Dekker, Inc. New York. 517-543, 1995). Moreover, approximately 70% of the total tPA in carefully collected normal human plasma is detected in complex with PAI-1, suggesting that inhibition of tPA by PAI-1 is a normal, ongoing process. PAI-1 can also directly inhibit plasmin (Hekman et al., Biochem. 27:2911-2918, 1988; Stefansson et al., J. Biol. Chem. 276:8135-8141, 2001). Thus, PAI-1 is the chief regulator of plasmin generation in vivo, and as such it appears to play an important role in both fibrinolytic and thrombotic disease (Booth, Baillieres Best. Pract. Res. Clin. Haematol. 12:423-433, 1999; Huber, J. Thromb. Thrombolysis. 11:183-193, 2001; Kohler et al., N. Engl. J. Med. 342: 1792-1801, 2000; Stefansson et al., Current Pharmaceutical Design 9:1545-1564, 2003). PAI-1 has three potential N-linked glycosylation sites and contains between 15 and 20% carbohydrate (Ny et al., Proc. Natl. Acad. Sci. USA 83:6776-6780, 1986; van Mourik et al., J. Biol. Chem. 259: 14914-14921, 1984).

PAI-1 belongs to the Serine Protease Inhibitor super family (SERPIN), which is a gene family that includes many of the protease inhibitors found in blood, as well as other proteins with unrelated or unknown functions (Gettins et al., Serpins: Structure, Function and Biology. R.G. Landes Company. Austin, Tex. U.S.A, 1996). Serpins are consumed in the process of protease inactivation and thus act as "suicide inhibitors" (Lawrence et al., J. Biol. Chem. 270:25309-25312, 1995). The association between a serpin and its target protease occurs at an amino acid residue, referred to as the "bait" residue, located on a surface loop of the serpin called the reactive center loop (RCL) (Huber et al., Biochem. 28:8951-8966, 1989; Sherman et al., J. Biol. Chem. 267:7588-7595, 1992). The "bait" residue is also called the P1 residue, and is thought to mimic the normal substrate of the enzyme. Upon association of the P1 residue with the Si site of a target protease, cleavage of the RCL occurs. This is coupled to a large conformational change in the serpin which involves rapid insertion of the RCL into the major structural feature of a serpin, β-sheet A (Lawrence et al., J. Biol. Chem. 270: 25309-25312, 1995; Lawrence et al., J. Biol. Chem. 270: 25309-25312, 1995; Wilczynska et al., J. Biol. Chem. 270: 29652-29655, 1995; Lawrence et al., J Biol. Chem. 275: 5839-5844, 2000; Hagglof et al., J. Mol. Biol. 335:823-832, 2004). This results in tight docking of the protease to the serpin surface and to distortion of the enzyme structure, including its active site. RCL insertion also produces a large increase in serpin structural stability making the complex rigid and thus trapping the protease in a covalent acyl-enzyme complex with the serpin (Lawrence et al., J. Biol. Chem. 265:20293-20301, 1990; Huntington et al., Nature 407:923-926, 2000; Huntington et al., Sci. Prog. 84:125-136, 2001).

Native PAI-1 exists in at least two distinct conformations, an active form that is produced by cells and secreted, and an inactive or latent form that accumulates in cell culture medium over time (Hekman et al., J. Biol. Chem. 260:11581-11587, 1985; Mottonen et al., Nature 355:270-273, 1992). In blood and tissues, most of the PAI-1 is in the active form; however, in platelets both active and latent forms of PAI-1 are found (Erickson et al., J. Clin. Invest. 74:1465-1472, 1984). In active PAI-1, the RCL is exposed on the surface of the molecule (Sharp et al., Structure Fold. Des. 7:111-118, 1999), but upon reaction with a protease, the cleaved RCL integrates into the center of β sheet A (Lawrence et al., J Biol. Chem. 270: 25309-25312, 1995; Sharp et al., supra). In the latent form, the RCL is intact, but instead of being exposed, the entire amino terminal side of the RCL is inserted as the central strand into the β sheet A (Mottonen et al., supra). This accounts for the increased stability of latent PAI-1 as well as its lack of inhibitory activity (Hekman et al., supra; Lawrence et al., Biochem. 33: 3643-3648, 1994; Lawrence et al., J. Biol. Chem. 269: 27657-27662, 1994).

Active PAI-1 spontaneously converts to the latent form with a half-life of one to two hours at 37° C. (Hekman et al., Biochem. 27:2911-2918, 1988; Lawrence et al., Eur. J. Biochem. 186:523-533, 1989; Levin et al., Blood 70:1090-1098, 1987; Lindahl et al., Thromb. Haemost. 62:748-751, 1989), and latent PAI-1 can be converted back into the active form by treatment with denaturants (Hekman et al., J. Biol. Chem. 260:11581-11587, 1985). Negatively charged phospholipids can also convert latent PAI-1 to the active form, suggesting that cell surfaces may modulate PAI-1 activity (Lambers et al., J. Biol. Chem. 262:17492-17496, 1987). The observation that latent PAI-1 infused into rabbits is apparently converted to the active form is consistent with this hypothesis (Vaughan et al., Circ. Res. 67:1281-1286, 1990). The spontaneous reversible interconversion between the active and latent structures is unique for PAI-1 and distinguishes it from other serpins; however, the biological significance of the latent conformation remains unknown.

Other non-inhibitory forms of PAI-1 have also been identified. The first form results from oxidation of one or more critical methionine residues within active PAI-1 (Lawrence et al., Biochem. 25:6351-6355, 1986; Strandberg et al., J. Biol. Chem. 266:13852-13858, 1991). This form differs from latent PAI-1 in that it can be partially reactivated by an enzyme that specifically reduces oxidized methionine residues (Lawrence et al., Biochem. 25:6351-6355, 1986). Oxidative inactivation of PAI-1 may be an additional mechanism for the regulation of PAI-1, and oxygen radicals produced locally by neutrophils or other cells may inactivate PAI-1 and thus facilitate the generation of plasmin at sites of infection or in areas of tissue remodeling (Weiss et al., J. Clin. Invest. 73:1297-1303, 1984). PAI-1 also exists in two different cleaved forms. As noted above, PAI-1 complexed with a protease is cleaved in its RCL. Uncomplexed PAI-1 can also be found with its RCL cleaved, which can arise from dissociation of PAI-1-PA complexes or from cleavage of the RCL by a non-target protease at a site other than the P1 (Lawrence et al., J Biol. Chem. 270:25309-25312, 1995; Lawrence et al., J. Biol. Chem. 269:27657-27662, 1994; Wu et al, Blood 86:1056-1061, 1995). None of these forms of PAI-1 are able to inhibit protease activity; however, they may interact with other ligands.

The interaction of PAI-1 with non-protease ligands plays an essential role in PAI-1 function (Yepes et al., supra). PAI-1 binds with high affinity to heparin, the cell adhesion protein vitronectin, and members the endocytic low-density lipoprotein receptor (LDL-R) family, such as the lipoprotein receptor-related protein (LRP), and the very low density lipoprotein receptor (VLDL-R) (Lawrence et al., J Biol. Chem. 269: 15223-15228, 1994; Stefansson et al., J Biol. Chem. 273: 6358-6366, 1998; Horn et al., Thromb. Haemost. 80:822-828, 1998; Hussain et al., Annu. Rev. Nutr. 19:141-172, 1999; Jensen et al., FEBS Lett. 521:91-94, 2002; Zhou et al., Nat. Struct. Biol. 10:541-544, 2003; Xu et al., J. Biol. Chem. 279:17914-17920, 2004). These non-protease interactions are important for both PAI-1 localization and function, and they are largely conformationally controlled through structural changes associated with RCL insertion (Seiffert et al., J. Biol. Chem. 272:13705-13710, 1997; Podor et al., J. Biol. Chem. 275:19788-19794, 2000; Webb et al., J Cell Biol 152: 741-752, 2001; Minor et al., J. Biol. Chem. 277:10337-10345, 2002; Stefansson et al., Sci. STKE. 2003:e24, 2003; Stefansson et al., J. Biol. Chem. 279: 29981-29987, 2004). In blood, most of the active PAI-1 circulates in complex with the glycoprotein vitronectin. The PAI-1 binding site for vitronectin has been localized to a region on the edge of β-sheet A in the PAI-1 structure (Lawrence et al., J Biol. Chem. 269: 15223-15228, 1994; Jensen et al., FEBS Lett. 521:91-94, 2002; Zhou et al., Nat. Struct. Biol. 10:541-544, 2003; Xu et al., J. Biol. Chem. 279:17914-17920, 2004). The binding site for LDL-R family members is less well characterized, but has been identified, in a region of PAI-1 associated with alpha helix D that is adjacent to the vitronectin binding domain (Stefansson et al., J Biol. Chem. 273:6358-6366, 1998; Horn et al., Thromb. Haemost. 80:822-828, 1998). The heparin binding domain on PAI-1 has also been mapped. This site also localizes to alpha helix D in a region homologous to the heparin binding domain of antithrombin III (Ehrlich et al., J. Biol. Chem. 267:11606-11611, 1992), and may overlap with the binding site for LDL-R family members.

Vitronectin circulates in plasma and is present in the extracellular matrix primarily at sites of injury or remodeling (Podor et al., J. Biol. Chem. 275:19788-19794, 2000; Tomasini et al., Vitronectin. Prog. Hemost. Thromb. 10:269-305, 1991; Seiffert, Histol. Histopathol. 12:787-797, 1997; Podor et al., J. Biol. Chem. 275:25402-25410, 2000; Podor et al., J. Biol. Chem. 277:7520-7528, 2002). PAI-1 and vitronectin appear to have a significant functional interdependence. Vitronectin stabilizes PAI-1 in its active conformation, thereby increasing its biological half-life (Lindahl et al., Thromb. Haemost. 62:748-751, 1989).

Vitronectin also enhances PAI-1 inhibitory efficiency for thrombin approximately 300-fold (Keijer et al, Blood 78:1254-1261, 1991; Naski et al., J. Biol. Chem. 268:12367-12372, 1993). In turn, PAI-1 binding to vitronectin alters its conformation from the native plasma form, which does not support cell adhesion, to an "activated" form that is competent to bind integrins. However, integrin binding is blocked by the presence of PAI-1 (Seiffert et al., J. Biol. Chem. 272: 13705-13710, 1997). As noted above, the association of PAI-1 with vitronectin is conformationally controlled and upon inhibition of a protease, the conformational change in PAI-1 associated with RCL insertion results in a loss of high affinity for vitronectin and a gain in affinity for LDL-R family members (Stefansson et al., J Biol. Chem. 273:6358-6366, 1998; Lawrence et al., J. Biol. Chem. 272:7676-7680, 1997). This is due to RCL insertion in PAI-1, disrupting the vitronectin binding site, while simultaneously exposing a cryptic receptor binding site that is revealed only when PAI-1 is in a complex with a protease (Sharp et al., Structure Fold. Des. 7:111-118, 1999; Stefansson et al., J Biol. Chem. 273:6358-6366, 1998; Stefansson et al., J. Biol. Chem. 279: 29981-29987, 2004), which results in an approximately 100,000-fold shift in the relative affinity of PAI-1 from vitronectin to LDL-R family members and a subsequent shift in PAI-1 localization from vitronectin to the cellular receptor (Stefansson et al., J Biol. Chem. 273:6358-6366, 1998; Lawrence et al., J. Biol. Chem. 272:7676-7680, 1997). Thus, PAI-1 association with vitronectin and LDL-R is conformationally controlled.

High PAI-1 levels are associated with both acute diseases such as sepsis and myocardial infarction (Colucci et al., J. Clin. Invest 75:818-824, 1985; Hamsten et al., N. Engl. J. Med. 313:1557-1563, 1985), and with chronic disorders including cancer, atherosclerosis, and type 2 diabetes (Stefansson et al., Current Pharmaceutical Design 9:1545-1564, 2003; De et al., Curr. Opin. Pharmacol. 5:149-154, 2005; Kannel, Lipids 40:1215-1220, 2005; Durand et al., Thromb. Haemost. 91:438-449, 2004). The association of PAI-1 with these diseases or syndromes has led to the hypothesis that PAI-1 is involved in their pathology. However, the mechanistic role that PAI-1 plays in disease development is not clear and is likely to be complex since PAI-1 can act through multiple pathways, such as modulating fibrinolysis through the regulation of plasminogen activators, or by influencing tissue remodeling through the direct regulation of cell migration (Stefansson et al., Sci. STKE. 2003:e24, 2003; Stefansson et al., Nature 383:441-443, 1996; Deng et al., J Cell Biol. 134:1563-1571, 1996; Czekay et al., J. Cell Biol. 160:781-791, 2003; Cao et al., EMBO J. 25:1860-1870, 2006).

In cardiovascular disease, PAI-1 expression is significantly increased in severely atherosclerotic vessels (Schneiderman et al., Proc. Natl. Acad. Sci. USA 89:6998-7002, 1992; Lupu et al., Arterioscler. Thromb. 13:1090-1100, 1993), and PAI-1 protein levels rise consistently during disease progression from normal vessels to fatty streaks to atherosclerotic plaques (Robbie et al., Arterioscler. Thromb. Vasc. Biol. 16:539-545, 1996). Increased PAI-1 levels are also linked to obesity, and insulin resistance (Alessi et al., Diabetes 46:860-867, 1997; Loskutoff et al., Arterioscler. Thromb. Vasc. Biol. 18:1-6, 1998; Schafer et al., FASEB J. 15:1840-1842, 2001).

In addition, elevated plasma levels of PAI-1 have been associated with thrombotic events (Krishnamurti, Blood, 69: 798, 1987); Reilly, Arteriosclerosis and Thrombosis, 11:1276, 1991), and antibody neutralization of PAI-1 activity resulted in promotion of endogenous thrombolysis and reperfusion (Biemond, Circulation, 91:1175, 1995; Levi, Circulation 85: 305, 1992). Elevated levels of PAI-1 have also been implicated in polycystic ovary syndrome (Nordt, J. Clin. Endocrin. Metabol. 85:1563, 2000) and bone loss induced by estrogen deficiency (Daci, J. Bone Min. Res. 15:1510, 2000).

PAI-1 is synthesized in both murine and human adipocytes (Alessi et al., Diabetes 46:860-867, 1997; Samad et al., J. Clin. Invest 97:37-46, 1996; Morange et al., Diabetes 48:890-895, 1999; Sakamoto et al., Am. J. Physiol 276:C1391-C1397, 1999; Samad et al., Ann. N. Y. Acad. Sci. 811:350-358, 1997; Lundgren et al., Circulation 93:106-110, 1996; Cigolini et al., Atherosclerosis 143:81-90, 1999; Crandall et al., Biochem. Biophys. Res. Commun. 279:984-988, 2000; Gottschling-Zeller et al., Diabetologia 43:377-383, 2000). There is also a strong correlation between the amount of visceral fat and plasma levels of PAI-1 in humans (Alessi et al., Diabetes 46:860-867, 1997; Vague et al., Metabolism 35:250-253, 1986; Mavri et al., Arterioscler. Thromb. Vasc. Biol. 19:1582-1587, 1999; Giltay et al., Arterioscler. Thromb. Vasc. Biol. 18:1716-1722, 1998) and mice (Samad et al., Mol. Med. 2:568-582, 1996; Shimomura et al., Nat. Med. 2:800-803, 1996). This dramatic up-regulation of PAI-1 in obesity has lead to the suggestion that adipose tissue itself may directly contribute to elevated systemic PAI-1, which in-turn increases the probability of vascular disease through increased thrombosis, and accelerated atherosclerosis. Notably, very recent data suggests that PAI-1 may also play a direct role in obesity (Schafer et al., FASEB J. 15:1840-1842, 2001; Ma et al, Diabetes 53:336-346, 2004; De Taeye et al., J. Biol. Chem. 281:32796-32805, 2006; Crandall et al., Arterioscler. Thromb. Vasc. Biol. 26: 2209-2215, 2006; Liang et al., Am. J. Physiol Endocrinol. Metab 290:E103-E113, 2006).

In one study, genetically obese and diabetic ob/ob mice crossed into a PAI-1 deficient background had significantly reduced body weight and improved metabolic profiles compared to ob/ob mice with PAI-1 (Schafer et al., FASEB J. 15:1840-1842, 2001). Likewise, nutritionally-induced obesity and insulin resistance were dramatically attenuated in mice genetically deficient in PAI-1 (Ma et al, Diabetes 53:336-346, 2004; De Taeye et al., J. Biol. Chem. 281:32796-32805, 2006) and in mice treated with an orally active PAI-1 inhibitor (Crandall et al., Arterioscler. Thromb. Vasc. Biol. 26: 2209-2215, 2006). The improved adiposity and insulin resistance in PAI-1-deficient mice may be related to the observation that PAI-1 deficient mice on a high fat diet had increased metabolic rates and total energy expenditure compared to wild-type mice, and peroxysome proliferator-activated receptor (PPARγ) and adiponectin were maintained (Ma et al, Diabetes 53:336-346, 2004). However, the precise mechanism involved was not shown and may be complex, since the over-expression of PAI-1 in mice also impaired adipose tissue formation (Lijnen et al., J. Thromb. Haemost. 3:1174-1179, 2005). Taken together, these observations suggest that PAI-1 plays a previously unrecognized direct role in obesity and insulin resistance that involves interactions beyond its identified activities of modulating fibrinolysis and tissue remodeling.

Indeed, if PAI-1 positively regulates adipose tissue development, then the association of increased PAI-1 expression with developing obesity may constitute a positive feedback loop promoting adipose tissue expansion and dysregulation of normal cholesterol homeostasis. Thus, there exists a need in the art for a greater understanding of how PAI-1 is involved in metabolism, obesity and insulin resistance. The invention provides methods of identifying and using inhibitors of PAI-1.

SUMMARY OF THE INVENTION

The invention provides plasminogen activator inhibitor-1 (PAI-1) inhibitors and uses thereof to modulate lipid metabolism. The invention also provides PAI-1 inhibitors and uses thereof in the treatment of any disease or condition associated with elevated PAI-1.

In one embodiment, a method of identifying a PAI-1 inhibitor is provided. The method comprises measuring binding of PAI-1 to VLDL-R in the presence of ApoE and/or VLDL, and in the presence or absence of a candidate compound. Decreased binding of PAI-1 to VLDL-R in the presence of the candidate compound compared to binding in the absence of the candidate compound indicates the candidate compound is an inhibitor of PAI-1 binding to VLDL-R. In one aspect, the candidate compound decreases PAI-1 binding to VLDL compared to binding in the absence of the candidate compound. In another aspect, the candidate compound decreases PAI-1 binding to ApoE compared to binding in the absence of the candidate compound. In another aspect, the candidate compound decreases PAI-1 binding to VLDL-R in the presence of vitronectin and/or uPA compared to binding in the absence of the candidate compound.

In another embodiment, the method comprises measuring binding of PAI-1 to ApoA and/or an ApoA receptor in the presence compared to the absence of a candidate compound. Decreased binding of PAI-1 to ApoA in the presence of the candidate compound indicates the candidate compound is an inhibitor of PAI-1 binding to ApoA. In one aspect, the candidate decreases PAI-1 binding to ApoA.

In another aspect, PAI-1 inhibitors identified by the methods disclosed herein are also provided. Such PAI-1 inhibitors include, but are not limited to, hexachlorophene, quinalizarin, 5-nitrosalicylic acid, chlorogenic acid, caffeic acid, 3-nitro-L-tyrosine, 3-chloro-L-tyrosine, 5-chlorosalicylic acid, polyphenon-60, tannic acid, epigallocatechin 3,5-digallate, (−)-epigallocatechin gallate (EGCG), and gallic acid, or another PAI-1 inactivator. Such PAI-1 inhibitors are depicted in FIG. 1.

Chemically synthesized PAI-1 inhibitors are also provided. Such PAI-1 inhibitors include, but are not limited to, any of the compounds of Formulas I-XXXIV as set out herein. Such PAI-1 inhibitors are also depicted in Table 1.

In another embodiment, methods of increasing circulating HDL and/or decreasing VLDL in a subject are provided. The methods comprise administering to a subject in need thereof a PAI-1 inhibitor in an amount effective to increase HDL and/or decrease VLDL. In one aspect, the subject is human. In another aspect, the PAI-1 inhibitor is tannic acid, epigallocatechin 3, 5 digallate, (−)-epigallocatechin gallate (EGCG), or gallic acid. In a further aspect, the PAI-1 inhibitor is a compound of any of Formulas I-XXXIV.

Uses of compounds of the invention for the production of a medicament for the treatment or prevention of any condition or disease discussed herein are also provided. The compounds of the invention are inhibitors of the serine protease inhibitor PAI-1, and are therefore useful in the treatment or prophylaxis of those processes which involve the production and/or action of PAI-1. Thus, uses of the compounds of the invention in the regulation of lipid metabolism are provided. In one aspect, the compounds of the invention are useful in treating high cholesterol and diseases associated with elevated levels of PAI-1. In another aspect, the compounds of the invention are useful in treating elevated levels of VLDL or LDL. In another aspect, the compounds of the invention are useful in elevating HDL.

In one embodiment, the invention includes the uses of these inhibitors for the treatment of many conditions, diseases or disorders associated with PAI-1 activity. Such conditions or disorders include, but are not limited to, inflammation, cell migration and migration-driven proliferation of cells, and angiogenesis or thrombosis. Such inhibitors are also contemplated to be useful for modulation of endogenous fibrinolysis, and in conjunction with pharmacologic thrombolysis.

In another embodiment, the PAI-1 inhibitor decreases PAI-1 binding to ApoE, ApoA, VLDL, VLDL-R, ApoA-R, or LDL. In yet another aspect, the PAI-1 inhibitor binds to PAI-1 in the presence of vitronectin and/or uPA.

In yet another embodiment, a method of modulating cholesterol and/or lipid uptake is provided. The method comprises administering a PAI-1 inhibitor to a subject in an amount effective to modulate cholesterol and/or lipid uptake.

In still another embodiment, a method of modulating cholesterol and/or lipid clearance is provided. The method comprises administering a PAI-1 inhibitor to a subject in an amount effective to modulate cholesterol and/or lipid clearance. In one aspect, the PAI-1 inhibitor is administered to a subject in an amount effective to inhibit VLDL or ApoE or ApoA binding to VLDL-R. In one aspect, the PAI-1 inhibitor is administered to a subject in an amount effective to affect HDL or ApoE or ApoA binding to an ApoA receptor and modulate cholesterol and/or lipid clearance.

In a further embodiment, methods of treating a disease or condition associated with elevated levels of PAI-1 are provided. In another embodiment, methods of treating a disease or condition associated with elevated levels of VLDL or LDL are provided. In yet another embodiment, methods of treating a disease or condition associated with high cholesterol or elevated triglycerides are provided. In one aspect, the disease or condition is associated with insulin resistance, obesity, non-insulin dependent diabetes mellitus, and atherosclerosis. In another aspect, the disease or condition involves thrombosis or prothrombosis which includes, but is not limited to, formation of atherosclerotic plaques, venous and arterial thrombosis, myocardial ischemia, atrial fibrillation, deep vein thrombosis, coagulation syndromes, pulmonary thrombosis, cerebral thrombosis, thromboembolic complications of surgery, and peripheral arterial occlusion. In another aspect, the disease or condition is associated with extracellular matrix accumulation, including, but not limited to, renal fibrosis, chronic obstructive pulmonary disease, polycystic ovary syndrome, restenosis, renovascular disease, diabetic nephropathy, and organ transplant rejection.

In yet another aspect, the disease or condition associated with neoangiogenesis, myelofibrosis, or fibrinolytic impairment. In an even further aspect of the invention, the disease or condition includes, but is not limited to, cancer, septicemia, obesity, insulin resistance, proliferative diseases such as psoriasis, improving coagulation homeostasis, cerebrovascular diseases, microvascular disease, hypertension, dementia, atherosclerosis, osteoporosis, arthritis, asthma, heart failure, arrhythmia, angina, and as a hormone replacement agent, treating, preventing or reversing progression of atherosclerosis, Alzheimer's disease, osteoporosis, osteopenia; reducing inflammatory markers, fibrinolytic disorder, reducing C-reactive protein, or preventing or treating low grade vascular inflammation, stroke, dementia, coronary heart disease, primary and secondary prevention of myocardial infarction, stable and unstable angina, primary prevention of coronary events, secondary prevention of cardiovascular events, peripheral vascular disease, peripheral arterial disease, acute vascular syndromes, deep vein thrombosis, pulmonary embolism, reducing the risk of undergoing a myocardial revascularization procedure, microvascular diseases such as nephropathy, neuropathy, retinopathy and nephrotic syndrome, hypertension, Type 1 and 2 diabetes and related diseases, hyperglycemia, hyperinsulinemia, malignant lesions, premalignant lesions, gastrointestinal malignancies, liposarcoma, an epithelial tumor, psoriasis, inflammation, and septic shock.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. Additional features and variations of the invention will be apparent to those skilled in the art from the entirety of this application, and all such features are intended as aspects of the invention.

BRIEF DESCRIPTION OF THE DRAWINGS

FIGS. 1A-1C show some of the PAI-1 inhibitor compounds of the invention and their associated properties.

FIGS. 4A-4C show that the inhibition of PAI-1 by tannic acid is pH sensitive.

FIGS. 8A-8L show the inhibition of PAI-1 by various CDE-inhibitor compounds at pH 7.5 on both a liner and a log scale.

DETAILED DESCRIPTION OF THE INVENTION

The invention describes materials and methods for the modulation of lipid metabolism through the inhibition of plasminogen activator inhibitor-1 (PAI-1) that may be unrelated to its role as a fibrinolytic inhibitor. The data presented herein demonstrate that the removal of active PAI-1, either genetically or pharmacologically, influences steady-state lipid levels in the plasma of mice, suggesting an interaction between PAI-1 or the plasminogen activator system and lipid metabolism.

PAI-1 Inhibitor Compounds of the Invention

Figure 1C:
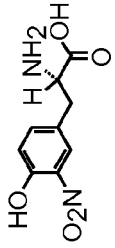
Figure 2A:
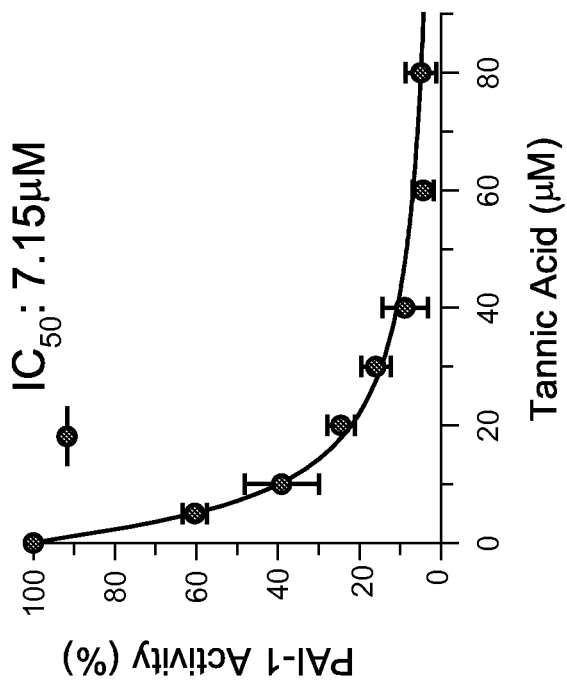
FIGS. 2A-2D show some of the PAI-1 inhibitor compounds of the invention (tannic acid, epigallocatechin 3,5, digallate, epigallocatechin gallate (EGCG) and gallic acid) their $IC_{50}$s against PAI-1 at pH 7.5.
Figure 2A:
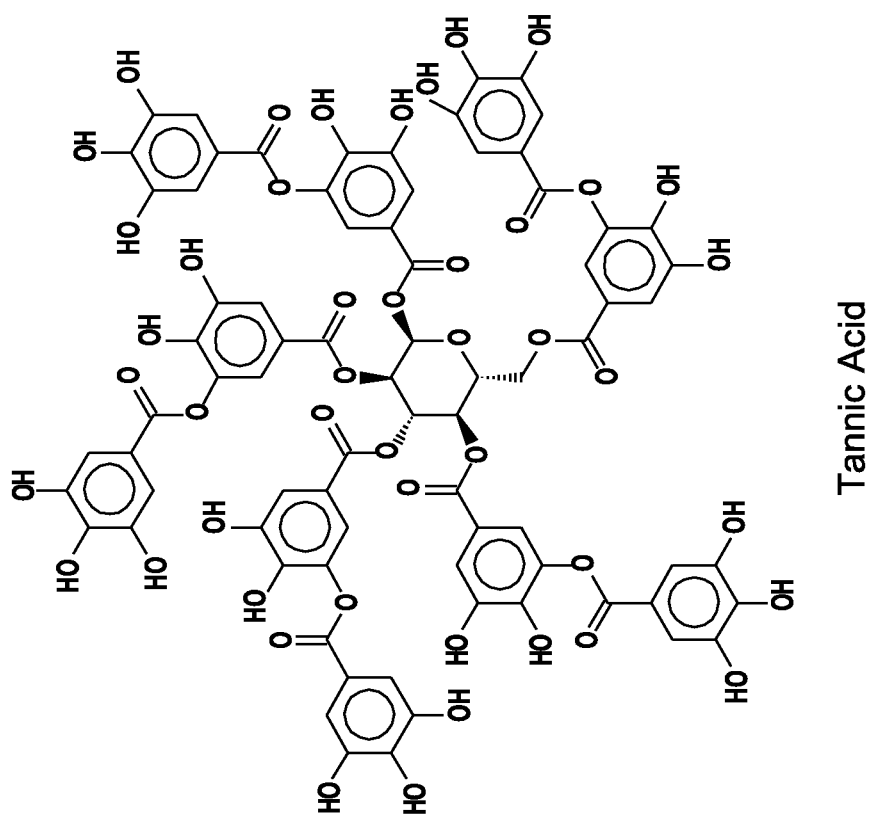
Figure 2B:
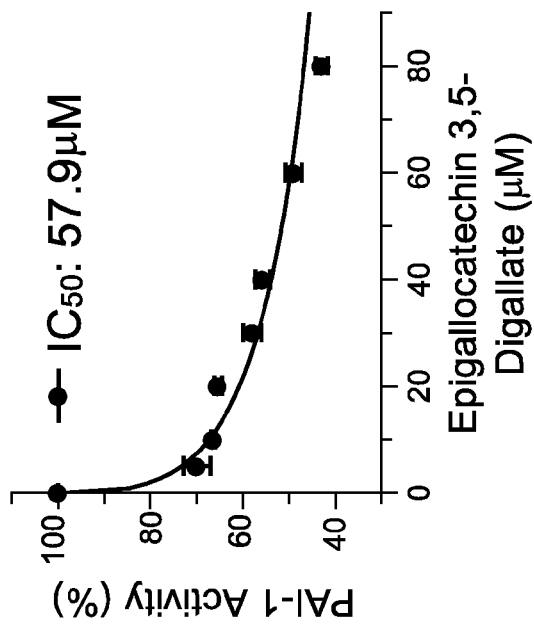
Figure 2B:
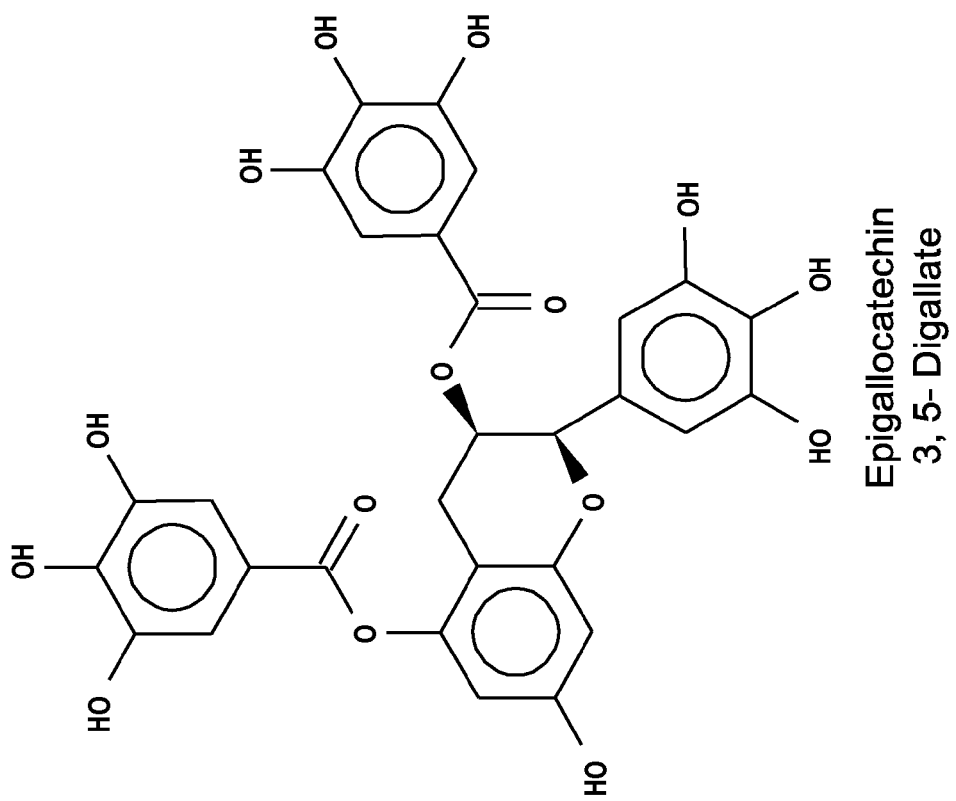
Figure 2C:
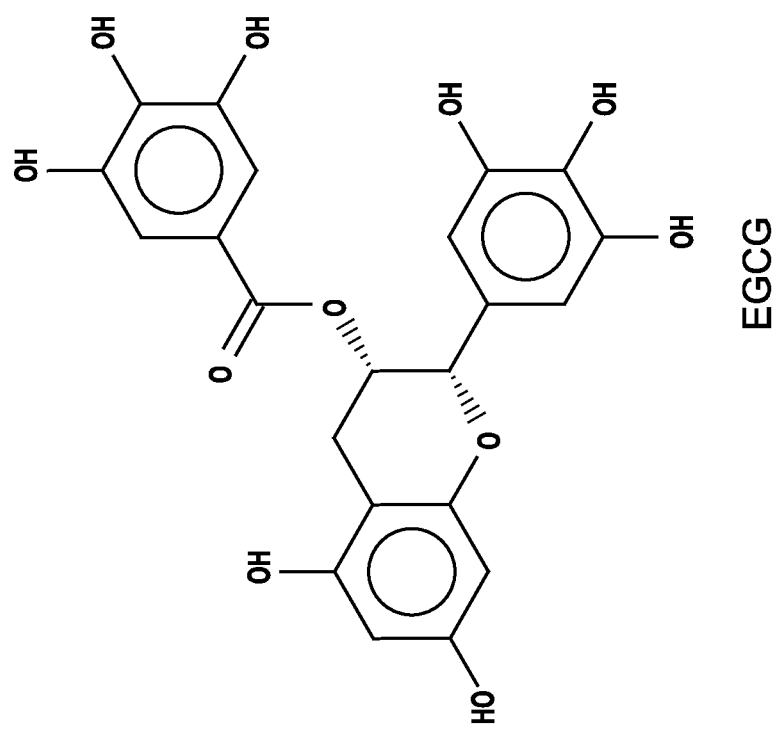
Figure 2C:
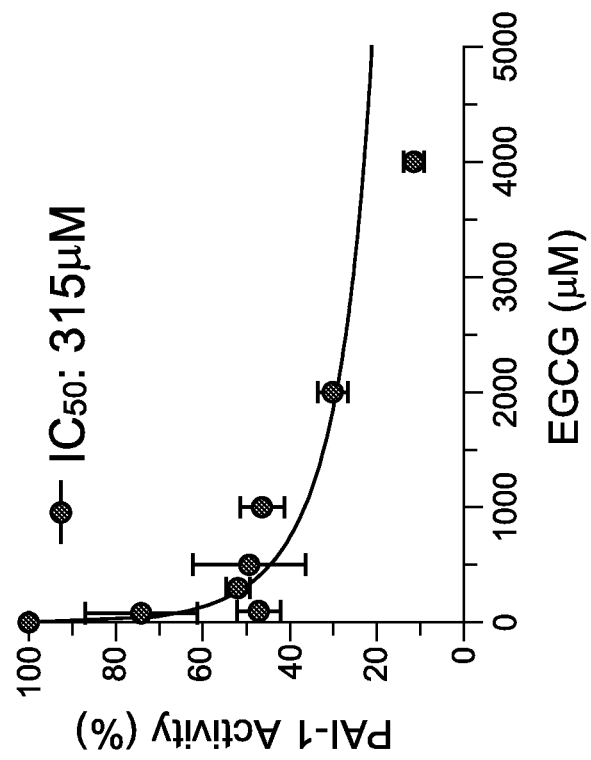
Figure 2D:
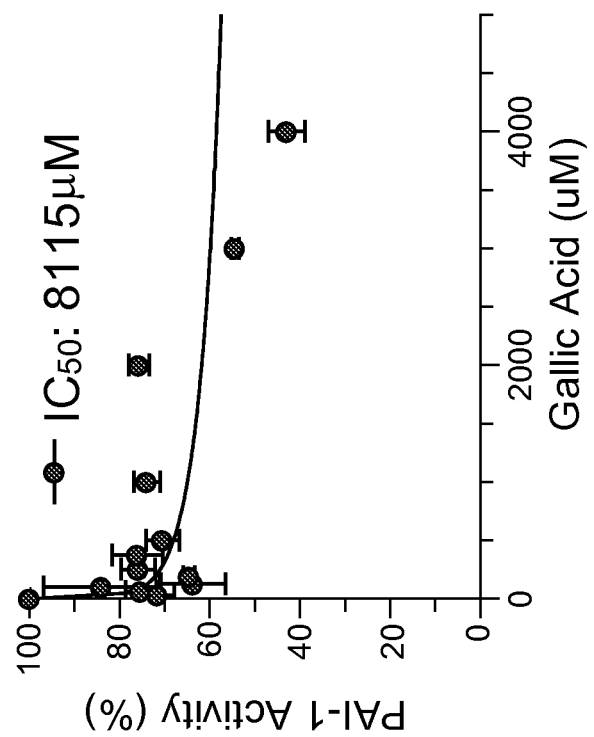
Figure 2D:
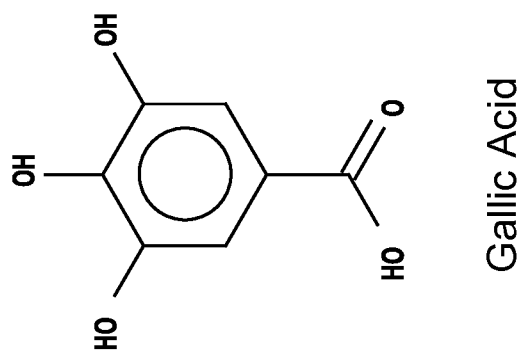

PAI-1 inhibitor compounds of the invention include, but are not limited to, compounds identified by the methods of the invention. Such PAI-1 inhibitors include, but are not limited to, hexachlorophene, quinalizarin, 5-nitrosalicylic acid, chlorogenic acid, caffeic acid, 3-nitro-L-tyrosine, 3-chloro-L-tyrosine, 5-chlorosalicylic acid, polyphenon-60 (an extract from green tea), tannic acid, epigallocatechin 3,5-digallate, (−)-epigallocatechin gallate (EGCG), and gallic acid. Such PAI-1 inhibitors are depicted in FIG. 1.

Chemically synthesized PAI-1 inhibitors are also provided in the invention. Such PAI-inhibitors include, but are not limited to, the compounds provided herein below or a pharmaceutically acceptable salt or ester thereof.

Compounds of the invention include those of formula (I):

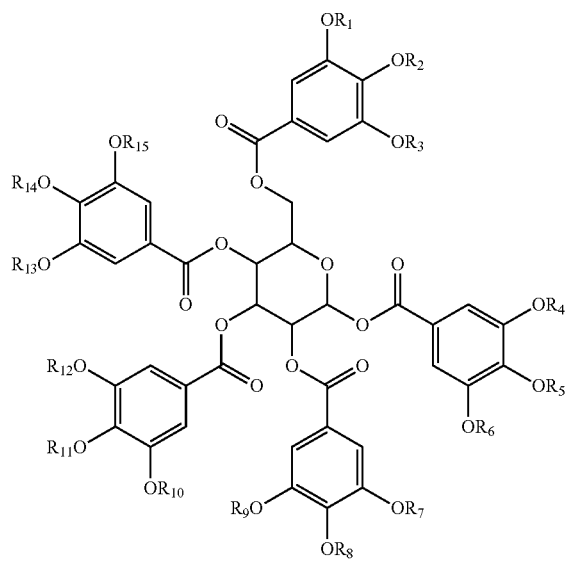

(I)

wherein:

$R_1$ to $R_{15}$ are independently selected from the group consisting of H, methyl, ethyl, n-propyl, iso-propyl, n-butyl, iso-butyl, tert-butyl, phenyl, tolyl, and benzyl.

Compounds of the invention include those of formula (II):

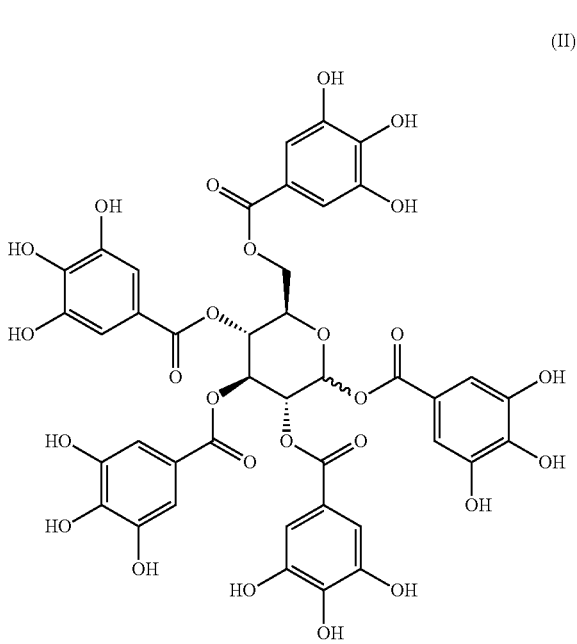 [SMILES: O=C(OC[C@H]1OC(OC(=O)c2cc(O)c(O)c(O)c2)[C@H](OC(=O)c2cc(O)c(O)c(O)c2)[C@@H](OC(=O)c2cc(O)c(O)c(O)c2)[C@@H]1OC(=O)c1cc(O)c(O)c(O)c1)c1cc(O)c(O)c(O)c1]

(II)

Compounds of the invention include those of formula (III):

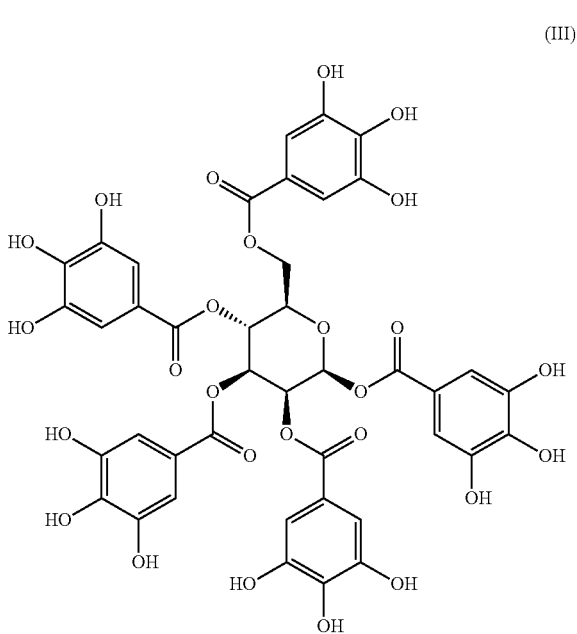 [SMILES: O=C(OC[C@H]1O[C@@H](OC(=O)c2cc(O)c(O)c(O)c2)[C@@H](OC(=O)c2cc(O)c(O)c(O)c2)[C@@H](OC(=O)c2cc(O)c(O)c(O)c2)[C@@H]1OC(=O)c1cc(O)c(O)c(O)c1)c1cc(O)c(O)c(O)c1]

(III)

Compounds of the invention include those of formula (IV):
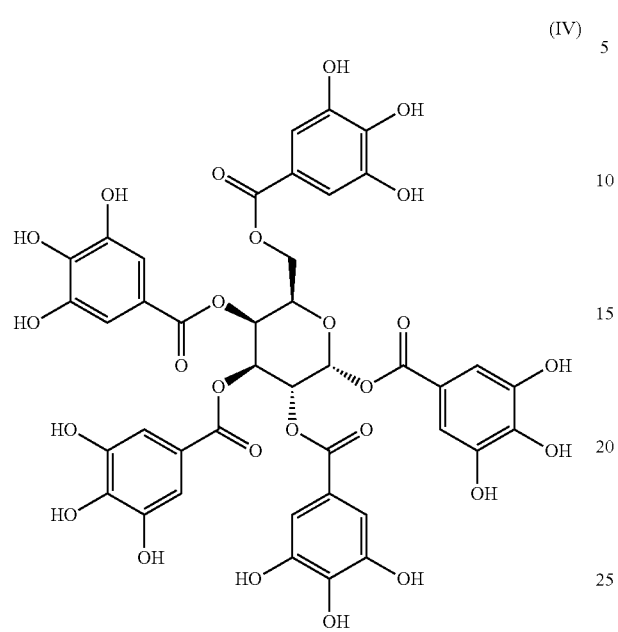
Compounds of the invention include those of formula (V):
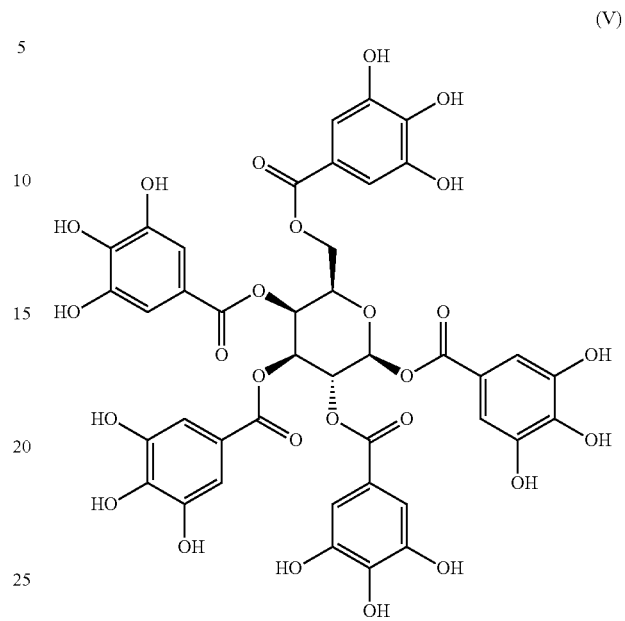
Compounds of the invention include those of formula (VI):
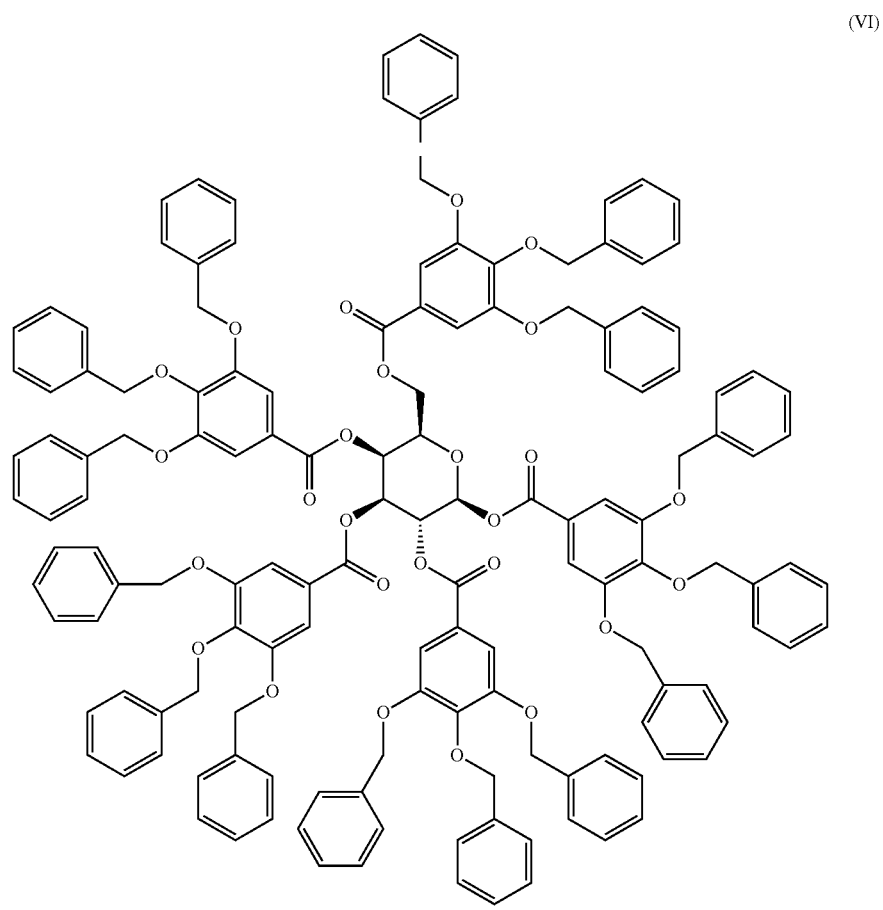

Compounds of the invention include those of formula (VII):

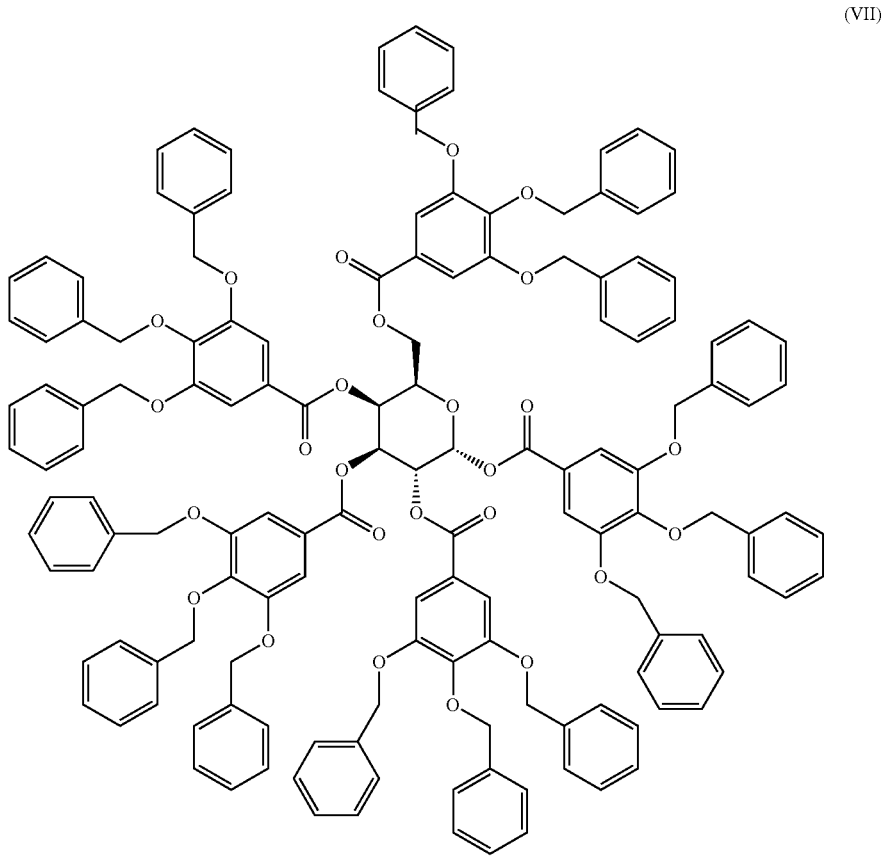

(VII)

Compounds of the invention include those of formula (VIII):

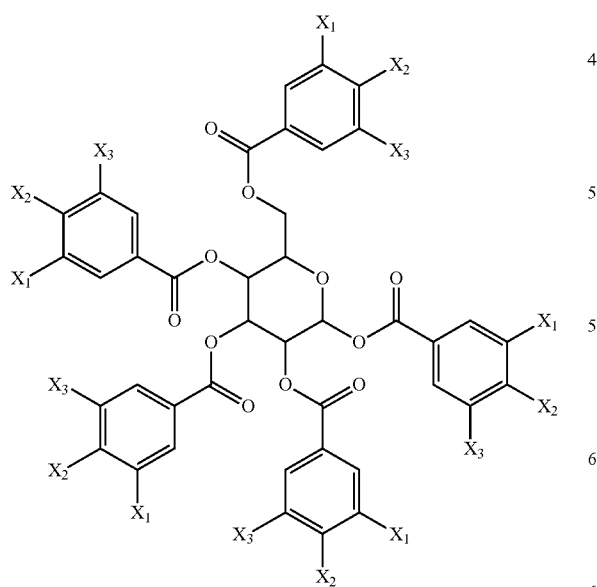

(VIII)

wherein:

$X_1$ to $X_3$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S═O, aryl, substituted aryl, and heteroaryl; and R is C$_1$ to C$_6$ alkyl, C$_3$ to C$_6$ cycloalkyl, CH$_2$—C$_3$-C$_6$ cycloalkyl, phenyl, tolyl, or benzyl;

with the proviso that at least one of $X_1$ to $X_3$ is —OH.

Compounds of the invention include those of formula (IX):

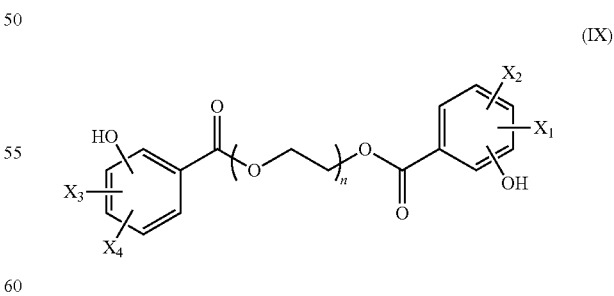

(IX)

wherein:
n=1 to 6;

$X_1$ to $X_4$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S═O, aryl, substituted aryl, and heteroaryl; and R is $C_1$ to $C_6$ alkyl, $C_3$ to $C_6$ cycloalkyl, $CH_2$—$C_3$-$C_6$ cycloalkyl, phenyl, tolyl, or benzyl.

Compounds of the invention include those of formula (IX):

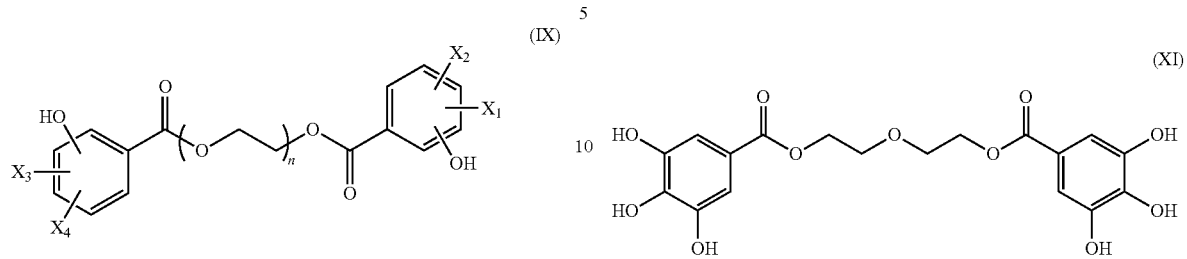

(IX)

wherein:
n=1 to 6; and
$X_1$ to $X_4$ are all —OH.

Compounds of the invention include those of formula (XXVIII):

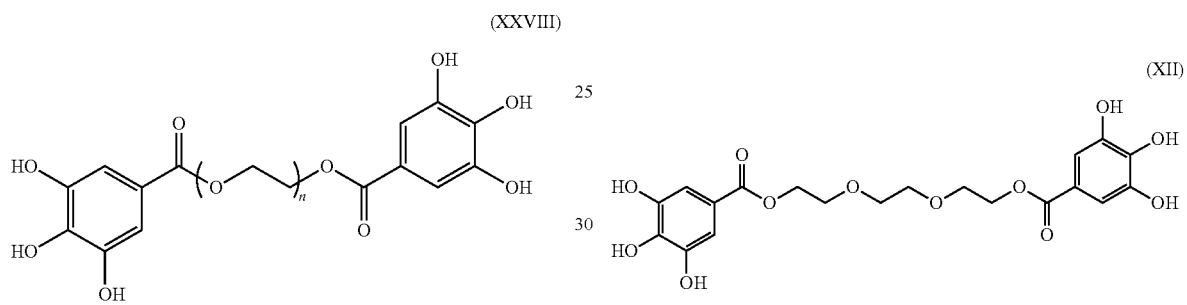

(XXVIII)

wherein:
n=1 to 6.

Compounds of the invention include those of formula (X):

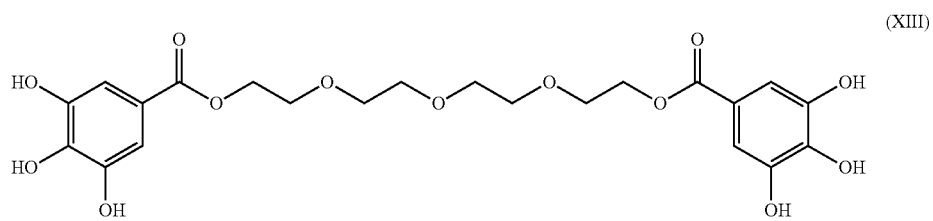 [SMILES: O=C(OCCOCCOCCOCCOC(=O)c1cc(O)c(O)c(O)c1)c1cc(O)c(O)c(O)c1]

(X)

Compounds of the invention include those of formula (XI):

(XI)

Compounds of the invention include those of formula (XII):

(XII)

Compounds of the invention include those of formula (XIII):

(XIII)

Compounds of the invention include those of formula (XIV):

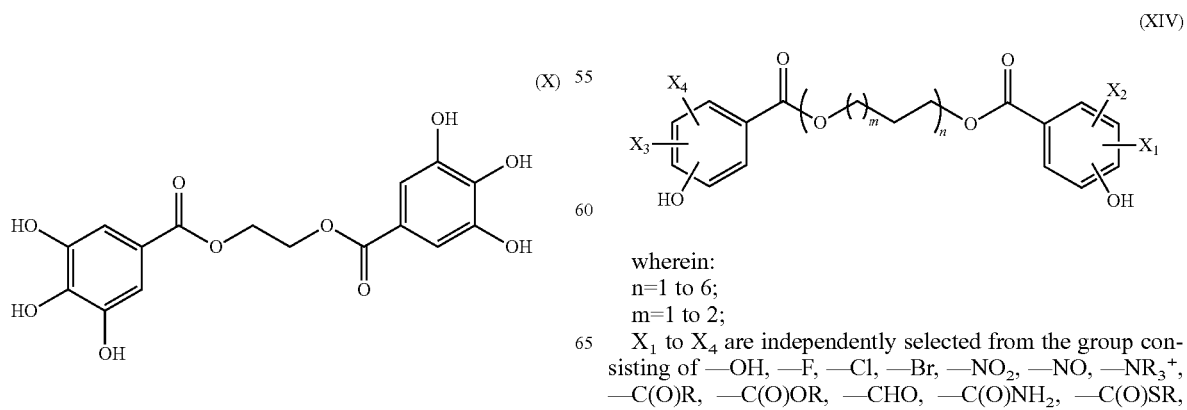

(XIV)

wherein:
n=1 to 6;
m=1 to 2;
$X_1$ to $X_4$ are independently selected from the group consisting of —OH, —F, —Cl, —Br, —$NO_2$, —NO, —$NR_3^+$, —C(O)R, —C(O)OR, —CHO, —C(O)$NH_2$, —C(O)SR, —CN, —S(O)₂R, —SO₃R, —SO₃H, —SO₂NR₂, —S=O, aryl, substituted aryl, and heteroaryl; and R is $C_1$ to $C_6$ alkyl, $C_3$ to $C_6$ cycloalkyl, $CH_2$—$C_3$-$C_6$ cycloalkyl, phenyl, tolyl, or benzyl.

Compounds of the invention include those of formula (XIV):

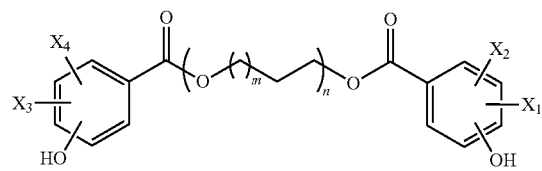

(XIV)

wherein:

n=1 to 6;

m=1 to 2; and $X_1$ to $X_4$ are all —OH.

Compounds of the invention include those of formula (XV):

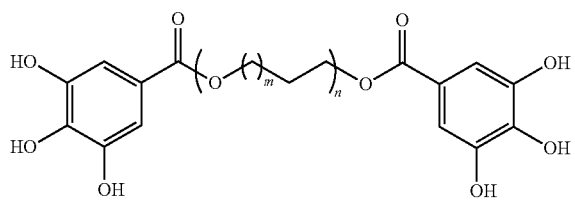

(XV)

wherein:

n=1 to 6; and m=1 to 2.

Compounds of the invention include those of formula (XVI):

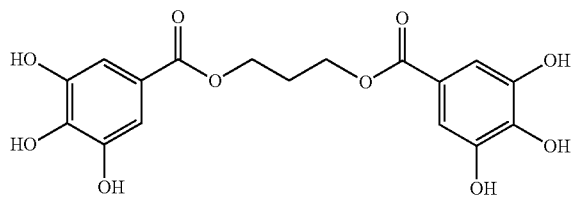

(XVI)

Compounds of the invention include those of formula (XVII):

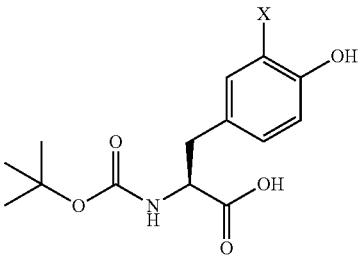

(XVII)

wherein:

X is —OH, —F, —Cl, —Br, —NO₂, —NO, —NR₃⁺, —C(O)R, —C(O)OR, —CHO, —C(O)NH₂, —C(O)SR, —CN, —S(O)₂R, —SO₃R, —SO₃H, —SO₂NR₂, S=O, aryl, substituted aryl, or heteroaryl; and R is $C_1$ to $C_6$ alkyl, $C_3$ to $C_6$ cycloalkyl, $CH_2$—$C_3$-$C_6$ cycloalkyl, phenyl, tolyl, or benzyl.

Compounds of the invention include those of formula (XVIII):

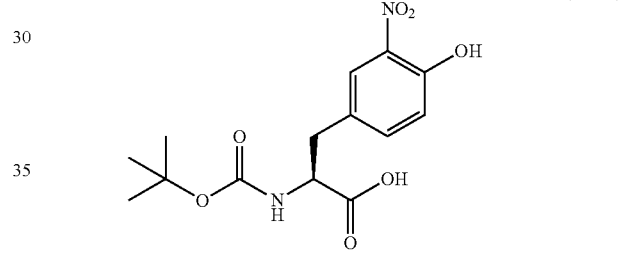

(XVIII)

Compounds of the invention include those of formula (XIX):

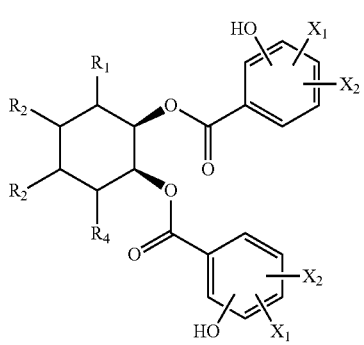

(XIX)

wherein:

$R_1$ to $R_4$ are independently selected from the group consisting of H, methyl, ethyl, n-propyl, iso-propyl, n-butyl, iso-butyl, tert-butyl, phenyl, tolyl, and benzyl;

$X_1$ to $X_2$ are independently selected from the group consisting of —OH, —F, —Cl, —Br, —NO₂, —NO, —NR₃⁺, —C(O)R, —C(O)OR, —CHO, —C(O)NH₂, —C(O)SR, —CN, —S(O)₂R, —SO₃R, —SO₃H, —SO₂NR₂, —S=O, aryl, substituted aryl, and heteroaryl; and R is $C_1$ to $C_6$ alkyl, $C_3$ to $C_6$ cycloalkyl, —$CH_2$—$C_3$-$C_6$ cycloalkyl, phenyl, tolyl, or benzyl.

Compounds of the invention include those of formula (XX):

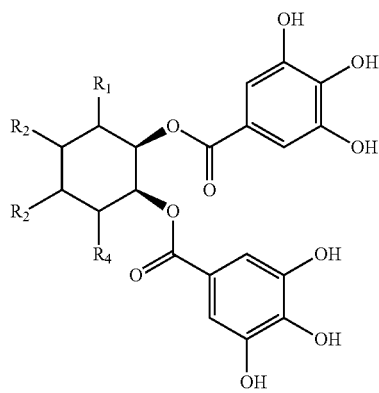

wherein:

$R_1$ to $R_4$ are independently selected from the group consisting of H, methyl, ethyl, n-propyl, iso-propyl, n-butyl, iso-butyl, tert-butyl, phenyl, tolyl, and benzyl.

Compounds of the invention include those of formula (XXI):

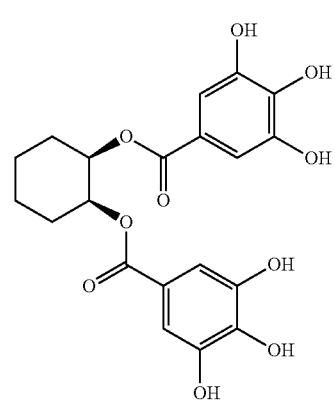

Compounds of the invention include those of formula (XXII):

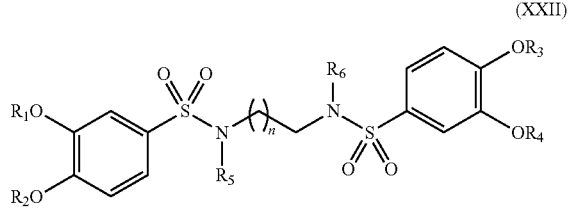

wherein:

n=1 to 5; and $R_1$ to $R_6$ are independently selected from the group consisting of H, methyl, ethyl, n-propyl, iso-propyl, n-butyl, iso-butyl, tert-butyl, phenyl, tolyl, and benzyl.

Compounds of the invention include those of formula (XXIII):

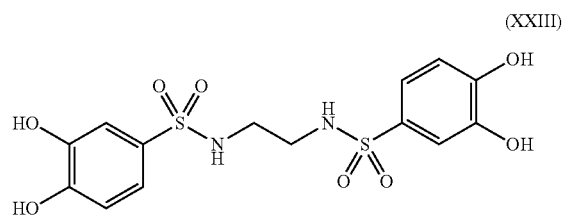 [SMILES: O=S(=O)(NCCNS(=O)(=O)c1ccc(O)c(O)c1)c1ccc(O)c(O)c1]

Compounds of the invention include those of formula (XXIV):

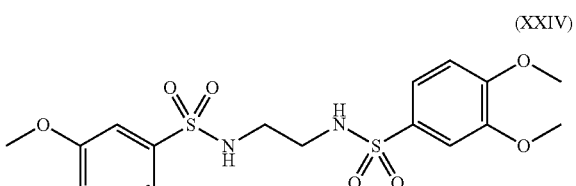

Compounds of the invention include those of formula (XXV):

(XXV)

Compounds of the invention include those of formula (XXVI):

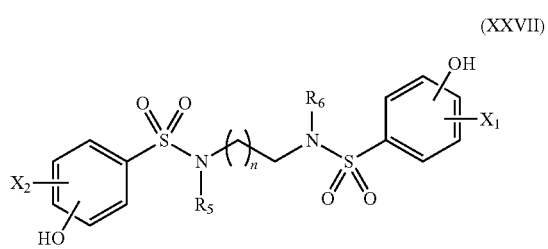

Compounds of the invention include those of formula (XXVII):

(XXVII)

wherein:

n=1 to 5;

$R_5$ to $R_6$ are independently selected from the group consisting of H, methyl, ethyl, n-propyl, iso-propyl, n-butyl, iso-butyl, tert-butyl, phenyl, tolyl, and benzyl; $X_1$ to $X_2$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S=O, aryl, substituted aryl, and heteroaryl; and R is $C_1$ to $C_6$ alkyl, $C_3$ to $C_6$ cycloalkyl, —CH$_2$—C$_3$-C$_6$ cycloalkyl, phenyl, tolyl, or benzyl.

Compounds of the invention include those of formula (XXIX):

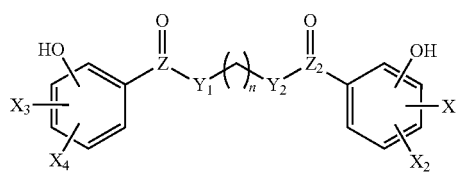

(XXIX)

wherein:

n=0 to 6;

$X_1$ to $X_4$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S=O, aryl, substituted aryl, and heteroaryl;

$Y_1$ to $Y_2$ are independently selected from the group consisting of O, NH, NR, S, and CH$_2$;

$Z_1$ to $Z_2$ are independently selected from the group consisting of C, S, and S=O; and R is $C_1$ to $C_6$ alkyl, $C_3$ to $C_6$ cycloalkyl, CH$_2$—C$_3$-C$_6$ cycloalkyl, phenyl, tolyl, or benzyl.

Compounds of the invention include those of formula (XXXIV):

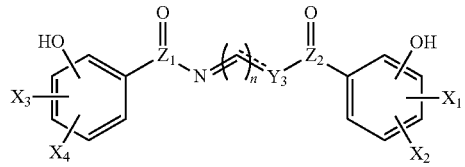

(XXXIV)

wherein:

n=0 to 5;

$X_1$ to $X_4$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S=O, aryl, substituted aryl, and heteroaryl;

$Y_3$ is O, N, NH, NR, S, and CH$_2$;

$Z_1$ to $Z_2$ are independently selected from the group consisting of C, S, and S=O;

---- is an optional double bond; and

R is $C_1$ to $C_6$ alkyl, $C_3$ to $C_6$ cycloalkyl, —CH$_2$—C$_3$-C$_6$ cycloalkyl, phenyl, tolyl, or benzyl.

Compounds of the invention include those of formula (XXX):

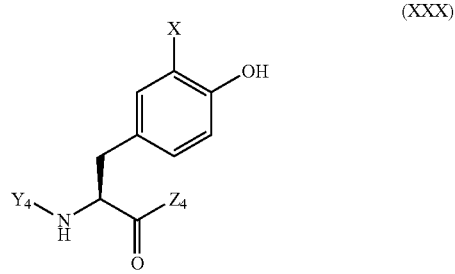

(XXX)

wherein:

X is —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, S=O, aryl, substituted aryl, or heteroaryl;

$Y_4$ is —OH, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S=O, aryl, substituted aryl, heteroaryl, or one or more amino acids;

$Z_4$ is —R, —OR, —NH$_2$, —NHR, —NR$_2$, —NOR, —SR, or one or more amino acids; and R is $C_1$ to $C_6$ alkyl, $C_3$ to $C_6$ cycloalkyl, CH$_2$—C$_3$-C$_6$ cycloalkyl, phenyl, tolyl, or benzyl.

Compounds of the invention include those of formula (XXXI):

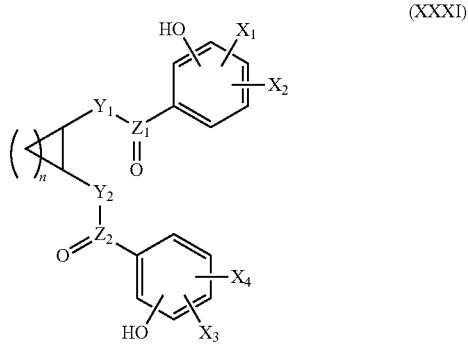

(XXXI)

wherein:

n=1 to 6;

$X_1$ to $X_4$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S=O, aryl, substituted aryl, and heteroaryl;

$Y_1$ to $Y_2$ are independently selected from the group consisting of O, NH, NR, S, and CH$_2$;

$Z_1$ to $Z_2$ are independently selected from the group consisting of C, S, and S=O; and R is $C_1$ to $C_6$ alkyl, $C_3$ to $C_6$ cycloalkyl, —CH$_2$—C$_3$-C$_6$ cycloalkyl, phenyl, tolyl, or benzyl.

Compounds of the invention include those of formula (XXXII):

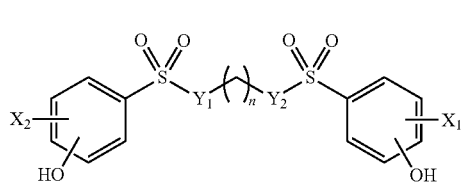

wherein:

n=0 to 5;

$X_1$ to $X_2$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S=O, aryl, substituted aryl, and heteroaryl;

$Y_1$ to $Y_2$ are independently selected from the group consisting of O, NH, NR, S, and CH$_2$; and R is $C_1$ to $C_6$ alkyl, $C_3$ to $C_6$ cycloalkyl, —CH$_2$—$C_3$-$C_6$ cycloalkyl, phenyl, tolyl, or benzyl.

Compounds of the invention include those of formula (XXXIII):

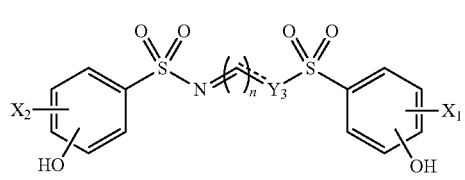

wherein:

n=0 to 5;

$X_1$ to $X_2$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S=O, aryl, substituted aryl, and heteroaryl;

$Y_3$ is O, N, NH, NR, S, and CH$_2$;

---- is an optional double bond; and

R is $C_1$ to $C_6$ alkyl, $C_3$ to $C_6$ cycloalkyl, —CH$_2$—$C_3$-$C_6$ cycloalkyl, phenyl, tolyl, or benzyl.

These compounds are depicted in Table 1 herein below.

TABLE 1

| Synthesized PAI-1 Inhibitor Compounds | | |
|---|---|---|
| CDE No. | Formula No. | Structure |
| | (I) | 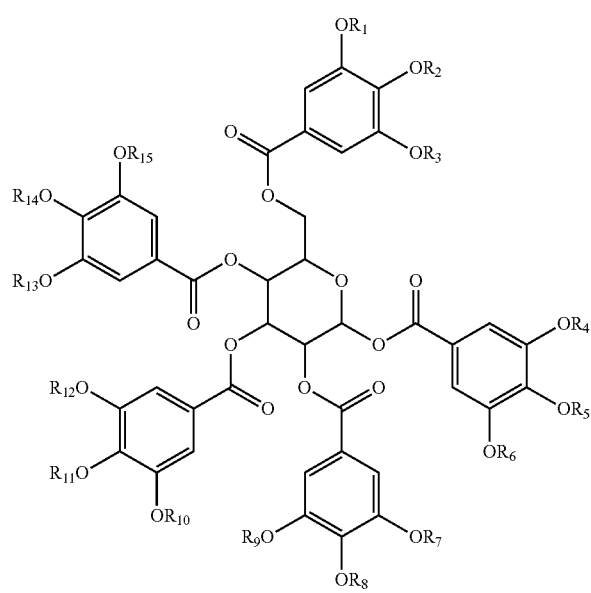 |

TABLE 1-continued
Synthesized PAI-1 Inhibitor Compounds
| CDE No. | Formula No. | Structure |
|---|---|---|
| CDE-001 | (II) | 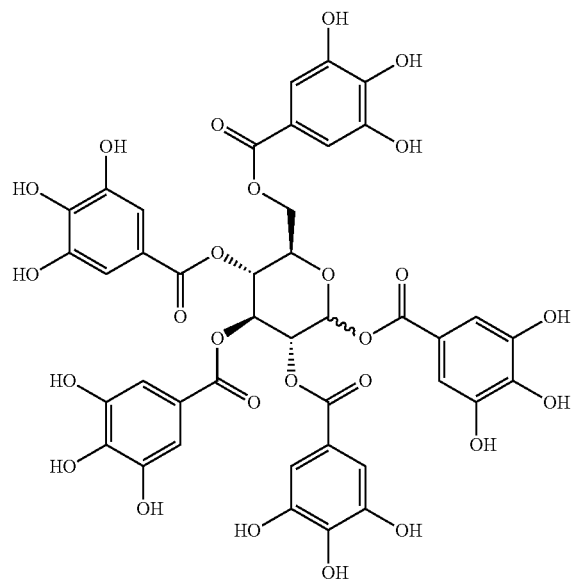 [SMILES: O=C(OC[C@H]1OC(OC(=O)c2cc(O)c(O)c(O)c2)[C@H](OC(=O)c2cc(O)c(O)c(O)c2)[C@@H](OC(=O)c2cc(O)c(O)c(O)c2)[C@@H]1OC(=O)c1cc(O)c(O)c(O)c1)c1cc(O)c(O)c(O)c1] |
| CDE-002 | (III) | 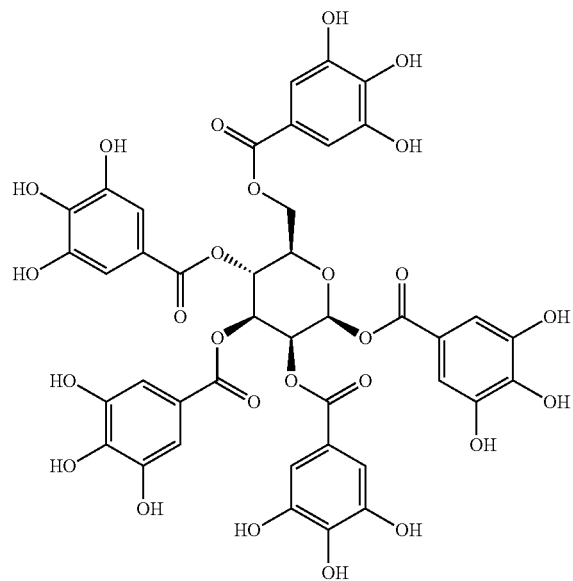 [SMILES: O=C(OC[C@H]1O[C@@H](OC(=O)c2cc(O)c(O)c(O)c2)[C@@H](OC(=O)c2cc(O)c(O)c(O)c2)[C@@H](OC(=O)c2cc(O)c(O)c(O)c2)[C@@H]1OC(=O)c1cc(O)c(O)c(O)c1)c1cc(O)c(O)c(O)c1] |

TABLE 1-continued
Synthesized PAI-1 Inhibitor Compounds
| CDE No. | Formula No. | Structure |
|---|---|---|
| CDE-003 | (IV) | 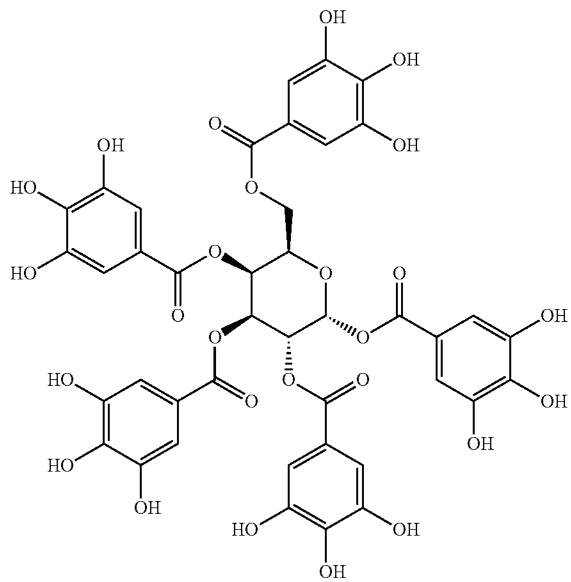 [SMILES: O=C(OC[C@H]1O[C@H](OC(=O)c2cc(O)c(O)c(O)c2)[C@H](OC(=O)c2cc(O)c(O)c(O)c2)[C@@H](OC(=O)c2cc(O)c(O)c(O)c2)[C@H]1OC(=O)c1cc(O)c(O)c(O)c1)c1cc(O)c(O)c(O)c1] |
| CDE-004 | (V) | 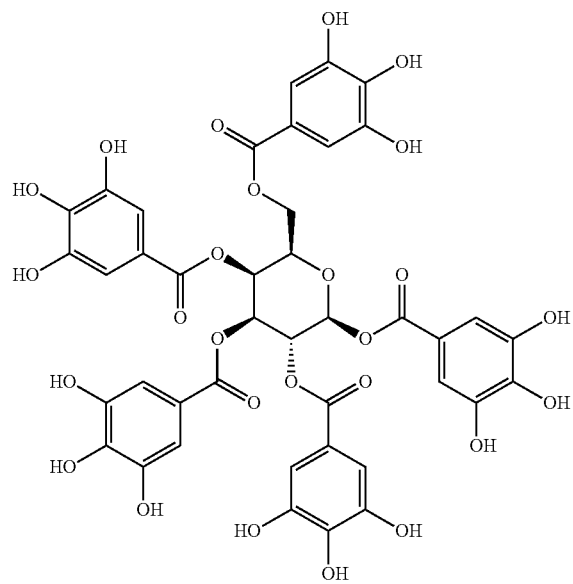 [SMILES: O=C(OC[C@H]1O[C@@H](OC(=O)c2cc(O)c(O)c(O)c2)[C@H](OC(=O)c2cc(O)c(O)c(O)c2)[C@@H](OC(=O)c2cc(O)c(O)c(O)c2)[C@H]1OC(=O)c1cc(O)c(O)c(O)c1)c1cc(O)c(O)c(O)c1] |

TABLE 1-continued
Synthesized PAI-1 Inhibitor Compounds
| CDE No. | Formula No. | Structure |
|---|---|---|
| CDE-006 | (VI) | 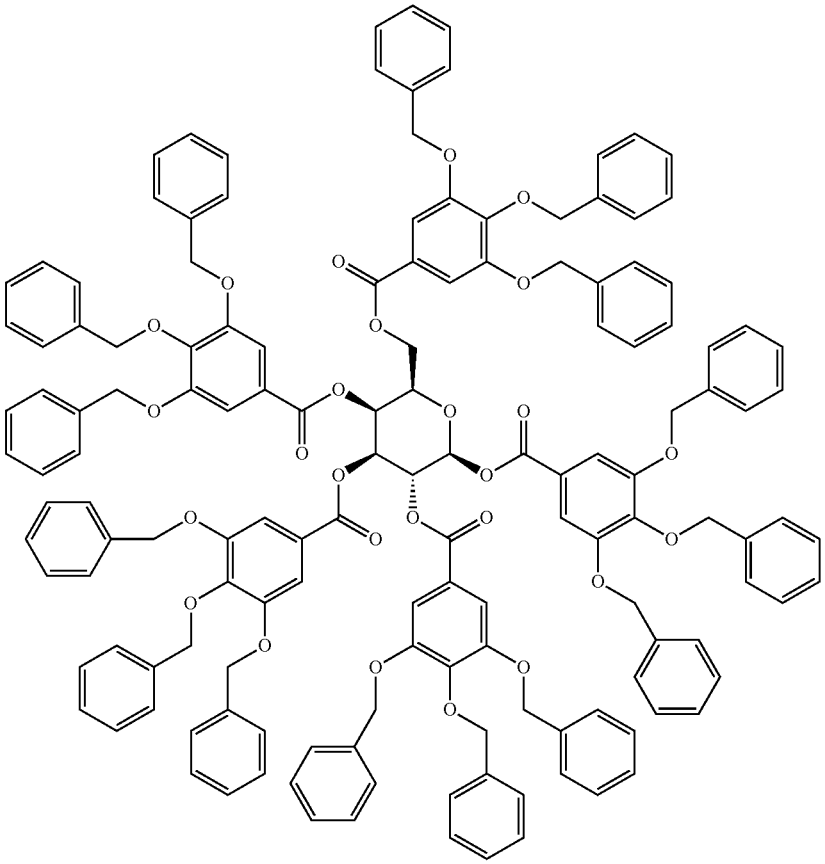 [SMILES: O=C(OC[C@H]1O[C@@H](OC(=O)c2cc(OCc3ccccc3)c(OCc3ccccc3)c(OCc3ccccc3)c2)[C@H](OC(=O)c2cc(OCc3ccccc3)c(OCc3ccccc3)c(OCc3ccccc3)c2)[C@@H](OC(=O)c2cc(OCc3ccccc3)c(OCc3ccccc3)c(OCc3ccccc3)c2)[C@H]1OC(=O)c1cc(OCc2ccccc2)c(OCc2ccccc2)c(OCc2ccccc2)c1)c1cc(OCc2ccccc2)c(OCc2ccccc2)c(OCc2ccccc2)c1] |

TABLE 1-continued
Synthesized PAI-1 Inhibitor Compounds
| CDE No. | Formula No. | Structure |
|---|---|---|
| CDE-007 | (VII) | 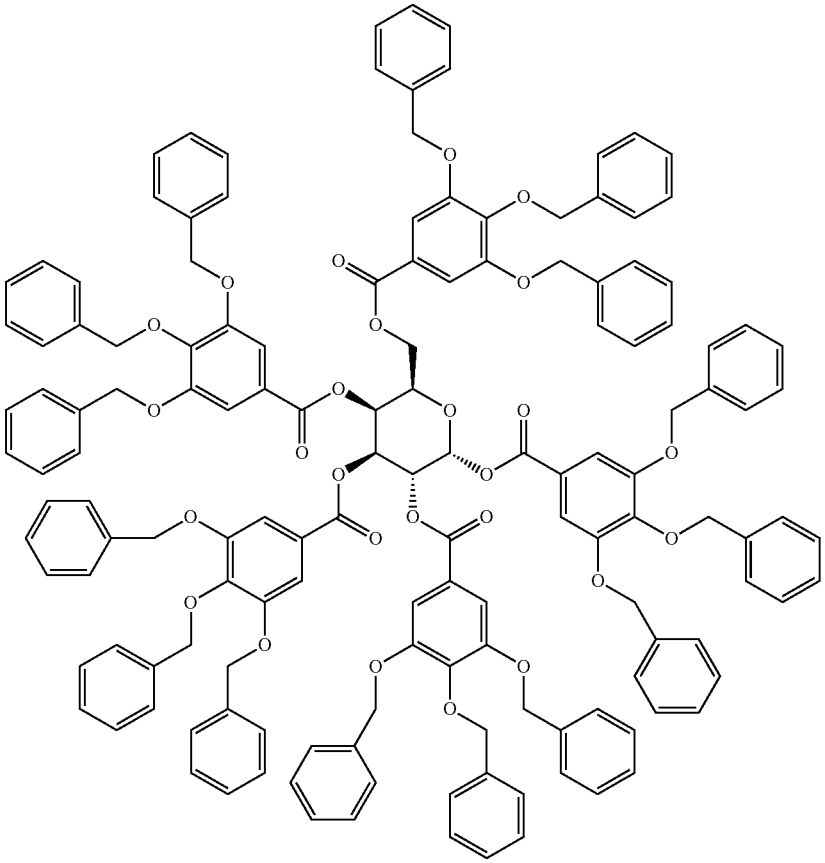 [SMILES: O=C(OC[C@H]1O[C@H](OC(=O)c2cc(OCc3ccccc3)c(OCc3ccccc3)c(OCc3ccccc3)c2)[C@H](OC(=O)c2cc(OCc3ccccc3)c(OCc3ccccc3)c(OCc3ccccc3)c2)[C@@H](OC(=O)c2cc(OCc3ccccc3)c(OCc3ccccc3)c(OCc3ccccc3)c2)[C@H]1OC(=O)c1cc(OCc2ccccc2)c(OCc2ccccc2)c(OCc2ccccc2)c1)c1cc(OCc2ccccc2)c(OCc2ccccc2)c(OCc2ccccc2)c1] |
|  | (VIII) | 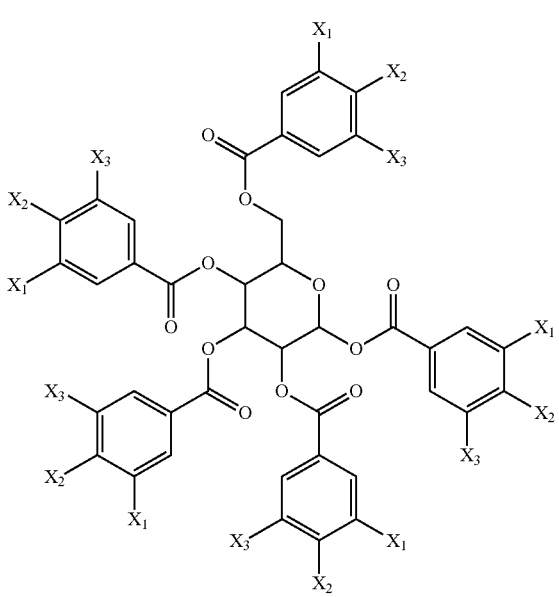 |

TABLE 1-continued

Synthesized PAI-1 Inhibitor Compounds

| CDE No. | Formula No. | Structure |
|---|---|---|
|  | (IX) | Structure with HO-, X₃, X₄ substituted benzoate linked via –C(O)O–(CH₂CH₂O)ₙ–C(O)– to benzene ring with OH, X₁, X₂ |
|  | (XXVIII) | Bis(3,4,5-trihydroxybenzoate) linked by –(OCH₂CH₂)ₙ– |
| CDE-008 | (X) | Ethylene glycol bis(3,4,5-trihydroxybenzoate) |
| CDE-009 | (XI) | Diethylene glycol bis(3,4,5-trihydroxybenzoate) |
| CDE-010 and CDE-012 | (XII) | Triethylene glycol bis(3,4,5-trihydroxybenzoate) |
| CDE-011 | (XIII) | Tetraethylene glycol bis(3,4,5-trihydroxybenzoate) |

TABLE 1-continued

Synthesized PAI-1 Inhibitor Compounds

| CDE No. | Formula No. | Structure |
|---|---|---|
| | (XIV) | |
| | (XIV) | |
| | (XV) | |
| CDE-013 | (XVI) | 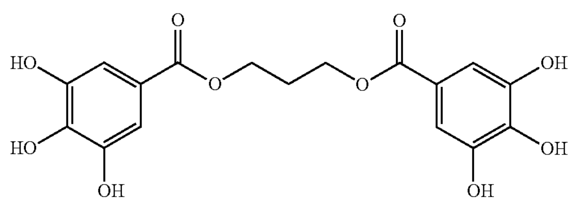 [SMILES: O=C(OCCCOC(=O)c1cc(O)c(O)c(O)c1)c1cc(O)c(O)c(O)c1] |
| | (XVII) | |
| CDE-028 | (XVIII) | 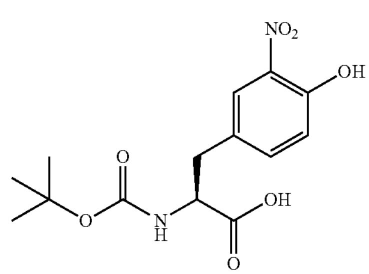 [SMILES: CC(C)(C)OC(=O)N[C@@H](Cc1ccc(O)c([N+](=O)[O-])c1)C(=O)O] |

TABLE 1-continued
Synthesized PAI-1 Inhibitor Compounds
| CDE No. | Formula No. | Structure |
|---|---|---|
| | (XIX) | 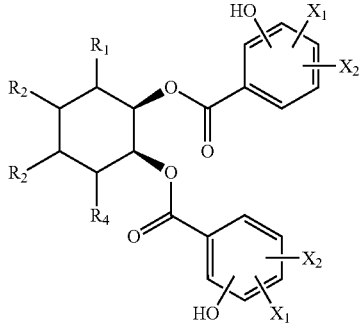 |
| | (XX) | 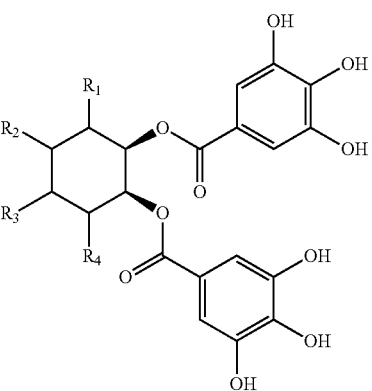 |
| CDE-031 | (XXI) | 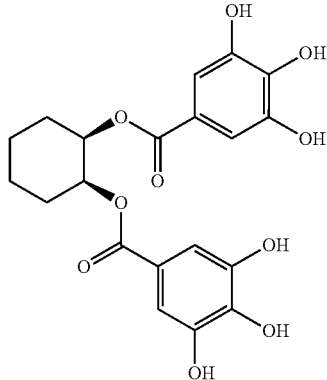 [SMILES: O=C(O[C@H]1CCCC[C@H]1OC(=O)c1cc(O)c(O)c(O)c1)c1cc(O)c(O)c(O)c1] |
| | (XXII) | 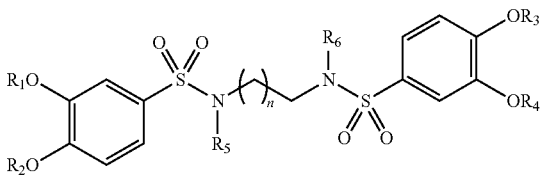 |
| CDE-021 | (XXIII) | 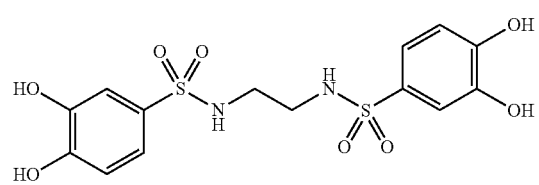 [SMILES: O=S(=O)(NCCNS(=O)(=O)c1ccc(O)c(O)c1)c1ccc(O)c(O)c1] |

TABLE 1-continued

Synthesized PAI-1 Inhibitor Compounds

| CDE No. | Formula No. | Structure |
|---|---|---|
| CDE-029 | (XXIV) | 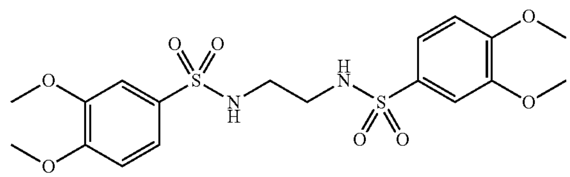 |
| CDE-030 | (XXV) | 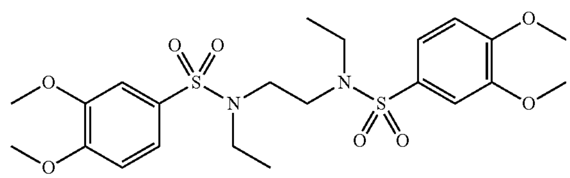 |
| CDE-032 | (XXVI) | 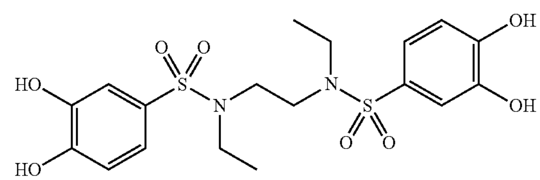 [SMILES: CCN(CCN(CC)S(=O)(=O)c1ccc(O)c(O)c1)S(=O)(=O)c1ccc(O)c(O)c1] |
| | (XXVII) | |
| | (XXIX) | |
| | (XXX) | |

TABLE 1-continued

Synthesized PAI-1 Inhibitor Compounds

| CDE No. | Formula No. | Structure |
|---|---|---|
| | (XXXI) | |
| | (XXXII) | |
| | (XXXIII) | |
| | (XXXIV) | |

Methods of Making Inhibitors of PAI-1 Activity

The compounds of the present invention can be readily prepared according to the following reaction schemes or modification thereof using readily available starting materials, reagents and conventional synthetic procedures. It is also possible to make use of variants of these process steps, which in themselves are known to and well within the preparatory skill of the medicinal chemist.

Derivatives of PAI-1 inhibitor are also included herein. Such derivatives include molecules modified by one or more water soluble polymer molecules, such as polyethylene glycol, or by the addition of polyamino acids, including fusion proteins (procedures for which are well-known in the art). Such derivatization may occur singularly or there may be multiple sites of derivatization.

Primary Screen for the PAI-1 Inhibition

The ability of the compounds of the invention to inhibit PAI-1 was established herein. Such methods of screening compounds and testing for PAI-1 inhibition are described in the Examples. In addition, other methods of screening for PAI-1 inhibition are known in the art. Such methods are set out herein below. These methods should not be construed as limiting because any methods known in the art are contemplated for use in the invention.

For example, U.S. Pat. No. 7,351,730 describes a method of screening for PAI-1 inhibition wherein test compounds are dissolved in DMSO at a final concentration of 10 mM, then diluted 100× in physiologic buffer. The inhibitory assay is initiated by the addition of test compound (1-100 μM final concentration, maximum DMSO concentration of 0.2%) in a pH 6.6 buffer containing 140 nM recombinant human plasminogen activator inhibitor-1 (PAI-1; Molecular Innovations, Royal Oak, Mich.). Following a 1 hour incubation at room temperature, 70 nM of recombinant human tissue plasminogen activator (tPA) is added, and the combination of test compound, PAI-1 and tPA is incubated for an additional 30 minutes. Following the second incubation, Spectrozyme-tPA (American Diagnostica, Greenwich, Conn.), a chromogenic substrate for tPA, is added and absorbance read at 405 nm at 0 and 60 minutes. Relative PAI-1 inhibition is equal to the residual tPA activity in the presence of test compound and PAI-1. Control treatments include the complete inhibition of tPA by PAI-1 at the molar ratio employed (2:1), and the absence of any effect of the test compound on tPA alone.

Assay for Determining $IC_{50}$ of Inhibition of PAI-1

In addition to the assays described in the Examples, another assay for determining PAI-1 inhibition is also described in U.S. Pat. No. 7,351,730. Briefly, assay plates are initially coated with human tPA (10 μM/ml). Test compounds are dissolved in DMSO at 10 mM, then diluted with physiologic buffer (pH 7.5) to a final concentration of 1-50 μM.

Test compounds are incubated with human PAI-1 (50 ng/ml) for 15 minutes at room temperature. The tPA-coated plate is washed with a solution of 0.05% Tween 20 and 0.1% BSA, then the plate is blocked with a solution of 3% BSA. An aliquot of the test compound/PAI-1 solution is then added to the tPA-coated plate, incubated at room temperature for 1 hour, and washed. Active PAI-1 bound to the plate is assessed by adding an aliquot of a 1:1000 dilution of the 33B8 monoclonal antibody against human PAI-1, and incubating the plate at room temperature for 1 hour (Molecular Innovations, Royal Oak, Mich.). The plate is again washed, and a solution of goat anti-mouse IgG-alkaline phosphatase conjugate is added at a 1:50,000 dilution in goat serum. The plate is incubated 30 minutes at room temperature, washed, and a solution of alkaline phosphatase substrate is added. The plate is incubated 45 minutes at room temperature, and color development is determined at $OD_{405}$ nm. The quantitation of active PAI-1 bound to tPA at varying concentrations of test compound is used to determine the $IC_{50}$. The $IC_{50}$ is the half maximal (50%) inhibitory concentration (IC) of a substance (50% IC, or $IC_{50}$). Results are then analyzed using a logarithmic best-fit equation. The assay sensitivity is 5 ng/ml of human PAI-1 as determined from a standard curve ranging from 0-100 ng/ml.

Methods of Using PAI-1 Inhibitors

As mentioned herein above, it is contemplated that methods of the invention include increasing circulating HDL and/or decreasing circulating VLDL in a subject comprising administering a PAI-1 inhibitor. In one aspect, the subject is a mammal. In a preferred aspect, the mammalian subject is human.

It is contemplated that such PAI-1 inhibitor compounds and methods are useful in the treatment of acute diseases associated with high PAI-1 levels, such as, but not limited to, sepsis and myocardial infarction, compared to PAI-1 levels in normal subjects known not to suffer from sepsis or myocardial infarction. In addition, it is contemplated that such PAI-1 inhibitor compounds and methods are useful in the treatment of chronic diseases and conditions associated with high PAI-1 levels, such as, but not limited to, cancer, atherosclerosis, insulin resistance, and type 2 diabetes, to PAI-1 levels in normal subjects known not to suffer from these diseases or conditions. A PAI-1 inhibitor is contemplated to be useful in the treatment of any condition wherein the lowering of PAI-1 levels will provide benefits. The PAI-1 inhibitor is useful alone, or in combination with other compounds, which may act as to promote the reduction of PAI-1 levels. The present section provides a description of how the PAI-1 inhibitors of the invention may be therapeutically administered to a subject in need thereof.

One of the therapeutic embodiments of the invention is the provision, to a subject in need thereof, compositions comprising one or more PAI-1 inhibitor. In one aspect, the PAI-1 inhibitor is isolated from a known compound or is chemically synthesized. In another aspect, the PAI-1 inhibitor formulations for therapy in a subject is selected based on the route of administration and in certain aspects includes liposome and micelle formulations as well as classic pharmaceutical preparations.

The PAI-1 inhibitor is formulated into an appropriate preparation and administered to one or more sites within the subject in a therapeutically effective amount. In one embodiment, the PAI-1 inhibitor-based therapy is effected via continuous or intermittent intravenous administration. In one aspect, the PAI-1 inhibitor-based therapy is effected via continuous or intermittent intramuscular or subcutaneous administration. In another aspect, the PAI inhibitor-based therapy is effected via oral or buccal administration. By "effective amount" the invention refers to an amount of PAI-1 inhibitor compound that is sufficient to support an observable change in the level of one or more biological activities of PAI-1, HDL, LDL, or VLDL and/or an observable change in an indication for which the method of treatment is intended. The change may be reduced level of PAI-1 activity. In one aspect, the change is an increase in HDL and/or a reduction in LDL and VLDL.

In various aspects, administration of the compositions is systemic or local, and in still other aspects comprises a single site injection of a therapeutically-effective amount of the PAI-1 inhibitor composition. Any route known to those of skill in the art for the administration of a therapeutic composition of the invention is contemplated including, for example, intravenous, intramuscular, subcutaneous, oral, or a catheter for long-term administration.

Alternatively, it is contemplated that the therapeutic composition is delivered to the patient at multiple sites. The multiple administrations is rendered simultaneously or is administered over a period of several hours. It is likewise contemplated that the therapeutic composition is taken on a regular basis via oral administration. In certain cases, it is beneficial to provide a continuous flow of the therapeutic composition. Additional therapy is administered on a period basis, for example, daily, weekly, or monthly.

In addition to therapies based solely on the delivery of the PAI-1 inhibitor composition, combination therapy is specifically contemplated. In the context of the invention, it is contemplated that the PAI-1 inhibitor composition therapy is used similarly in conjunction with other agents commonly used for the treatment of elevated levels of PAI-1, LDL and VLDL.

To achieve the appropriate therapeutic outcome, using the methods and compositions of the invention, one would generally provide a composition comprising a PAI-1 inhibitor and at least one other therapeutic agent (second therapeutic agent). In one aspect of the invention, it is contemplated that methods include administration or inclusion of at least one additional factor or other drug. Such drugs include drugs used to manage cardiovascular disease including, but not limited to, cholesterol lowering drugs, such as statins, anti-inflammatories, and ACE inhibitors. Such drugs also include drugs targeting neurological disorders including, but not limited to drugs for targeting stroke, seizures, and Alzheimer's Disease. In another aspect, the additional drugs include, but are not limited to, drugs targeting diabetes. These are all disorders associated with elevated levels of PAI-1 and, therefore, it is contemplated that combination therapy may be used with PAI-1 inhibitors and other known therapies.

The combination therapy compositions are provided in a combined amount effective to produce the desired therapeutic outcome in the treatment of increased levels of PAI-1, VLDL, or LDL and/or make a detectable change in an indication as described herein. This process involves administering the PAI-1 inhibitor and the second agent(s) or factor(s) at the same time. Methods thus include administering a single composition or pharmacological formulation that includes both agents, or administering two distinct compositions or formulations, at the same time, wherein one composition includes the PAI-1 inhibitor therapeutic composition and the other includes the second therapeutic agent.

Alternatively, the PAI-1 inhibitor treatment precedes or follows the second therapeutic agent treatment by intervals ranging from minutes to weeks. In embodiments where the second therapeutic agent and the PAI-1 inhibitor are administered separately, one generally ensures that a significant period of time did not expire between the times of each delivery, such that the second therapeutic agent and the PAI-1 inhibitor are able to exert an advantageously combined effect. In such instances, it is contemplated that one administers both modalities within about 12-24 hours of each other, or alternately, within about 6-12 hours of each other, or alternately, with a delay time of only about 12 hours. In some situations, it is desirable to extend the time period for treatment significantly, however, where several days (2, 3, 4, 5, 6 or 7) to several weeks (1, 2, 3, 4, 5, 6, 7 or 8) lapse between the respective administrations.

Systemic delivery of PAI-1 inhibitors to patients is a very efficient method for delivering a therapeutically effective amount of the compound to counteract the immediate clinical manifestations of a disease. Alternatively, local delivery of the PAI-1 inhibitor and/or the second therapeutic agent is appropriate in certain circumstances. In a certain embodiment, it is contemplated that the PAI-1 inhibitor is delivered to a patient for an extended period of time. It is further contemplated that the PAI-1 inhibitor is taken throughout a patient's lifetime to lower PAI-1, VLDL and/or LDL levels.

Pharmaceutical Compositions

As mentioned herein above, the invention also comprehends methods using pharmaceutical compositions comprising effective amounts of PAI-1 inhibitor together with pharmaceutically acceptable diluents, preservatives, solubilizers, emulsifiers, adjuvants and/or carriers useful in PAI-1 inhibitor therapy. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., thimersol, benzyl alcohol), and bulking substances (e.g., lactose, mannitol); incorporation of the material into particulate preparations of polymeric compounds, such as polylactic acid, polyglycolic acid, etc., or in association with liposomes or micelles. Such compositions will influence the physical state, stability, rate of in vivo release, and rate of in vivo clearance of the PAI-1 inhibitor. See, e.g., Remington's Pharmaceutical Sciences, 18th Ed. (1990) Mack Publishing Co., Easton, Pa., pages 1435-1712, which are herein incorporated by reference.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. In one aspect, the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions, which are sterile solutions or suspensions, can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physician's direction. For example, unit dosages may be made up in packeted powders, vials or ampoules and, in one aspect, in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patient's recovery rate.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, and, in one aspect, orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

PAI-1 inhibitors or derivatives thereof may be formulated for injection, or oral, nasal, pulmonary, topical, or other types of administration as one skilled in the art will recognize. The formulation may be liquid or may be solid, such as lyophilized, for reconstitution.

PAI-1 inhibitor or derivatives thereof are useful in the treatment of any of the acute or chronic diseases associated with increased levels of PAI-1, LDL, or VLDL. Thus, the present methods may be useful for the treatment of such conditions. Conditions alleviated or modulated by the administration of PAI-1 inhibitor are typically those characterized by increased levels of VLDL and LDL. Such conditions may be induced as a course of therapy for other purposes, such as chemotherapy or radiation therapy. It is contemplated that such conditions may result from genetic inheritance or be the side effect of another condition or medication.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the vectors or cells of the invention, its use in therapeutic compositions is contemplated. Supplementary active ingredients also can be incorporated into the compositions.

The active compositions used in the methods of the invention include classic pharmaceutical preparations. Administration of these compositions according to the invention will be via any common route so long as the target tissue is available via that route. The pharmaceutical compositions may be introduced into the subject by any conventional method, e.g., by intravenous, intradermal, intramusclar, intramammary, intraperitoneal, intrathecal, retrobulbar, intrapulmonary (e.g., term release); by oral, sublingual, nasal, anal, vaginal, or transdermal delivery, or by surgical implantation at a particular site. The treatment may consist of a single dose or a plurality of doses over a period of time.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents (for example, sugars or sodium chloride). Prolonged absorption of the injectable compositions can be brought about by the use in the compositions of agents delaying absorption (for example, aluminum monostearate and gelatin).

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients also can be incorporated into the compositions.

For oral administration of the compositions used in the methods of the invention, a PAI-1 inhibitor may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions used in the methods of the invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

Generally, an effective amount of a PAI-1 inhibitor, or derivatives thereof, will be determined by the age, weight, and condition or severity of disease of the recipient. See, Remington's Pharmaceutical Sciences, supra, pages 697-773, herein incorporated by reference. Typically, a dosage of between about 0.001 µg/kg body weight/day to about 1000 µg/kg body weight/day, may be used, but more or less, as a skilled practitioner will recognize, may be used. Dosing may be one or more times daily, or less frequently, and may be in conjunction with other compositions as described herein. It should be noted that the invention is not limited to the dosages recited herein.

By initiating the treatment regimen with a minimal daily dose of about one gram, the blood levels of PAI-1 and the patient's symptomatic relief analysis may be used to determine whether a larger dose is indicated. One skilled in the art will appreciate that the appropriate dosage levels for treatment will thus vary depending, in part, upon the molecule delivered, the indication for which the PAI-1 inhibitor compound is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

"Unit dose" is defined as a discrete amount of a therapeutic composition dispersed in a suitable carrier. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See, for example, Remington's Pharmaceutical Sciences, supra, pages 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

Appropriate dosages may be ascertained through the use of established assays for determining level of myocardial infarct in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment.

It will be appreciated that the pharmaceutical compositions and treatment methods of the invention are useful in fields of human medicine and veterinary medicine. Thus the subject to be treated is in one aspect a mammal. In another aspect, the mammal is a human.

In addition, the invention contemplates a kit containing components comprising a composition comprising a PAI-1 inhibitor; and optionally, at least one additional factor useful in the treatment of the acute and chronic diseases and conditions discussed herein.

Lipoproteins, Cholesterol, and Lipid Metabolism

The invention includes the use of PAI-1 compounds to modulate lipid metabolism and treat high cholesterol associated with an increased level of PAI-1. Therefore, the present section provides a brief summary of what is known about cholesterol and cholesterol regulation in the body to the extent that such a summary will facilitate a better understanding of the compounds and methods of the present invention.

Very-low-density lipoprotein (VLDL) cholesterol is one of the three major types of blood cholesterol combined with protein. The other two are high-density lipoprotein (HDL) cholesterol and low-density lipoprotein (LDL) cholesterol. Each type contains a specific combination of cholesterol, protein and triglyceride, a blood fat. VLDL cholesterol contains the highest amount of triglyceride.

VLDL is assembled in the liver from cholesterol and apolipoproteins and is converted in the bloodstream to LDL. VLDL particles have a diameter of 30-80 nm. VLDL transports endogenous triglycerides, phospholipids, cholesterol and cholesteryl esters, and functions as the body's internal transport mechanism for lipids. VLDL cholesterol is often referred to as "bad" cholesterol because elevated levels are associated with an increased risk of coronary artery disease and have been correlated with accelerated rates of atherosclerosis. There is no simple, direct way to measure VLDL cholesterol, so it is usually calculated as a percentage of triglyceride levels. As triglyceride levels are reduced, so are VLDL levels. Foods that are high in glycemic index tend to stimulate VLDL cholesterol production.

The VLDL receptor (VLDL-R) is a lipoprotein receptor that shows considerable similarity to the low-density-lipoprotein receptor (LDL-R). VLDL-R binds apolipoprotein E (ApoE) but not ApoB, and is expressed in fatty acid active tissues (heart, muscle, adipose) and macrophages abundantly. Lipoprotein lipase (LPL) modulates the binding of triglyceride (TG)-rich lipoprotein particles to VLDL-R and, in contrast to LDL-R, VLDL-R expression is not down-regulated by lipoproteins (Takahashi et al., Molec. & Cell. Biochem. 248: 121-127, 2003).

HDL cholesterol is often referred to as "good" cholesterol because it helps the body get rid of "bad" LDL cholesterol by carrying it back to the liver, where it can be recycled or incorporated into the bile and eventually excreted from the body. This mechanism is how HDL may help prevent cholesterol from building up in the arteries. The observation, as described herein, that both genetic and pharmacologic reduction of PAI-1 increases plasma HDL levels suggests that one potential lipid metabolic pathway where PAI-1 may play a role is reverse cholesterol transport (RCT).

RCT is a pathway by which accumulated cholesterol is transported from the vessel wall to the liver for excretion, thus preventing atherosclerosis. Major constituents of RCT include acceptors such as high-density lipoprotein (HDL) and apolipoprotein A-I (apoA-I), and enzymes such as lecithin: cholesterol acyltransferase (LCAT), phospholipid transfer protein (PLTP), hepatic lipase (HL) and cholesterol ester transfer protein (CETP) (Ohashi et al., Q. J. Med. 98:845-856, 2005). A critical part of RCT is cholesterol efflux, in which accumulated cholesterol is removed from macrophages in the subintima of the vessel wall by ATP-binding membrane cassette transporter A1 (ABCA1) or by other mechanisms, including passive diffusion, scavenger receptor B1 (SR-B1), caveolins and sterol 27-hydroxylase, and collected by HDL and apoA-I (Ohashi et al., supra). Esterified cholesterol in the HDL is then delivered to the liver for excretion.

Levels of HDL are inversely correlated with incidences of cardiovascular disease. Supplementation with HDL or apoA-I can reverse atherosclerosis by accelerating RCT and cholesterol efflux (Ohashi et al., supra). RCT and cholesterol efflux play a major role in anti-atherogenesis, and modification of these processes may provide new therapeutic approaches to cardiovascular disease.

Furthermore, the inverse relationship between PAI-1 and HDL is similar to the inverse relationship between PAI-1 and vascular health, i.e., higher PAI-1 levels are associated with cardiovascular disease, whereas mice lacking PAI-1 are protected from the development of atherosclerosis (Vaughan, J. Thromb. Haemost. 3:1879-1883, 2005). Therefore, PAI-1 may play a role in the regulation of RCT.

In obesity and atherosclerosis, two cell types that are thought to have reduced RCT and, therefore, retain cholesterol, are macrophages and adipocytes. Remarkably, both macrophages and adipose tissue are also two primary sources of PAI-1 synthesis in obesity and atherosclerosis (Alessi et al., Diabetes 46:860-867, 1997; Lundgren et al., Circulation 93:106-110, 1996; Renckens et al., J. Thromb. Haemost. 3:1018-1025, 2005). Macrophages are particularly important in the development of vascular disease since inflammation plays a critical role in atherogenesis (Ross, N. Engl. J. Med. 340:115-126, 1999). During the development of atherosclerosis, monocytes are thought to enter the vascular wall in response to inflammatory stimuli where they accumulate as macrophages and avidly take up modified lipoproteins to become fat-laden cells referred to as foam cells. Foam cells in-turn are thought to express growth factors that promote smooth muscle cell proliferation, proteases that promote matrix remodeling and cytokines that promote further inflammation (Ross, supra). Thus, the association of high PAI-1 levels with vascular disease, along with the inverse correlations between PAI-1 levels and plasma HDL, and between increased PAI-1 synthesis and reduced RCT in macrophages and adipocytes led to the hypothesis that PAI-1 regulates HDL and VLDL interactions with macrophages and/or adipocytes, which leads to lower levels of plasma HDL and reduced RCT.

Like VLDL cholesterol, LDL cholesterol is considered "bad" cholesterol. LDL cholesterol belongs to the lipoprotein particle family. LDL is approximately 22 nm and its mass is about 3 million daltons; but, because LDL particles contain a changing number of fatty acids, they actually have a mass and size distribution. Each native LDL particle contains a single ApoB-100 molecule (a protein with 4536 amino acid residues) that circles the fatty acids, keeping them soluble in the aqueous environment. In addition, LDL has a highly hydrophobic core consisting of a polyunsaturated fatty acid known as linoleate and about 1500 esterified cholesterol molecules. This core is surrounded by a shell of phospholipids and unesterified cholesterol as well as a single copy of B-100 large protein (514 kDa). LDL transports cholesterol and triglycerides from the liver to peripheral tissues and regulates cholesterol synthesis at these sites.

When a cell requires cholesterol, the cell synthesizes the necessary LDL receptors (LDL-R), and inserts them into the plasma membrane. LDL-R diffuse freely until they associate with clathrin-coated pits. LDL particles in the blood stream bind to these extracellular LDL-R. The clathrin-coated pits then form vesicles that are endocytosed into the cell. After the clathrin coat is shed, the vesicles deliver the LDL and LDL-R to early endosomes, onto late endosomes to lysosomes. Here the cholesterol esters in the LDL are hydrolysed. LDL-R are recycled back to the plasma membrane.

Because a reduction or complete ablation of PAI-1 in vivo results in increased HDL plasma levels, it was hypothesized that one potential lipid metabolic pathway where PAI-1 may be acting is in the regulation of reverse cholesterol transport (RCT). RCT removes cholesterol from the peripheral tissues via HDL and delivers it to the liver. This process is necessary to maintain steady-state cholesterol homeostasis, and the relationship between reduced RCT and atherosclerosis is well established (Cuchel et al., Circ., 113:2548-2555, 2006).

In obesity and atherosclerosis, two cell types that are thought to have reduced RCT and thus retain cholesterol, are macrophages and adipocytes. Remarkably, both macrophages and adipose tissue are also two primary sources of PAI-1 synthesis in obesity and atherosclerosis (Alessi et al., Diabetes, 46:860-867, 1997; Lundgren et al., Circ., 93:106-110, 1996; Renckens et al., J. Thromb. Haemost., 3:1018-1025, 2005). Macrophages are particularly important in the development of vascular disease since inflammation plays a critical role in atherogenesis (Ross, N. Engl. J. Med., 340:115-126, 1999). During the development of atherosclerosis, monocytes are thought to enter the vascular wall in response to inflammatory stimuli where they accumulate as macrophages and avidly take up modified lipoproteins to become fat-laden cells referred to as foam cells. Foam cells in-turn are thought to express growth factors that promote smooth muscle cell proliferation, proteases that promote matrix remodeling and cytokines that promote further inflammation (Ross, supra). Taken together, the association of high PAI-1 levels with vascular disease, along with the inverse correlations between PAI-1 levels and plasma HDL, and between increased PAI-1 synthesis and RCT in macrophages and adipocytes suggests that PAI-1 regulates HDL and VLDL interactions with macrophages and/or adipocytes, which in turn leads to lower levels of plasma HDL and reduced RCT. Thus, the studies described herein identify and characterized the specific molecular interactions between PAI-1 and lipoproteins and/or cells involved in RCT.

In addition, the inverse relationship between PAI-1 and HDL is similar to the inverse relationship between PAI-1 and vascular health, i.e., higher levels of PAI-1 are associated with cardiovascular disease, whereas mice lacking PAI-1 are protected from the development of atherosclerosis (Vaughan et al., J. Thromb. Haemost. 3:1879-1883, 2005).

Thus, the invention includes the characterization of specific molecular interactions between PAI-1 and lipoprotein particles or cells involved in RCT, including, but not limited to, examination of the binding of PAI-1 to different protein components of the VLDL and HDL lipoprotein particles, including ApoA-I and ApoE, measuring the ability of PAI-1 to modulate HDL and VLDL binding to different receptors and enzymes involved in lipid metabolism, and characterizing the effects of PAI-1 on HDL and VLDL uptake by macrophages and adipocytes. In addition, lipid metabolism was examined in mice with different factors of the PA-system either knocked-out, or with specific PAI-1 knock-in mutations that ablate single PAI-1 functions.

Uses of Compounds of the Invention in the Treatment of Disease

The invention includes the use of compounds of the invention for the production of a medicament for the treatment or prevention of any condition or disease discussed herein.

The compounds of the invention are inhibitors of the serine protease inhibitor PAI-1, and are therefore useful in the treatment or prophylaxis of those processes which involve the production and/or action of PAI-1. Thus, the compounds of the invention are useful in the regulation of lipid metabolism as described herein. In one aspect, the compounds of the invention are useful in treating high cholesterol and diseases associated with elevated levels of PAI-1. In another aspect, the compounds of the invention are useful in treating elevated levels of VLDL or LDL. In another aspect, the compounds of the invention are useful in elevating HDL.

In one aspect, the invention includes the uses of these inhibitors for the treatment of many conditions, diseases or disorders associated with PAI-1 activity. Such conditions or disorders include, but are not limited to, inflammation, cell migration and migration-driven proliferation of cells, and angiogenesis or thrombosis. Such inhibitors are also contemplated to be useful for modulation of endogenous fibrinolysis, and in conjunction with pharmacologic thrombolysis.

The compounds of the invention are useful in the treatment or prevention of insulin resistance, obesity, non-insulin dependent diabetes mellitus, cardiovascular disease, thrombotic events associated with coronary artery and cerebrovascular disease. The compounds of the invention are also useful for inhibiting the disease process involving the thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary thrombosis, cerebral thrombosis, thromboembolic complications of surgery (such as joint replacement), and peripheral arterial occlusion. These compounds are also useful in treating stroke associated with or resulting from atrial fibrillation.

The compounds of the invention are also used in the treatment or prophylaxis of high cholesterol and diseases associated with such a condition.

The compounds of the invention may also be used in the treatment of diseases associated with extracellular matrix accumulation, including, but not limited to, renal fibrosis, chronic obstructive pulmonary disease, polycystic ovary syndrome, restenosis, renovascular disease and organ transplant rejection.

The compounds of the invention may also be used in the treatment of malignancies, and diseases associated with neoangiogenesis (such as diabetic retinopathy).

The compounds in the invention may also be used in conjunction with and following processes or procedures involving maintaining blood vessel patency, including vascular surgery, vascular graft and stent patency, organ, tissue and cell implantation and transplantation.

The compounds of the invention may also be used in the treatment of Alzheimer's disease. This method may also be characterized as the inhibition of plasminogen activator by PAI-1 in a mammal, particularly a human, experiencing or subject to Alzhemier's disease. This method may also be characterized as a method of increasing or normalizing levels of plasmin concentration in a mammal, particularly those experiencing or subject to Alzheimer's disease.

The compounds of the invention may be used for the treatment of myelofibrosis with myeloid metaplasia by regulating stromal cell hyperplasia and increases in extracellular matrix proteins.

The compounds of the invention may also be used in conjunction with protease inhibitor-containing highly active antiretroviral therapy (HAART) for the treatment of diseases which orginate from fibrinolytic impairment and hypercoagulability of HIV-1 infected patients receiving such therapy.

The compounds of the invention may be used for the treatment of diabetic nephropathy and renal dialysis associated with nephropathy.

The compounds of the invention may be used to treat cancer, septicemia, proliferative diseases such as psoriasis, improving coagulation homeostasis, cerebrovascular diseases, microvascular disease, hypertension, dementia, atherosclerosis, osteoporosis, arthritis, asthma, heart failure, arrhythmia, angina, and as a hormone replacement agent, treating, preventing or reversing progression of atherosclerosis, Alzheimer's disease, osteoporosis, osteopenia; reducing inflammatory markers, fibrinolytic disorder, reducing C-reactive protein, or preventing or treating low grade vascular inflammation, stroke, dementia, coronary heart disease, primary and secondary prevention of myocardial infarction, stable and unstable angina, primary prevention of coronary events, secondary prevention of cardiovascular events, peripheral vascular disease, peripheral arterial disease, acute vascular syndromes, deep vein thrombosis, pulmonary embolism, reducing the risk of undergoing a myocardial revascularization procedure, microvascular diseases such as nephropathy, neuropathy, retinopathy and nephrotic syndrome, hypertension, Type 1 and 2 diabetes and related diseases, obesity, insulin resistance, hyperglycemia, hyperinsulinemia, malignant lesions, premalignant lesions, gastrointestinal malignancies, liposarcomas and epithelial tumors, proliferative diseases such as psoriasis, improving coagulation homeostasis, and/or improving endothelial function, and all forms of cerebrovascular diseases.

The compounds of the invention may be used for the topical applications in wound healing for prevention of scarring.

The compounds in the invention can be used in the treatment of inflammatory diseases, septic shock and the vascular damage associated with infections and for the treatment of blood and blood products used in dialysis, blood storage in the fluid phase, especially ex vivo platelet aggregation. The compounds in the present invention may also be used in combination with prothrombolytic, fibrinolytic and anticoagulant agents. The present compounds may also be added to human plasma during the analysis of blood chemistry in hospital settings to determine the fibrinolytic capacity thereof.

This invention further comprises methods for treating, preventing, ameliorating or inhibiting each of the maladies mentioned herein in a mammal, in one aspect, in a human, the method(s) each comprising administering to a mammal in need of such treatment, prevention, amelioration or inhibition a pharmaceutically or therapeutically effective amount of a compound of this invention, or a pharmaceutically acceptable salt or ester form thereof.

The compounds of the present invention may also be used to treat cancer including, but not limited to, breast and ovarian cancer, and as imaging agents for the identification of metastatic cancers.

It will be understood that a pharmaceutically or therapeutically effective amount of a compound herein refers to an amount of the compound in question which will sufficiently inhibit the serine protease inhibitor PAI-1 in the mammal in need thereof to a sufficient extent to provide a desirable improvement in the condition in question or provide sufficient inhibition of the serine protease inhibitor PAI-1 to prevent, inhibit or limit the onset of the physiological basis for the malady or condition in question.

EXAMPLES

The invention is described in more detail with reference to the following non-limiting examples, which are offered to more fully illustrate the invention, but are not to be construed as limiting the scope thereof. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

PAI-1 is Involved in Lipid Metabolism

To determine whether PAI-1 is involved in lipid metabolism, plasma lipid profiles were compared between wild-type C57BL/6J mice, and PAI-1 null (PAI-1$^{-/-}$) C57BL/6J mice fed a standard mouse chow (#5001, Harlan Teklad, Indianapolis, Ind.). Citrated plasma was collected and analyzed for total cholesterol and triglycerides by enzymatic assay for individual lipoproteins by HPLC.

There was a highly significant increase in total cholesterol in mice lacking PAI-1 compared to the wild-type control mice on the same diet, with cholesterol rising an average of 38% in PAI-1 null mice, from 46 mg/dl to 63 mg/dl. This increase in cholesterol was primarily due to a significant increase in HDL, which increased from an average of 37 mg/dl in the wild-type mice to 49 mg/dl in the PAI-1 null mice. There was a modest but significant increase in LDL, and modest but not significant increases in VLRL and triglycerides in the PAI-1 null mice. Taken together, these data indicate that PAI-1 has a role in the regulation of normal lipid metabolism.

Example 2

The Identification of Novel High Affinity Small Molecule PAI-1 Inactivating Compounds Because the pharmacological inactivation of PAI-1 is a useful strategy for raising plasma HDL levels, the identification of compounds that inactivate PAI-1 is important for treating high cholesterol and understanding the mechanism of PAI-1 inactivation and the role of PAI-1 in lipid metabolism. As set out previously herein, PAI-039 (tiplaxtinin) has limitations as a PAI-1 inactivating compound. Specifically, its affinity for PAI-1 is relatively low (~10-20 µM), and PAI-039 does not inhibit vitronectin bound PAI-1. Therefore, methods for the identification of novel PAI-1 inactivating compounds were carried out.

These experiments were carried out at the High Throughput Screening (HTS) facility of the Center for Chemical Genomics (CCG) at the University of Michigan. The HTS facility allows high-throughput screening of chemical libraries, and currently has a compound collection of over 53,000 pure compounds as well as 1,300 natural product extracts available for screening. The HTS facility has carried out 14 screens to date using a range of assay formats and screening methodologies. Biochemical screens include either fluorometric or FRET detection of the activity of several proteases (furin and a viral protease), fluorescent guanine nucleotide binding, protein-protein interactions, and protein-DNA interactions.

The screen used in the invention was similar to the screen used to identify PAI-039 (Elokdah et al., J. Med. Chem. 47:3491-3494, 2004) and another PAI-1 inactivator (Crandall et al., J. Thromb. Haemost. 2:1422-1428, 2004), but with modifications to enhance the identification of compounds with greater binding affinity. In the screen used to identify PAI-039, a chromogenic assay was used and compound concentrations were 10-100 µM final concentration. PAI-1 was screened at 140 nM with 70 nM t-PA, and relative PAI-1 inhibitory activity was determined by the restoration of tPA activity. This 2:1 molar ratio of PAI-1 to tPA ensured that only drugs which inactivated more than 50% of the PAI-1 in the screen would be identified, thus enhancing the stringency of the screen.

The screen in the present experiments described herein likewise used a 2:1 molar ratio of PAI-1 to PA, but used uPA in place of tPA. Urokinase PA was chosen because uPA is significantly more active than tPA with low molecular weight substrates. Therefore, significantly lower concentrations of uPA and PAI-1 were needed in the screen. Lower concentrations of candidate compounds were then screened at a final concentration of 10 µM. These modifications improved the probability of identifying compounds that interact with PAI-1 with greater affinity than PAI-039.

Initially, the screening assay was carried out in a 96-well plate format. In the CCG Lab, it was adapted to 384-well plates for screening. Briefly, 10 µL of 100 nM recombinant active human PAI-1 was incubated for 15 min at room temperature, either with or without 10 µM of each candidate compound in a volume of 90 µL 10 mM HEPES, 150 mM NaCl and 0.005% Tween-20 buffer, pH 7.4, containing 1% DMSO. A 10 µL aliquot of 50 nM uPA solution was then added to each reaction well, and incubated for an additional 15 min at 37° C.

The proteolytic reactions were initiated by the addition of 100 µL of pGlu-Gly-Arg p-nitroanilide chromogenic uPA substrate (Sigma) to each reaction mixture. The kinetics of p-nitroanilide release in the course of peptide cleavage by uPA was monitored spectrophotometrically at 405 nm for 10 min with a microplate reader, and the residual inhibitory activity of PAI-1 after treatment was expressed as a percentage of initial activity of untreated PAI-1 (100%). Control treatments were carried out to ensure the complete inhibition of uPA by PAI-1 at the 2:1 molar ratio utilized, and also to insure the absence of any effect of the compounds on the uPA alone. PAI-039 was used as a positive control for PAI-1 inactivation.

After the screens were carried out, the data was uploaded to the CCG informatics system for hit picking and candidate compounds that elicited a 50% or greater reduction in PAI-1 activity were selected for further confirmation (this is equivalent to a 75% inhibition of PAI-1 because PAI-1 is screened at a 2:1 molar excess over uPA). Based on previous work with the CCG library, a hit-rate between 0.2 and 2% was expected. Hits were confirmed by dose response testing in duplicate. Priority for this dose-response confirmation step was given to compounds that have previously shown minimal activity in screens done against other targets. After $IC_{50}$ values were defined, the most potent hits were selected for further follow-up and synthetic optimization.

A positive hit is then tested for a higher affinity for PAI-1 than PAI-039 or for a lower $IC_{50}$ for PAI-1 than PAI-039. The stringency of the screen can be increased by switching to a fluorometric method of screening with the substrate Glutaryl-Gly-Arg-AMC (Bachem). This substrate is reported to react with pM concentrations of uPA (Butenas et al., Thromb. Haemost. 78:1193-1201, 1997) and thus, should permit the use of lower concentrations PAI-1 (down to 2 nM) and uPA (down to 1 nM), and lower concentrations of the candidate compounds (to 1 µM) in the screen. This sensitive method may also be particularly useful for screening the natural compound library that is available through the CCG as discussed herein. The CCG compound library contains fractionated extracts of microorganisms isolated from marine environments. Since each extract potentially contains many natural compounds, it is a possibility that a highly sensitive screen carried out with this library will have a greater potential to identify extracts containing high affinity but low abundance compounds.

After candidate compounds with significant activity against PAI-1 were identified, an initial round of synthetic optimization was carried out on the top four candidates. Concurrent with optimization, the mechanism of action of each parent compound was then characterized by the same techniques that were used for characterizing PAI-039. Each of the parent compounds was also tested in vivo for activity against PAI-1 protease inhibitor activity and for their ability to modulate lipid profiles in mice. These compounds of the invention are particularly useful for their ability to raise plasma HDL, and provide further insight into the mechanism of action of PAI-1 with lipid metabolic pathways.

Recombinant active human PAI-1 (final concentration 10 nM) was incubated for 60 minutes at room temperature either with or without 10 µM of each candidate compound (potential PAI-1 inhibitor) in a 384-well microtiter plate. Urokinase PA (final concentration 5 nM) was added to each reaction well and incubated for an additional 30 minutes at room temperature. Urokinase PA activity in each reaction mixture was determined with pGlu-Gly-Arg p-nitroanilide chromogenic substrate (final concentration 0.025 mM). The extent of p-nitroanilide release by uPA was measured spectrophotometrically at 405 nm after 60 minutes.

Compounds that inactivated PAI-1 were identified by the restoration of uPA activity following incubation of a compound with PAI-1. The extent of uPA restoration was determined by comparing each well containing candidate compound with wells containing untreated PAI-1 (100% PAI-1 activity) and to wells with uPA only (0% PAI-1 activity). The data were then uploaded to the CCG informatics system and positive hits were identified. A positive hit was determined to be any compound that increased uPA activity by more than 3 standard deviations above control wells with untreated PAI-1. From these data, a total of twenty-three candidate compounds were selected as positive hits from the initial screen. See Table 2.

TABLE 2

| Center for Chemical Genomics Compound Screen | | |
|---|---|---|
| Library | MS2000 | Natural Products |
| Screened | 2000 | 1500 |
| Hits | 23 | 30 |
| Hits after re-screen | 19 | 13 |
| Confirmed hits | 5 | 3 |

These hits were re-assayed by dose response testing in duplicate by the CCG and 19 of the 23 compounds were then obtained from the CCG for further analysis. Further analysis demonstrated that approximately half of the 19 compounds either had intrinsic absorbance at 405 nm or were largely insoluble in the buffer system (Assay Buffer: 10 mM HEPES, 150 mM NaCl, 0.005% Tween-20, +/−10% DMSO). Of the remaining compounds, five were found to directly inhibit complex formation between PAI-1 and uPA, confirming that these five compounds are specific PAI-1 inhibitors. Therefore, the system yielded a final confirmed rate of 0.25%.

Two of the candidate compounds identified as positive hits, tannic acid and epigallocatechin 3,5 digallate, surprisingly comprised related structures that both contained multiple galloyl units attached to different central cyclic core scaffolds. These compounds are both naturally-occurring polyphenolic compounds with reported antioxidant activity, and the similarities in their structures suggest the possibility of a structure:function relationship between gallic acid and PAI-1 inactivation.

Two additional compounds comprising gallic acid, epigallocatechin gallate (EGCG) and gallic acid, were also examined. The structures of the two originally identified compounds, tannic acid and epigallocatechin 3,5, digallate, along with the two related compounds, epigallocatechin gallate and gallic acid, together with the determined $IC_{50}$s against PAI-1 for each compound, are shown in FIG. 2.

Recombinant active human PAI-1 (final 3.5 nM) was incubated for 15 min at 23° C. with increasing concentrations of tannic acid. Urokinase PA (final 6 nM) was added to each reaction well and incubated for an additional 5 min at 37° C. Urokinase PA activity was determined with pGlu-Gly-Arg pNA chromogenic substrate (final 0.25 mM). The rate of release of the p-nitroanilide (pNA) group from the chromogenic substrate by uPA was measured at 405 nm for 15 min.

These data demonstrate that each of the galloyl containing compounds was able to inhibit PAI-1, but that the efficacy of this inhibition is dependent on either the number of galloyl units in each compound and/or its presentation in relationship to the other galloyl units. Thus, the monomeric gallic acid is approximately 1000-fold less active toward PAI-1 than is tannic acid which contains five terminal galloyl units (FIG. 2). Other data (not shown) indicate that the monomeric gallic acid may be up to 4000-fold less active toward PAI-1 than tannic acid.

In addition to recognizing this potential structure:function relationship with the gallic acid containing compounds, it was also surprising that in some experiments (not shown in FIG. 2) the $IC_{50}$ of tannic acid for PAI-1 (2.5 µM) was up to nearly 4-fold lower than the $IC_{50}$ of PAI-039 for PAI-1 (9.7 µM) (Gorlatova et al., J. Biol. Chem. 282: 9288-9296, 2007). This data demonstrates that tannic acid is an even more effective inactivator of PAI-1 than PAI-039 is in vitro.

Example 3

Figure 3:
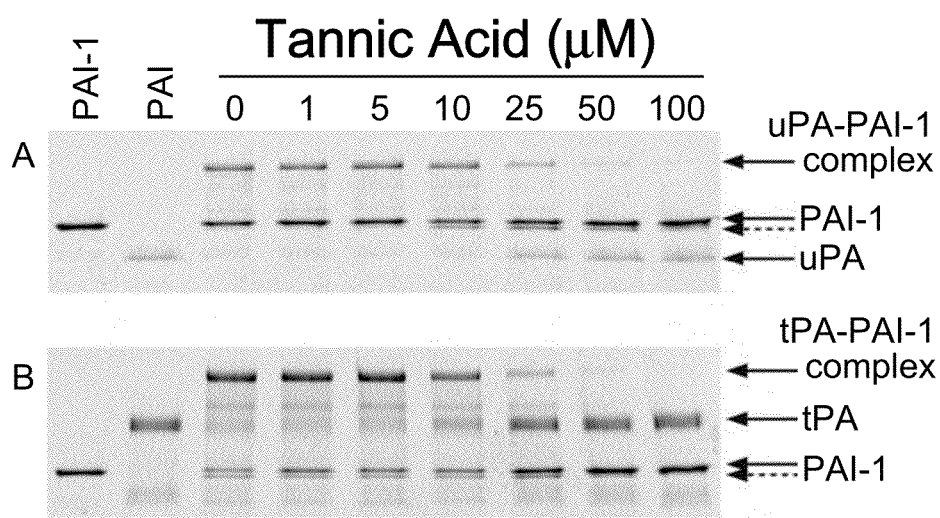
FIG. 3 shows that tannic acid inhibits PAI-1:plasminogen activator complex formation and stimulates PAI-1 cleavage.
Figure 5A:
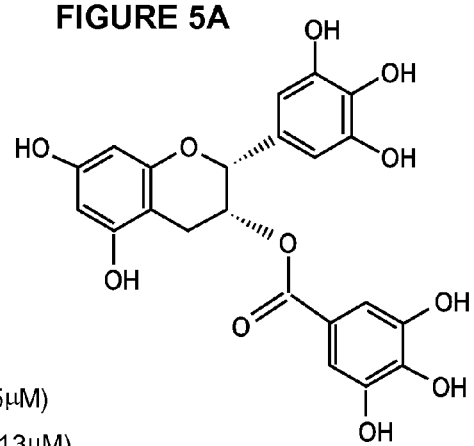
FIGS. 5A-5E show that the inhibition of PAI-1 by EGCG is pH sensitive.
Figure 5B:
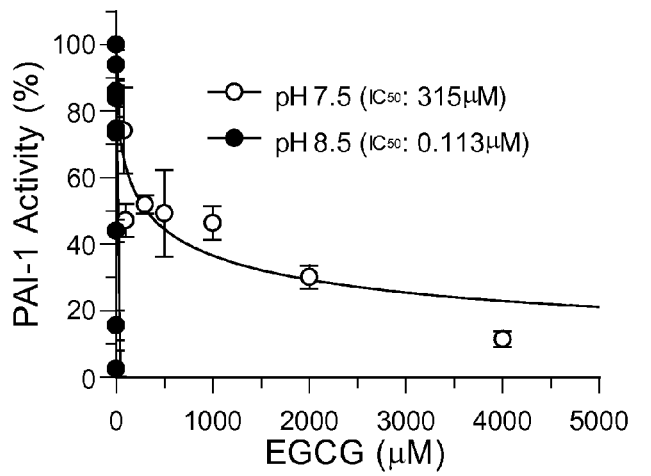
Figure 5C:
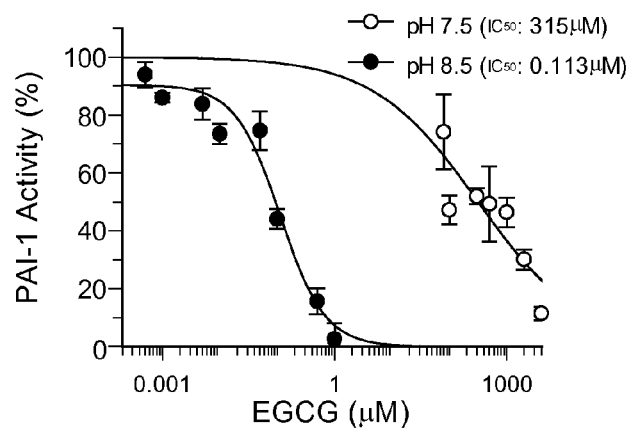
Figure 5D:
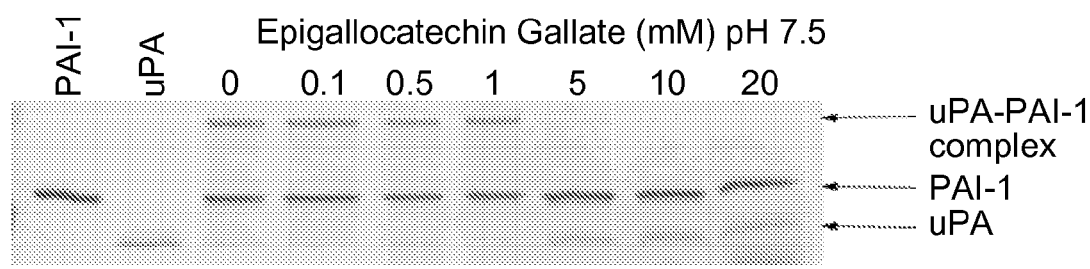
Figure 5E:
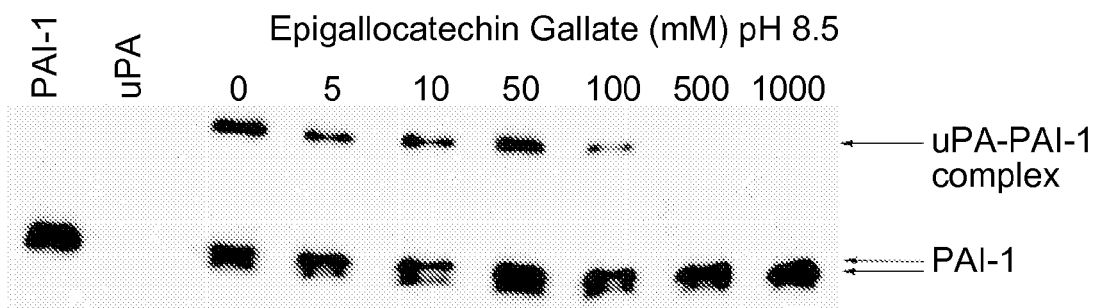

Tannic Acid Inhibits PAI-1:Plasminogen Activator Complex Formation and Stimulates PAI-1 Cleavage The mechanism of tannic acid inactivation of PAI-1 was investigated using SDS-PAGE analysis. PAI-1 (1 µg) was incubated with tannic acid at various concentrations from 0-100 µM (FIG. 3) for 15 min at 23° C. in assay buffer. Urokinase PA (FIG. 3A) or tPA (FIG. 3B) (1 µg) was added, and complexes were formed at 23° C. for 5 min. SDS buffer (reducing) was added to the samples, which were then boiled for 15 min and size-separated on 4-20% Tris-HCl gels by SDS-PAGE. Proteins were stained with Coomassie blue and scanned. In FIG. 3, the numbers above the lanes indicate the concentration of tannic acid, and the arrow with the dashed line indicates the position of cleaved PAI-1.

The data indicate that, like PAI-039, tannic acid also converts PAI-1 to a substrate for PAs (FIG. 3).

Example 4

Tannic Acid Inhibits Vitronectin-Bound PAI-1

In screening for PAI-1 inactivating compounds, tannic acid was identified as a PAI-1 antagonist. Tannic acid is unaffected by mutations in PAI-1 that reduce the efficacy of PAI-039 and, therefore, indicates that tannic acid binds PAI-1 at a site different from the putative PAI-039 binding site. To determine if tannic acid inhibits PAI-1, when bound to vitronectin, the following experiment was carried out.

Recombinant active human PAI-1 was assayed essentially as described in Example 2, with or without preincubation with a 5-fold molar excess of vitronectin. Essentially, recombinant active human PAI-1 (final 3.5 nM) was incubated for 15 min at 23° C. with increasing concentrations of tannic acid. Urokinase PA (final 6 nM) was added to each reaction well and incubated for an additional 5 min at 37° C. Urokinase PA activity was determined with pGlu-Gly-Arg pNA chromogenic substrate (final 0.25 mM). The rate of pNA release by uPA was measured at 405 nm for 15 min. Data were expressed as residual PAI-1 activity as a percent of control PAI-1 (100%).

Tannic acid inhibited PAI-1 activity even when bound to vitronectin, unlike PAI-039. Results suggest that tannic acid is inhibiting PAI-1 via a mechanism that is different from PAI-039. Taken together, with tannic acid's lower $IC_{50}$ for PAI-1 than PAI-039, the results indicate that tannic acid or a derivative of tannic acid is a more effective inhibitor of PAI-1 than is PAI-039.

Example 5

The Identification of Additional PAI-1 Inactivating Compounds

Additional PAI-1 compounds have been identified from the compound library by the screening methods of the invention described herein above. These compounds include, but are not limited to, hexachlorophene, quinalizarin, 5-nitrosalicylic acid, chlorogenic acid, caffeic acid, 3-nitro-L-tyrosine, 3-chloro-L-tyrosine, 5-chlorosalicylic acid, and polyphenon-60. The chemical formula, $IC_{50}$s at pH 7.5 and 8.5, and structure of each of these compounds (in addition to the four previously identified compounds, tannic acid, epigallocatechin 3,5-digallate, (−)-epigallocatechin gallate (EGCG), and gallic acid) are provided in FIG. 1.

Example 6

Inhibition of PAI-1 by Tannic Acid, EGCG, Gallic Acid, and Polyphenon-60 is pH Sensitive The known PAI-039 inhibitor tiplaxtinin (PAI-039) is not pH sensitive. However, preliminary data suggested that at least some of the PAI-1 inhibitors of the invention are pH sensitive and, thus, be acting via a novel mechanism. Therefore, to determine if pH had an effect on PAI-1 activity inhibition, the following experiments were carried out.

First, experiments were undertaken to determine if inhibition of PAI-1 by tannic acid is pH sensitive. Recombinant active human PAI-1 (final 3.2 nM) was incubated for 15 min at 23° C. with increasing concentrations of tannic acid. Next uPA (final 4 nM) was added to each reaction well and incubated for an additional 5 min at 37° C. UPA activity in each reaction mixture was determined with Z-Gly-Gly-Arg-AMC (Bachem) fluorogenic substrate (final 50 μM). The rate of AMC release by uPA was measured at an excitation wavelength of 370 nm and an emission of 440 nm for 15 min. Data were expressed as residual PAI-1 activity as a percent of control PAI-1 activity (see FIGS. 4-7). The data demonstrate that tannic acid at pH 8.5 had an $IC_{50}$ of 0.0091 μM (FIG. 4). The $IC_{50}$s at pH 6.5 and 7.5 were similar, at 7.36 μM and 7.15 μM, respectively (FIG. 4). Thus, tannic acid's effectiveness in inhibiting PAI-1 activity was improved by increasing pH.

Figure 6A:
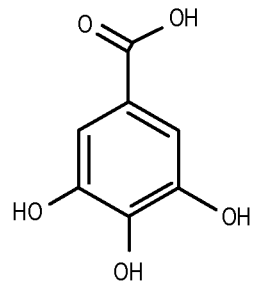
FIGS. 6A-6C show that the inhibition of PAI-1 by gallic acid is pH sensitive.
Figure 6B:
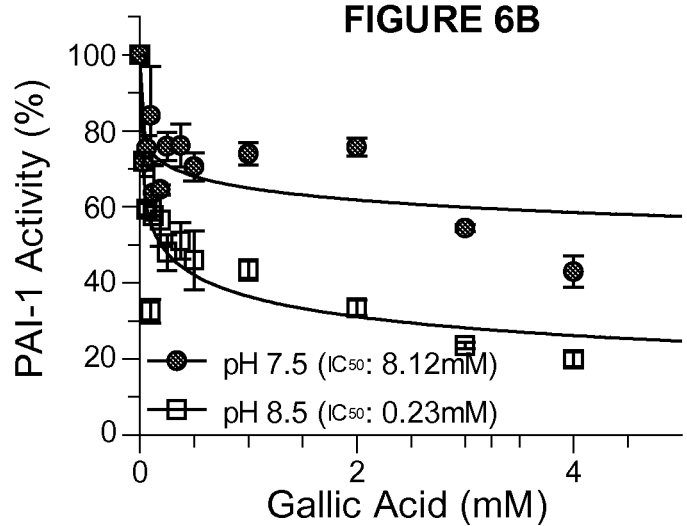
Figure 6C:
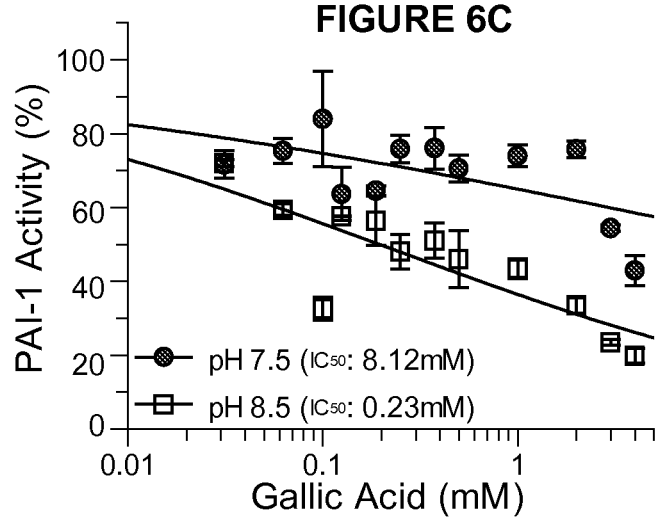
Figure 7A:
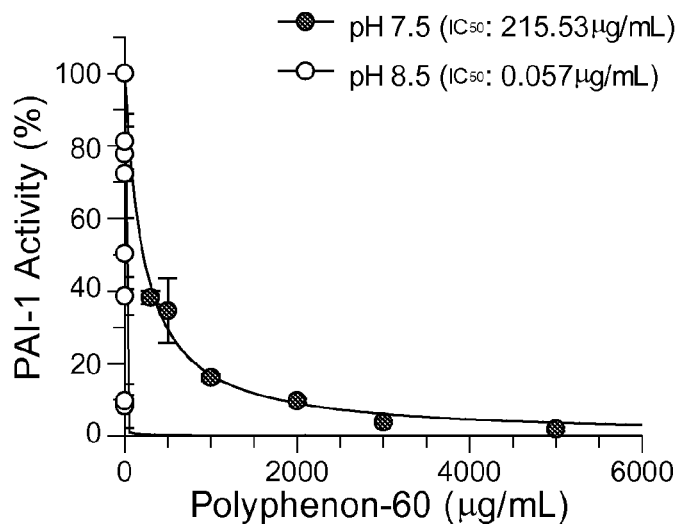
FIGS. 7A-7C show that the inhibition of PAI-1 by polyphenon-60, an extract from green tea, is pH sensitive.
Figure 7B:
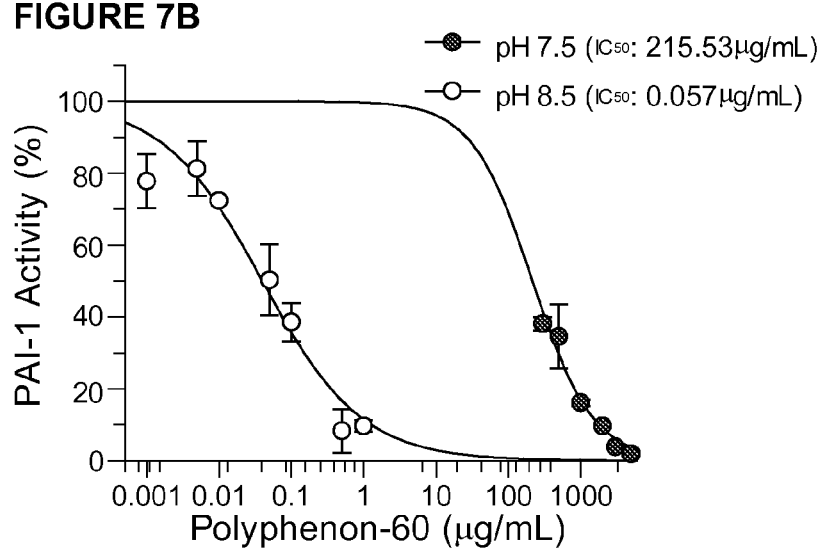
Figure 7C:
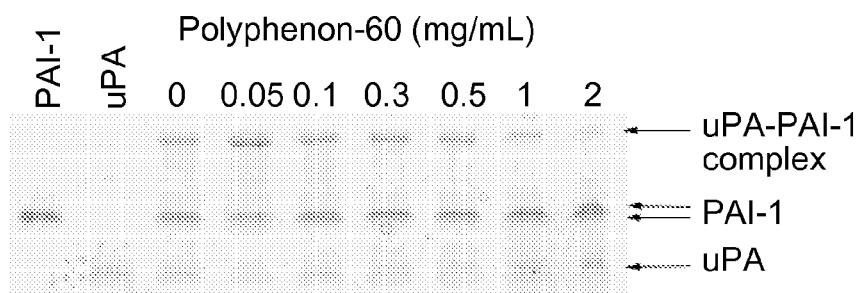
Figure 8F:
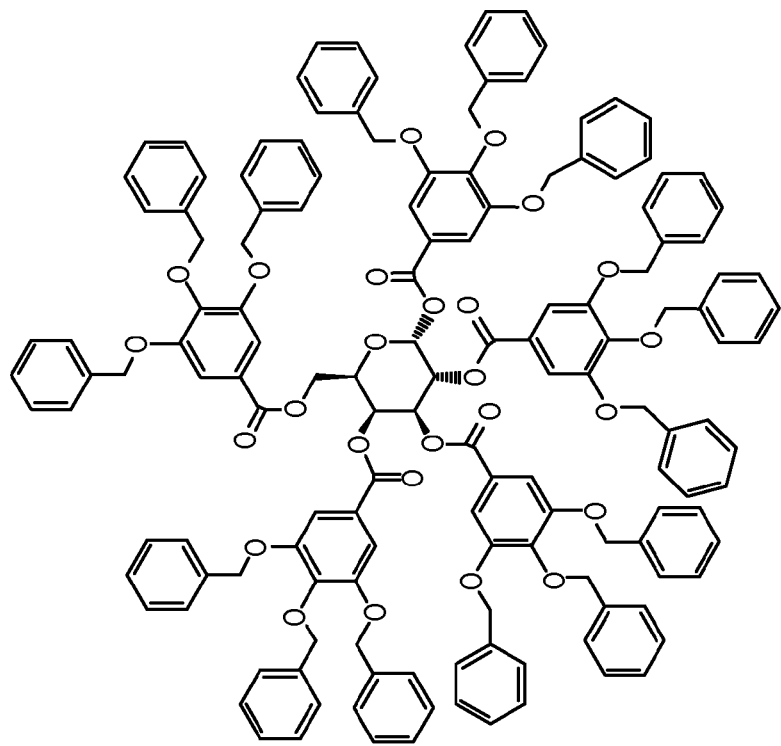
Figure 8E:
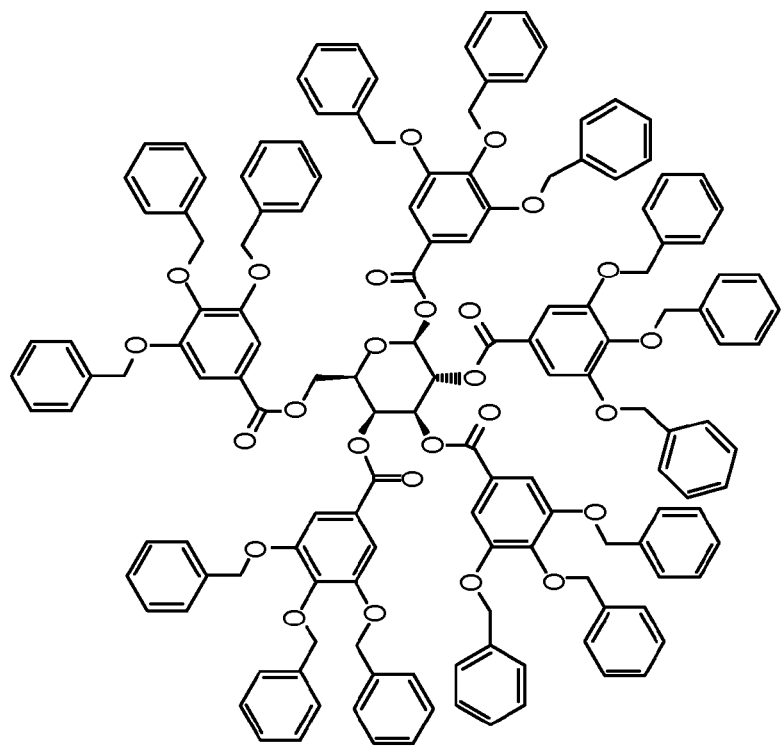
Figure 8G:
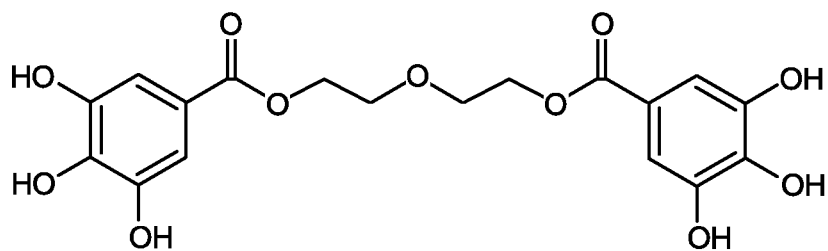
Figure 8H:
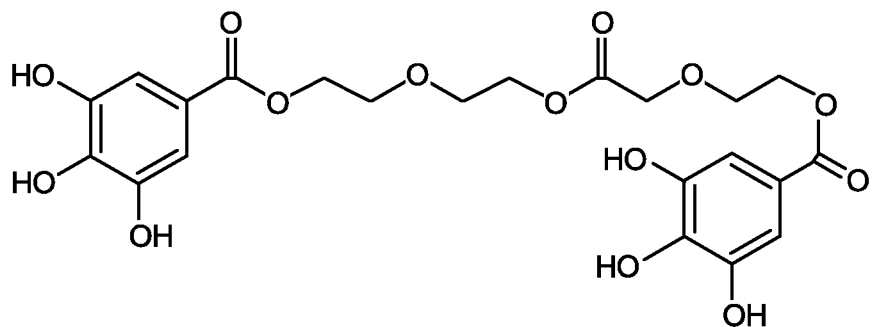
Figure 8I:
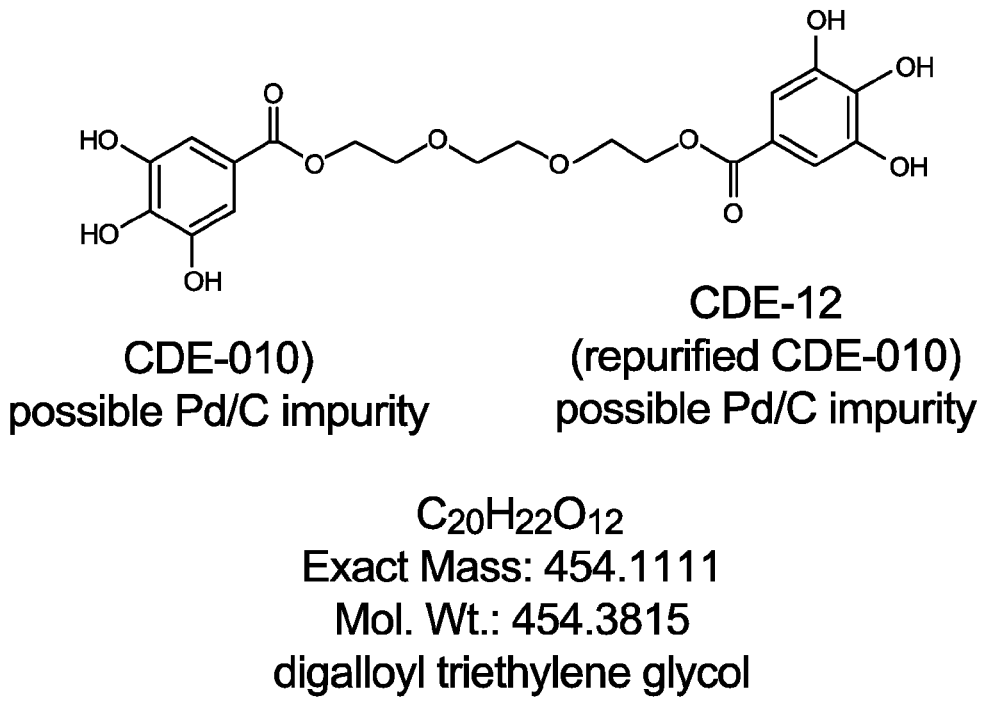
Figure 8J:
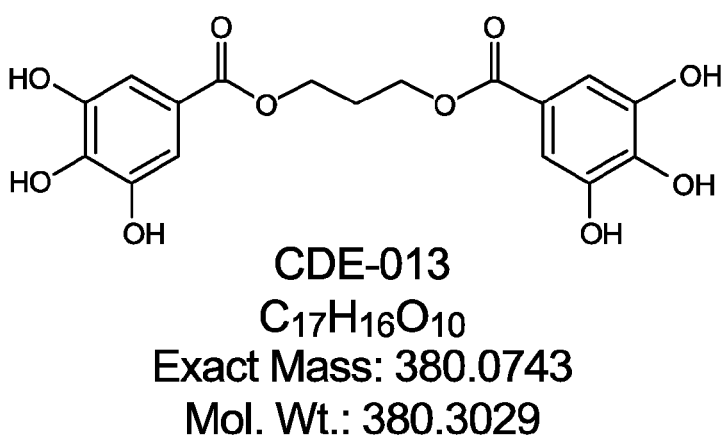
Figure 8K:
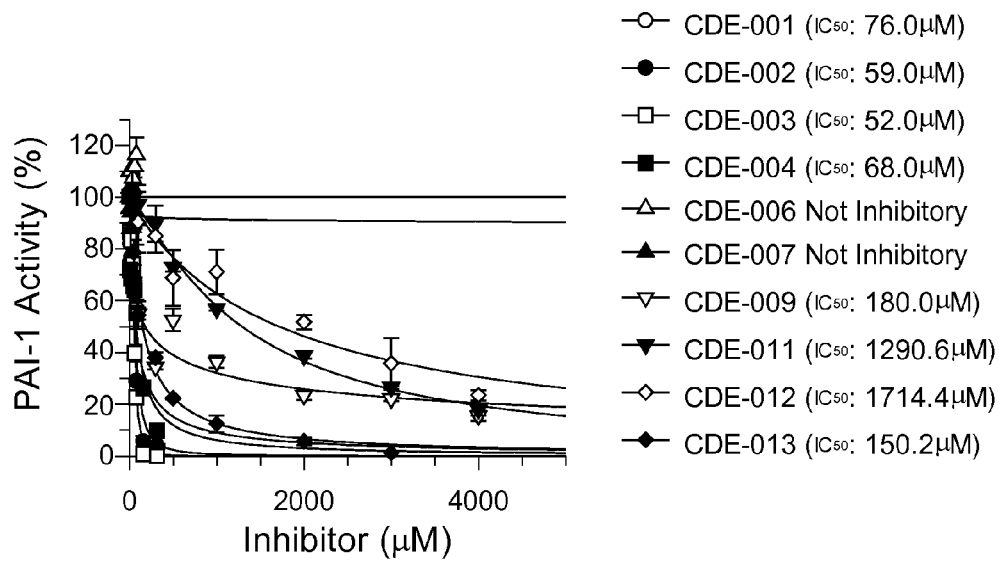
Figure 8L:
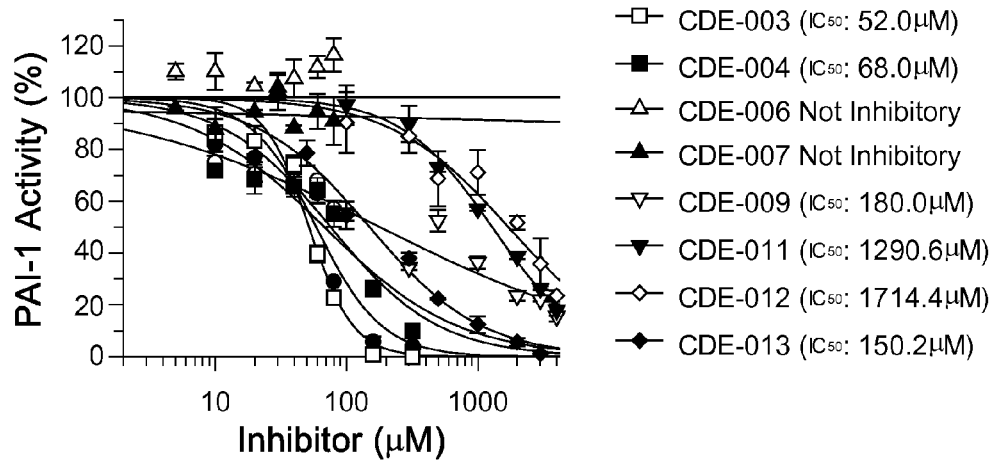

Next, experiments were carried out to determine if PAI-1 inhibition by other PAI-1 inhibitors was also pH sensitive. Thus, similar experiments were carried out to examine the effect of pH on inhibition with EGCG, gallic acid, and polyphenon-60 (green tea extract). Like with tannic acid, the PAI-1 inhibitory efficacy of each compound increased with increasing pH to 8.5 (FIGS. 5-7). In contrast, hexachlorophene efficacy did not improve at pH 8.5 compared to pH 7.5.

Example 7

Synthesis of Polyphenolic Compounds as Inhibitors of PAI-1

As discussed herein above, elevated levels of PAI-1 have been implicated in a variety of disease conditions. The development of therapeutic agents that act as selective inhibitors of PAI-1 may provide an approach to treat these conditions. The design and synthesis of a variety of polyphenolic compounds and their structure:activity relationship with PAI-1 is described.

Tannic acid is a naturally-occurring polyphenol, commonly found in black tea and the barks of various trees, and consists of multiple gallate esters arranged around a central glucose ring. Because tannic acid was shown to be an effective PAI-1 inhibitor as set out herein above, polyphenolic compounds were synthesized and tested for their ability to inhibit PAI-1 activity.

Based on the structure of identified PAI-1 inhibitors, compounds were synthesized and tested for their ability to inactivate PAI-1. In examining their structures and the effect that pH had on their respective potencies, a phenoxide anion was identified as an important moiety for binding to PAI-1. Further, in examining their structures, it was contemplated that the rest of the gallate is present, not primarily to engage in binding to the protein target, but instead to promote ionization of the phenol at physiological pH.

PAI-1 inhibitors that have more acidic phenols, and pKa values of less than or equal to 7, display potent inhibition of PAI-1. Strong evidence for this can be seen in the hexachlorophene and sulfonamide-based inhibitors, which contain a particularly acidic phenolic hydrogen due to the strategic placement of a strong electron withdrawing group. These compounds do not contain gallate groups, yet still display potent inhibition of PAI-1.

These PAI-1 inhibitors contain at least one phenolic hydroxyl group with proximal or conjugated electron withdrawing groups. Electron withdrawing groups include, but are not limiting to, halogens (—F, —Cl, —Br), nitro (—NO2), nitroso (—NO), ammonium (—NR3+), carbonyl (ketone, ester, aldehyde, imide, amide, thioester, etc.), nitrile (—CN), sulfonyl (—SO2R), sulfonate ester (—SO3R), sulfonate acid (—SO3H), sulfonamide (—SO2NR2), sulfoxy (—S=O), conjugated aromatics and heteroaromatics (—Ar).

Thus, using knowledge of PAI-1 inhibitors in the prior art and results obtained from the experiments described herein, novel PAI-1 inhibiting compounds were synthesized using a methodology as set out below.

Reaction Sequence A:

Typical procedure for the formation of pentagalloyl carbohydrates.

Step 1:

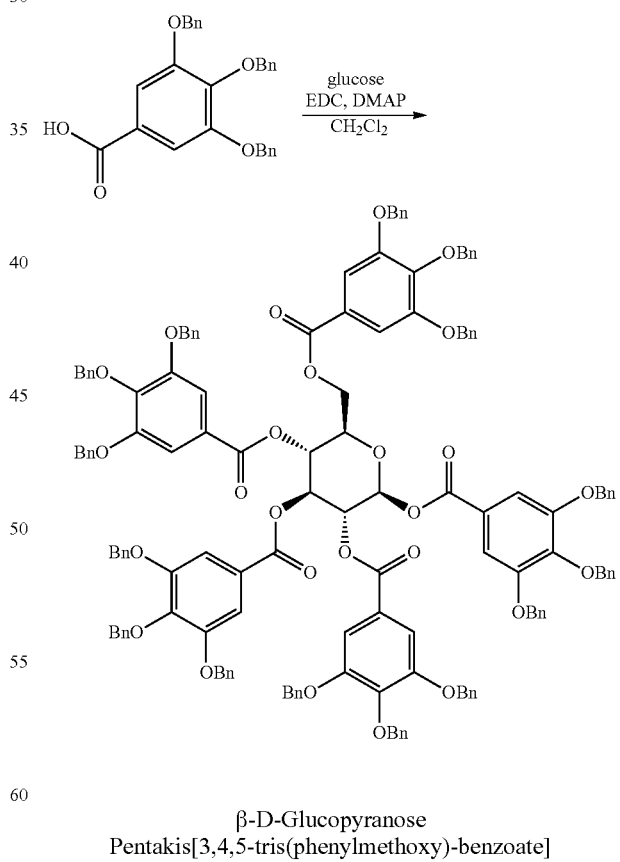

β-D-Glucopyranose
Pentakis[3,4,5-tris(phenylmethoxy)-benzoate]

A mixture of 1.17 mmol of D-glucose, 8.57 mmol of 3,4,5-tribenzyloxybenzoic acid, 10.68 mmol of EDC.HCl and 9.84 mmol of DMAP was suspended in 130 mL of $CH_2Cl_2$ and was heated at reflux overnight. The cooled reaction mixture was then extracted with 1N HCl (3×), saturated NaHCO$_3$ (2×), and brine (2×), the organic layer was dried over MgSO$_4$, filtered, and concentrated. The resulting residue was purified by column chromatography over silica gel (75:24:1 CH$_2$Cl$_2$: toluene:ethyl acetate) to provide 0.253 g (9%) of product. $^1$H NMR (CDCl$_3$, 400 MHz) δ 7.45–7.15 (m, 85H), 6.21 (d, J=8.0 Hz, 1H), 6.05 (t, J=10.0 Hz, 1H), 5.84 (dd, J=10.0, 8.0 Hz, 1H), 5.73 (t, J=10.0 Hz, 1H), 5.14–4.92 (m, 30H), 4.76 (m, 1H), 4.44 (m, 1H), 4.35 (m, 1H).

Step 2:

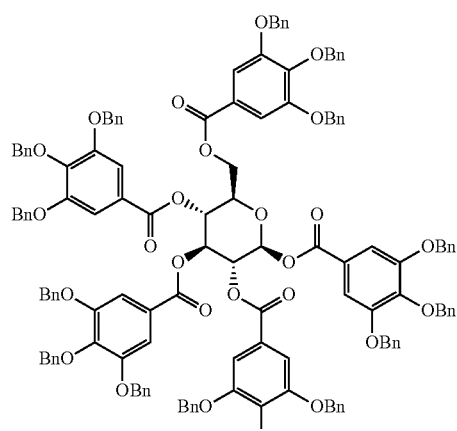

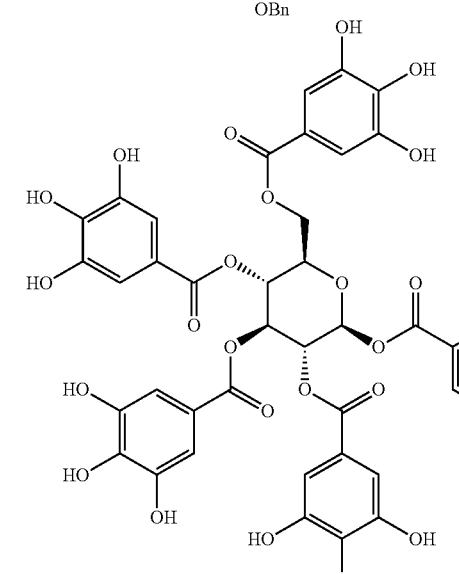

β-D-Glucopyranose
Pentakis[3,4,5-trihydroxybenzoate]

The product from step #1 above was dissolved in 30 mL THF. A catalytic amount of 10 wt % palladium on carbon was suspended in the mixture and a balloon containing H$_2$ was affixed to the stirring reaction flask. After 60 h at room temperature, the reaction mixture was filtered through Celite and the filtrate was evaporated to provide the title compound in 87% yield. $^1$H NMR (Acetone-d6, 400 MHz) δ 8.34–7.97 (m, 15H), 7.15 (s, 2H), 7.09 (s, 2H), 7.03 (s, 2H), 6.98 (s, 2H), 6.95 (s, 2H), 6.30 (d, J=8.2 Hz, 1H), 5.99 (t J=9.6 Hz, 1H), 5.61 (m, 2H), 4.52 (m, 2H), 4.37 (dd, J=12.8, 4.6 Hz, 1H).

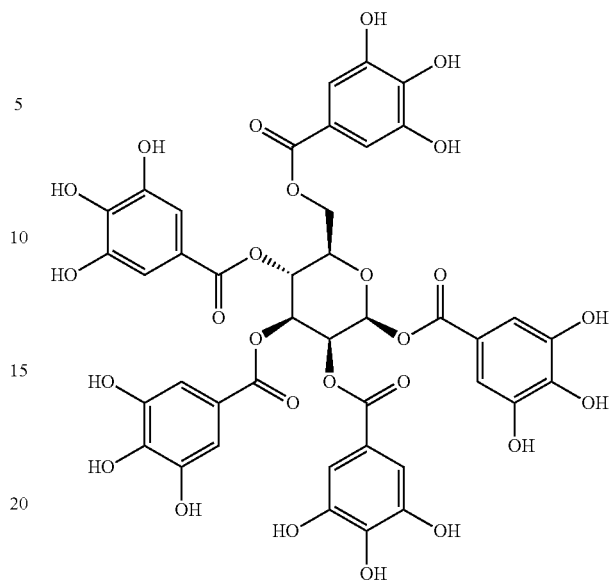

β-D-Mannopyranose
Pentakis[3,4,5-trihydroxybenzoate]

Obtained in 18% overall yield from mannose via reaction sequence A. $^1$H NMR (Acetone-d6, 400 MHz) δ 8.46–7.97 (m, 15H), 7.29 (s, 2H), 7.20 (s, 2H), 7.13 (s, 2H), 7.08 (s, 2H), 6.96 (s, 2H), 6.46 (d, J=1.4 Hz, 1H), 5.93 (t, J=10.1 Hz, 1H), 5.85 (dd, J=10.1, 3.2 Hz, 1H), 5.76 (m, 1H), 4.66 (m, 1H), 4.50 (dd, J=10.1, 2.3 Hz, 1H), 4.44 (dd, J=12.4, 5.5, 1H).

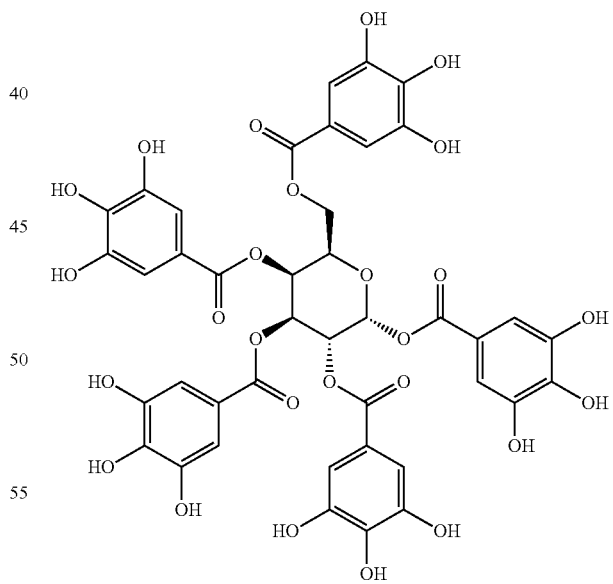

α-D-Galactopyranose
Pentakis[3,4,5-trihydroxybenzoate]

Obtained in 28% overall yield from galactose via reaction sequence A. $^1$H NMR (Acetone-d6, 400 MHz) δ 8.36–8.00 (m, 15H), 7.25 (s, 2H), 7.19 (s, 2H), 7.04 (s, 2H), 6.96 (m, 4H), 6.79 (d, J=3.7 Hz, 1H), 6.05-5.99 (m, 2H), 5.78 (dd, J=11.0, 3.7 Hz, 1H), 4.94 (m, 1H), 4.46 (dd, J=11.0, 6.9 Hz, 1H), 4.24 (m, 1H).

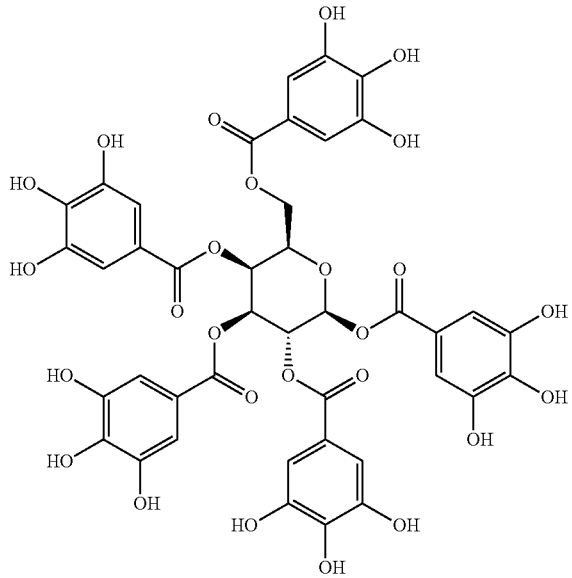 [SMILES: O=C(OC[C@H]1O[C@@H](OC(=O)c2cc(O)c(O)c(O)c2)[C@H](OC(=O)c2cc(O)c(O)c(O)c2)[C@@H](OC(=O)c2cc(O)c(O)c(O)c2)[C@H]1OC(=O)c1cc(O)c(O)c(O)c1)c1cc(O)c(O)c(O)c1]

β-D-Galactopyranose
Pentakis[3,4,5-trihydroxybenzoate]

Obtained in 12% overall yield from galactose via reaction sequence A. ¹H NMR (Acetone-d6, 400 MHz) δ 8.18 (bs, 15H), 7.19 (s, 2H), 7.13 (s, 2H), 7.08 (s, 2H), 6.99 (s, 2H), 6.94 (s, 2H), 6.32 (d, J=7.8 Hz, 1H), 5.92 (t J=4.0 Hz, 1H), 5.83 (m, 2H), 4.75 (t, J=8.0 Hz, 1H), 4.49 (m, 1H), 4.27 (m, 1H).

Reaction Sequence B:

Typical procedure for the formation of digalloyl compounds.

Step 1:

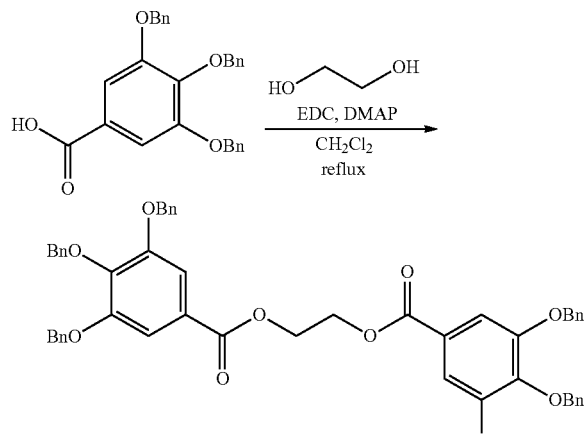

Di-O-(3,4,5-tribenzyloxybenzoyl)ethylene glycol

A suspension of 2 mmol of ethylene glycol, 6 mmol of 3,4,5-tribenzyloxybenzoic acid, 7.5 mmol of EDC.HCl, and 6.9 mmol DMAP in 120 mL of CH₂Cl₂ was heated at reflux overnight. The cooled reaction mixture was then extracted with 1N HCl (3×), saturated NaHCO₃ (2×), and brine (2×), the organic layer was dried over MgSO₄, filtered, and concentrated. The resulting residue was triturated with methanol to provide 0.258 g (23%) of product. ¹H NMR (CDCl₃, 400 MHz) δ 7.40-7.20 (m, 34H), 5.04 (m, 12H), 4.59 (s, 4H).

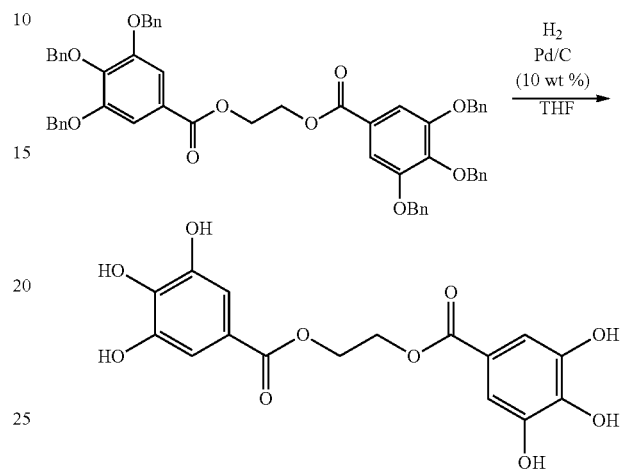

1,2-Bis-galloyloxyethane

The product from step #1 above was dissolved in 25 mL THF. A catalytic amount of 10 wt % palladium on carbon was suspended in the mixture and a balloon containing H₂ was affixed to the stirring reaction flask. After 18 h at room temperature, the reaction mixture was filtered through Celite and the filtrate was evaporated to provide the title compound in quantitative yield. ¹H NMR (Acetone-d6, 400 MHz) δ 8.19 (s, 4H), 8.03 (s, 2H), 7.12 (s, 4H), 4.52 (s, 4H).

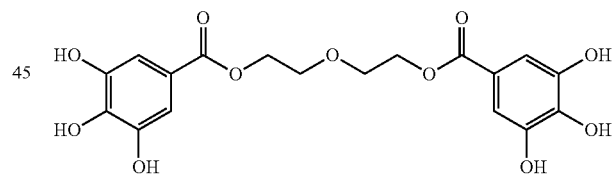

Diethylene glycol, digallate

Obtained in 13% overall yield from diethylene glycol via reaction sequence B.

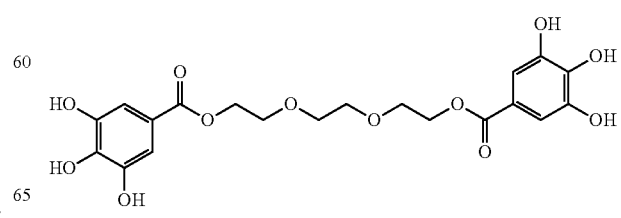

Triethylene glycol, digallate

Obtained in 11% overall yield from triethylene glycol via reaction sequence B. $^1$H NMR (Acetone-d6, 400 MHz) δ 8.13 (bs, 6H), 7.12 (s, 4H), 4.31 (m, 4H), 3.76 (m, 4H), 3.65 (s, 4H).

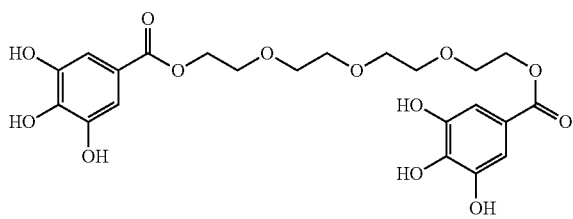 [SMILES: O=C(OCCOCCOCCOCCOC(=O)c1cc(O)c(O)c(O)c1)c1cc(O)c(O)c(O)c1]

Tetraethylene glycol, digallate

Obtained in 11% overall yield from tetraethylene glycol via reaction sequence B. $^1$H NMR (Acetone-d6, 400 MHz) δ 8.25 (s, 6H), 7.12 (s, 4H), 4.31 (m, 4H), 3.74 (m, 4H), 3.60 (m, 8H).

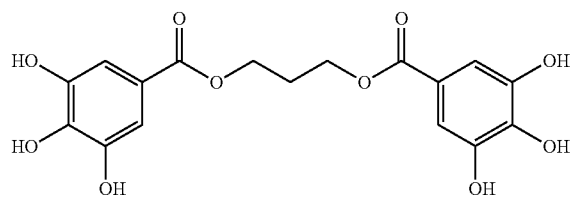 [SMILES: O=C(OCCCOC(=O)c1cc(O)c(O)c(O)c1)c1cc(O)c(O)c(O)c1]

Propane-1,3-diol, digallate

Obtained in 12% overall yield from propane-1,3-diol via reaction sequence B. $^1$H NMR (DMSO-d6, 400 MHz) δ 9.25 (s, 4H), 8.95 (s, 2H), 6.92 (t, J=6.4 Hz, 4H). 2.04 (quin, J=6.0 Hz, 2H).

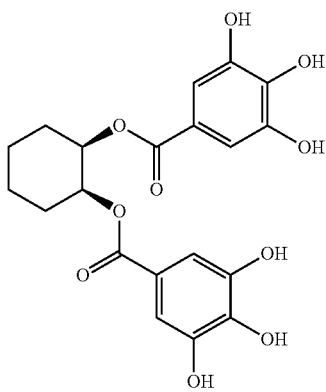 [SMILES: O=C(O[C@H]1CCCC[C@H]1OC(=O)c1cc(O)c(O)c(O)c1)c1cc(O)c(O)c(O)c1]

Cyclohexane-cis-1,2-diol digallate

Obtained in 10% overall yield from cyclohexane-cis-1,2-diol via reaction sequence B. $^1$H NMR (DMSO-d6, 400 MHz) δ 9.00 (bs, 6H), 6.88 (s, 4H), 5.11 (m, 2H), 1.87 (m, 2H), 1.75–1.64 (m, 4H), 1.47 (m, 2H).

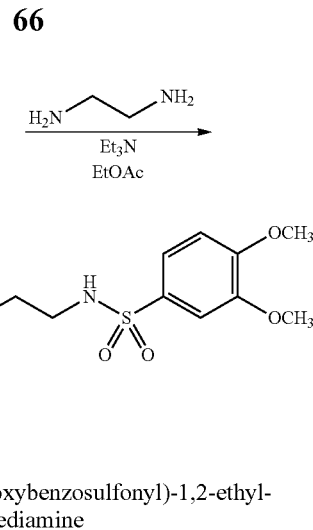

N,N'-Bis-(3,4-dimethoxybenzosulfonyl)-1,2-ethylenediamine

To a solution of 4.23 mmol of 3,4-dimethoxysulfonyl chloride in 75 mL ethyl acetate was slowly added 19.2 mmol of triethylamine. 1,2-Diaminoethane (1.92 mmol) was added dropwise and the reaction mixture was allowed to stir overnight. The solid white precipitate was filtered, washed with water, and dried under vacuum to provide 0.739 g (89%) of the title compound. $^1$H NMR (acetone-d6, 400 MHz) δ 7.35 (dd, J=8.7, 1.8 Hz, 2H), 7.29 (d, J=2.3 Hz, 2H), 7.06 (d, J=8.2 Hz, 2H), 3.88 (s, 6H), 3.84 (s, 6H), 2.93 (s, 4H).

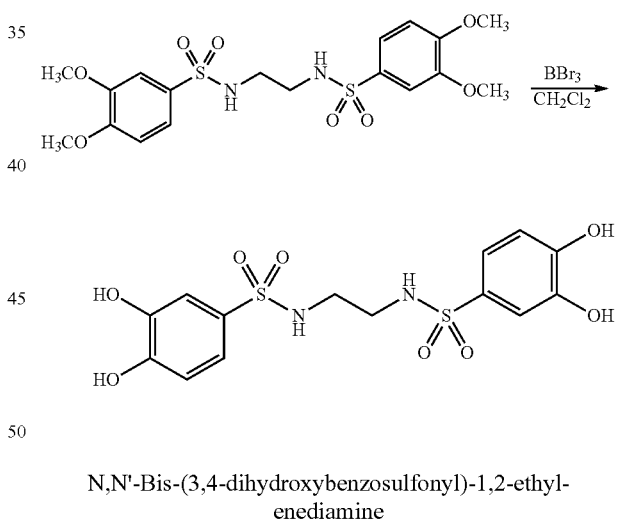

N,N'-Bis-(3,4-dihydroxybenzosulfonyl)-1,2-ethylenediamine

To a solution of 150 mg of N,N'-bis-(3,4-dimethoxybenzosulfonyl)-1,2-ethylenediamine in 3 mL of $CH_2Cl_2$ was added dropwise 3.47 mL of a 1 M solution of $BBr_3$ in $CH_2Cl_2$. The reaction was stirred overnight under an atmosphere of $N_2$. The reaction was then quenched by the careful addition of 1 mL of methanol. The solvent was removed by rotary evaporation to provide a brown oil, which was dissolved in ethyl acetate and washed twice with water. The remaining organic layer was dried ($Na_2SO_4$), filtered, and concentrated in vacuo to provide 107 mg (82%) of the title compound. $^1$H NMR (acetone-d6, 400 MHz) δ 7.26 (d, J=2.4 Hz, 2H), 7.18 (dd, J=8.7, 2.3 Hz, 2H), 6.93 (d, J=8.7 Hz, 2H), 2.93 (s, 4H).

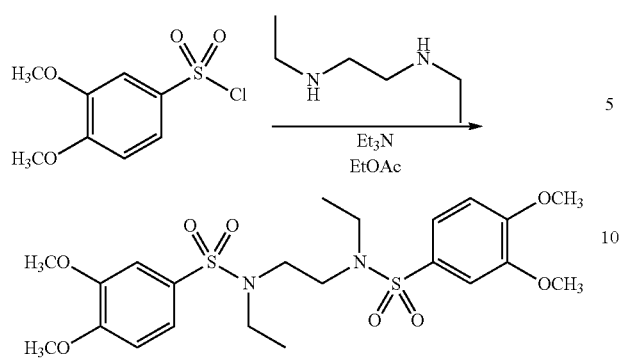

N,N'-Diethyl-N,N'-bis-(3,4-dimethoxybenzosulfonyl)-1,2-ethylenediamine

To a solution of 4.23 mmol of 3,4-dimethoxysulfonyl chloride in 75 mL ethyl acetate was slowly added 19.2 mmol of triethylamine. N—N'-Diethylethylenediamine (1.92 mmol) was added dropwise and the reaction mixture was allowed to stir overnight. The solid white precipitate was filtered off and discarded. The filtrate was washed with 1N HCl (2×) and brine (2×), dried over MgSO$_4$, filtered and concentrated by rotary evaporation to provide 0.998 g (quantitative yield) of the title compound. $^1$H NMR (DMSO-d6, 400 MHz) δ 7.41 (dd, J=8.7, 1.9 Hz, 2H), 7.28 (d, J=2.3 Hz, 2H), 6.95 (d, J=8.7 Hz, 2H), 3.95 (s, 6H), 3.94 (s, 6H), 3.28 (s, 4H), 3.21 (q, J=7.3 Hz, 4H), 1.16 (t, J=6.9 Hz, 6H).

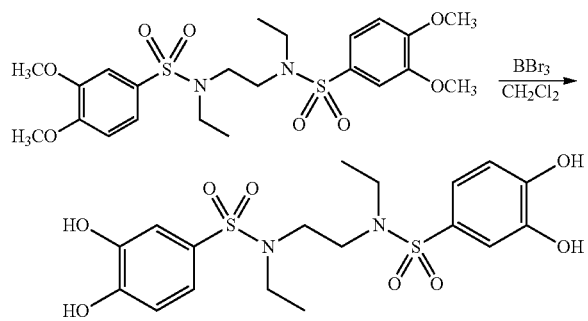

N,N'-Diethyl-N,N'-bis-(3,4-dihydroxybenzosulfonyl)-1,2-ethylenediamine

To a solution of 300 mg of N,N'-diethyl-N,N'-bis-(3,4-dimethoxybenzosulfonyl)-1,2-ethylenediamine in 3 mL of CH$_2$Cl$_2$ was added dropwise 6.15 mL of a 1 M solution of BBr$_3$ in CH$_2$Cl$_2$. The reaction was stirred overnight under an atmosphere of N$_2$. The reaction was then quenched by the careful addition of 1 mL of methanol. The solvent was removed by rotary evaporation to provide a brown oil, which was dissolved in ethyl acetate and washed twice with water. The remaining organic layer was dried (Na$_2$SO$_4$), filtered, and concentrated in vacuo to provide the title compound. $^1$H NMR (DMSO-d6, 400 MHz) δ 9.93 (bs, 2H), 9.66 (bs, 2H), 7.08 (d, J=2.3 Hz, 2H), 7.03 (dd, J=8.2, 2.3 Hz, 2H), 6.84 (d, J=8.2 Hz, 2H), 3.05 (m, 8H), 0.99 (t, J=7.4 Hz, 6H).

tert-Butyloxycarbonyl-3-nitro-L-tyrosine

To a solution of 6 mmol of 3-nitrotyrosine in 30 mL of NaOH and 8 mL of tert-butanol was added 8 mmol of di-tert-butyldicarbonate. The reaction was allowed to stir overnight. The tert-butanol was removed via rotary evaporation, 25 mL of ethyl acetate was added. The mixture was cooled to 0° C. and 1 N KHSO$_4$ was added slowly with stirring until the pH of the solution was ~2-3. The aqueous phase was separated and extracted with ethyl acetate (2×). The organic layers were combined, washed with brine, dried over Na$_2$SO$_4$, filtered and concentrated in vacuo to provide 1.27 g (65%) of the title compound. $^1$H NMR (DMSO-d6, 400 MHz) δ 10.76 (bs, 1H), 7.73 (d, J=2.3 Hz, 1H), 7.40 (dd, J=8.7, 2.3 Hz, 1H), 7.13 (d, J=8.2 Hz, 1H), 7.01 (d, J=8.7 Hz, 1H), 4.02 (m, 1H), 2.96 (dd, J=13.8, 4.1 Hz, 1H), 2.73 (dd, J=13.5, 10.5 Hz, 1H), 1.26 (s, 9H).

Using the methodology as described above, PAI-1 inhibitors were synthesized. These compounds include, but are not limited to, CDE-001, CDE-002, CDE-003, CDE-004, CDE-006, CDE-007, CDE-008, CDE-009, CDE-010, CDE-011, CDE-012, CDE-013, CDE-021, CDE-028, CDE-029, CDE-030, CDE-031, and CDE-032. The structure of each of these compounds is set out in Table 1.

Example 8

Inhibition of PAI-1 by CDE-Compounds is pH Sensitive

To determine if pH had an effect on PAI-1 inhibition in the synthesized PAI-1 inhibitors, experiments were carried out to determine if inhibition of PAI-1 by various CDE-compounds is also pH sensitive.

Recombinant active human PAI-1 (final 3.2 nM) was incubated for 15 min at 23° C. with increasing concentrations of inhibitor. Next uPA (final 4 nM) was added to each reaction well and incubated for an additional 5 min at 37° C. UPA activity in each reaction mixture was determined with Z-Gly-Gly-Arg-AMC (Bachem) fluorgenic substrate (final 50 μM). The rate of AMC release by uPA was measured at an excitation wavelength of 370 nm and an emission of 440 nm for 15 min. Data (FIG. 8) were expressed as residual PAI-1 activity as a percent of control PAI-1 activity. Note that in this experiment CDE-006 and CDE-007 were not inhibitory. The data demonstrate the PAI-1 inhibitory efficacy at pH 7.5 of CDE-001, CDE-002, CDE-003, CDE-004, CDE-009, and CDE- 011, CDE-012, and CDE-013 and show that these compounds are effective PAI-1 inhibitors. In addition, PAI-1 inhibition increased with increasing pH to 8.5 (data not shown).

Additional experiments with CDE-021, CDE-028, CDE-029, CDE-030, CDE-030, CDE-031, and CDE-032 also have shown that they are effective inhibitors of PAI-1 and, likewise, their inhibition efficacy increased with increasing pH, for example, from pH 6.5 to pH 7.5 to pH 8.5. In one experiment, CDE-008 demonstrated an $IC_{50}$ of 325 µM at pH 6.5, an $IC_{50}$ of 0.288 µM at pH 7.5, and an $IC_{50}$ of 0.064 µM at pH 8.5.

Example 9

PAI-1 Inactivation Results in Increased HDL and Decreased VLDL

To determine if the differences in lipid profiles between the PAI-1 null mice and the wild-type mice (shown in Example 1) were due to specific interactions between PAI-1 and lipid metabolic pathways, the pharmacological inactivation of PAI-1 by a PAI-inhibitor, PAI-039, was carried out. The theory is that PAI-039 treatment affect normal cholesterol metabolism and alters lipid profiles.

Previous studies by others have demonstrated that the PAI-1 inhibitor, PAI-039 (tiplaxtinin), has efficacy against PAI-1 in vivo, accelerating fibrinolysis following vascular injury to levels similar to those observed in PAI-1 null mice (Smith et al., Blood 107: 132-134, 2006; Weisberg et al., Arterioscler. Thromb. Vasc. Biol. 25: 365-371, 2005; Elokdah et al., J. Med. Chem. 47: 3491-3494, 2004; Hennan et al., J. Pharmacol. Exp. Ther. 314: 710-716, 2005). PAI-039 has also been shown in vivo to protect mice from nutritionally-induced obesity (Crandall et al., Arterioscler. Thromb. Vasc. Biol. 26: 2209-2215, 2006).

PAI-039 was administered orally to two different strains of mice, C57BL/6J and 129. Age- and sex-matched groups were fed standard mouse chow (#5001, Harlan Teklad, Indianapolis, Ind.) with or without PAI-039 (5 mg PAI-039/gram of chow). All diets were formulated by the manufacturer and the concentration of drug in the diet was validated by mass spectrometry at Wyeth Research. Mice were fed for two weeks after which citrated plasma was prepared from each group and lipid profiles were determined by enzyme assays and HPLC analysis.

As expected, plasma PAI-1 activity was decreased in mice receiving PAI-039 with plasma levels of active PAI-1 in the C57BL/6J mice being reduced from 0.47±0.13 mg/mL in control mice to 0.37±0.08 ng/mL in PAI-039-treated mice. In both strains of mice examined, treatment with PAI-039 significantly altered the lipid profile compared to their matched control mice that did not receive PAI-039.

In both strains, HDL cholesterol increased significantly in PAI-039-treated mice (11% increase in C57BL/6J and 45% increase in 129) and VLDL decreased significantly in PAI-039-treated mice (49% in C57BL/6J and 35% in 129). Other changes in lipids were also noted in each strain that received PAI-039 treatment; however, these changes were not statistically significant. For example, total cholesterol increased in both PAI-039-treated strains, but the difference was not significant in the C57BL/6J mice.

Thus, the increased HDL cholesterol and decreased VLDL cholesterol in PAI-039-treated mice indicate that inhibiting PAI-1 activity can alter normal cholesterol metabolism. Moreover, these changes were similar, though not identical, to those seen in Example 1. Specifically, HDL cholesterol increased in both PAI-1 null mice and in PAI-039-treated mice (HDL was approximately 30% higher in PAI-1 null mice compared to wild-type mice and approximately 28% higher in PAI-039-treated mice (average increase for C57BL/6J and 129 mice).

These results suggest that reducing PAI-1 levels, either genetically or pharmacologically, can significantly raise HDL levels. In contrast, VLDL did not show any differences between PAI-1 null mice and wild-type mice, whereas in the PAI-039-treated mice, both C57BL/6J and 129 strains showed a significant decrease in VLDL levels (42% average decrease) compared to controls.

Example 10

PAI-1 Inactivation does not Alter Lipid Metabolism in PAI-1 Null Mice

The observation that PAI-039 affects both HDL and VLDL in a similar manner in both strains of mice in Example 9 suggests that PAI-039's effects may be specific for a pathway common to HDL and VLDL; however, it does not prove that the effects are mediated through an interaction of PAI-039 with PAI-1. To determine whether the oral administration of PAI-039 in PAI-1 null mice also raises HDL and lowers VLDL, the experiments set forth in Example 9 were repeated using PAI-1 null mice in place of the wild-type mice. Animals were treated for two weeks as set out in Example 9, and lipid analysis was carried out.

PAI-039 had no significant effect on metabolism in PAI-1 null mice, indicating that the effects of PAI-039 on plasma lipid profiles require the presence of PAI-1, and strongly implies that PAI-1 interacts directly with lipoprotein metabolic pathways.

These results are notably important because they suggest that the changes seen in cholesterol metabolism in mice with a genetic deficiency in PAI-1 could result from secondary effects associated with developmental changes in mice with complete PAI-1 deficiency, and might not be due to the loss of a direct interaction between PAI-1 and some factor(s) associated with cholesterol metabolism. However, the requirement of PAI-1 for PAI-039 treatment to induce acute changes in lipid profiles demonstrates that PAI-039 cannot be acting directly on cholesterol metabolic pathways. Instead, the simplest explanation is that PAI-1 itself interacts directly with one or more of these pathways and that the removal of PAI-1, either genetically or pharmacologically, alters the steady-state balance of cholesterol metabolism.

Example 11

PAI-1 Blocks Binding of VLDL to VLDL-R

Because PAI-039 specifically lowered VLDL levels in two strains of mice treated with PAI-039 (see Example 9), a study was set out to determine how PAI-1 affects VLDL. Experiments were carried out to detect if PAI-1 enhances or inhibits VLDL binding to the VLDL receptor (VLDL-R), and determine if altering this interaction by treatment with PAI-039 could influence VLDL levels in vivo.

First, to measure the direct binding of purified VLDL to the VLDL-R in the presence of PAI-1, the following experiment was carried out. The purified ectodomain of VLDL-R was bound to microtiter plates and blocked with bovine serum albumin (BSA). Increasing concentrations of VLDL (Intracel, Frederick, Md.) labeled with the fluorescent lipophilic probe, DiI, (DiI-VLDL) were then allowed to bind. The binding of DiI-VLDL was measured in a fluorescent plate reader, and was shown to be specific and saturable. Specificity was demonstrated by the lack of binding of the VLDL to BSA coated plates, and by the inhibition of VLDL binding by the receptor-associated protein (RAP), which is a receptor antagonist and a general antagonist of members of the LDL-R family (Marienfeld et al., Hepatol. 37:1097-1104, 2003).

Similar results were also obtained when the assay was carried out with unlabeled VLDL using an ELISA format, where VLDL binding was detected with a monoclonal antibody to apolipoprotein E (ApoE) (3H11, Ottawa Heart Institute Research Corp., Ottawa, Calif.). Using this assay, the ability of PAI-1 to promote or inhibit the binding of VLDL to the VLDL-R was then examined in a competitive binding assay, where a constant amount of Dil-VLDL was added together with increasing amounts of wild-type PAI-1. The PAI-1 used in the experiments was either in the active conformation, the latent conformation, or in a complex with uPA.

Assay results showed that PAI-1 did not enhance the binding of VLDL to VLDL-R, but rather that PAI-1 competes with VLDL for receptor binding and can completely inhibit VLDL binding to VLDL-R. There was no significant difference in VLDL binding to the three different forms of PAI-1 tested ($IC_{50}$ of 69±5.5 nM for the PAI-1:uPA complex; $IC_{50}$ of 80±8.7 nM for active PAI-1; and $IC_{50}$ of 84±8.3 nM for latent PAI-1). The data suggest that either PAI-1 is inhibiting VLDL binding through an alternate interaction rather than through PAI-1 binding to VLDL-R, or that binding of PAI-1 to VLDL-R is different that its binding to other LRL-R family members, such as lipoprotein receptor-related protein (LRP) and GP330/Megalin, which can only bind PAI-1 with high affinity when it is in a complex with a protease (Stefansson et al., J. Biol. Chem., 271:8215-8220, 1996; Stefansson et al., J. Biol. Chem. 273:6358-6366, 1998; Stefansson et al., J. Biol. Chem. 279:29981-29987, 2004).

Taken together, the data indicate that PAI-1 must be inhibiting VLDL binding to VLDL-R through some mechanism other than by simply binding to the receptor and blocking its association with VLDL, because all three conformations of PAI-1 showed similar capacity to inhibit ($IC_{50}$ values) VLDL binding to VLDL-R, even though all three conformations of PAI-1 have very different affinities for the VLDL-R with only the PAI-1:uPA complex binding to VLDL-R with high affinity. For example, latent PAI-1 has an estimated kDa for binding to VLDL-R that is nearly 10-fold higher than that of the PAI-1:uPA complex, and yet the $IC_{50}$s for the inhibition of VLDL binding in the experiment were nearly identical. Similarly, the active form of PAI-1 is equally efficient at inhibiting the binding of VLDL to VLDL-R, even though its binding to VLDL-R is even lower than that of latent PAI-1.

Instead, these results suggest that PAI-1 is blocking the binding of VLDL to VLDL-R by an alternative mechanism, possibly through the association of PAI-1 with the VLDL particle.

Example 12

PAI-1 Interacts Directly with the VLDL Particle

To determine if PAI-1 is blocking the binding of VLDL to the VLDL-R by the association of PAI-1 with the VLDL particle, the following experiment was performed. The competitive binding assay using active PAI-1 and the PAI-1:uPA complex, as described in Example 11 was repeated. However, in this experiment the PAI-1 or PAI-1:uPA complex was either (i) preincubated with VLDL-R for one hour to permit binding, after which the unbound PAI-1 was washed away immediately prior to the addition or the VLDL, or (ii) added together with VLDL to VLDL-R coated plates without any preincubation. After one hour, the unbound VLDL was washed away and the bound VLDL was detected with an anti-ApoE antibody.

PAI-1 competed with VLDL for binding to VLDL-R only when preincubated with the VLDL. This is understandable with active PAI-1, because PAI-1 binds weakly to VLDL-R and would be expected to be washed away prior to the addition of the VLDL. However, in the case of the PAI-1:uPA complex, the binding affinity is high and at the highest doses of PAI-1:uPA complex added, the receptor binding was not saturated. Thus, if the PAI-1:uPA complex is inhibiting VLDL binding by blocking a site on the VLDL-R, the inhibition of VLDL binding, even in the washed wells, was expected. However, no inhibition was observed.

This lack of inhibition of VLDL binding to VLDL-R strongly suggests that at least the PAI-1:uPA complex is interacting with some ligand on the VLDL particle and that this interaction interferes with VLDL binding to VLDL-R.

Example 13

PAI-1 Inhibits ApoE Binding to VLDL-R

As discussed above, the inhibition of VLDL binding to VLDL-R by PAI-1 is independent of the affinity of PAI-1 for VLDL-R. The data suggests that this inhibition is dependent on PAI-1 having access to VLDL in solution, since PAI-1:uPA complexes prebound to VLDL-R could not block VLDL binding, whereas incubation of PAI-1 with VLDL in solution did block VLDL-R binding. The simplest explanation for these data is that PAI-1 is blocking VLDL binding to the receptor, not by binding to the receptor but by binding to a receptor ligand on the VLDL particle.

In the case of VLDL, one known ligand for VLDL-R that is present on the VLDL particle is apolipoprotein E (ApoE). It has been shown previously that all three of the common isoforms of ApoE (ApoE2, ApoE3, and ApoE4) bind to VLDL-R with high affinity (Ruiz et al., J. Lipid Res. 46:1721-1731, 2005). Therefore, an experiment was performed to test if PAI-1 is regulating lipoprotein interactions with cellular receptors through interactions with receptor ligands.

To test if PAI-1 could inhibit the binding of ApoE to VLDL-R, surface plasmon resonance (SPR) was used. Immobilized VLDL-R was used, and ApoE (ApoE4 isoform) was co-injected with increasing concentrations of a mutant form of PAI-1 (R76E). [R76E was used because it does not bind to members of the LDL-Receptor family (Stefansson et al., J Biol. Chem. 273:6358-6366, 1998; Lawrence et al., J. Biol. Chem. 272:7676-7680, 1997), and, therefore, the experiment could be carried out to record only the binding of ApoE to VLDL-R.]

Results showed that for the first 300 seconds of the experiment, only the different concentrations of the PAI-1 mutant flowed over the VLDL-R and no binding was seen at any concentration. At 300 seconds, ApoE was injected, either alone or together with the R76E-PAI-1 mutant. As the PAI-1 concentration increased, the binding of ApoE to immobilized VLDR was reduced. The data showed a dose-dependent inhibition of ApoE binding with an $IC_{50}$ of 60.5±6.8 nM. This demonstrates that PAI-1 can inhibit the binding of ApoE4 to the VLDL-R, and further suggests a direct interaction between PAI-1 and ApoE4.

Example 14

PAI-1 Interacts Directly with ApoE

To see if there is a direct interaction with PAI-1 and ApoE, a pull-down experiment was carried out. For this experiment, biotinylated PAI-1 (5 μg/100 μl TBS; Molecular Innovations) or TBS (control) was bound to streptavidin beads (54 Pierce Biotechnology) or control beads (streptavidin without PAI-1) for 45 minutes at 4 C with end over end rotation. The beads were blocked with biotin and washed 4 times for 5 min each with a sodium acetate buffer, pH 5.0 with 150 mM NaCl. The proteins were then eluted with 20 μl of the provided elution buffer (pH 2.8) and neutralized with 1 μl of 1M Tris. 10 μl of each eluant was combined with 3.3 μl of lithium dodecyl sulfate (LDS) sample buffer (Invitrogen) and separated on a 10% Bio-Rad Tris-HCl precast gel. The gel was transferred to PVDF and then blotted for ApoE using the 3H1 mAb. The blot was stripped and reprobed for PAI-1 using a pAb against human PAI-1.

Results of the study demonstrated that only when PAI-1 was present in the pull-down reaction (treated beads) was ApoE precipitated, indicating that PAI-1 interacts directly with ApoE.

Figure 13:
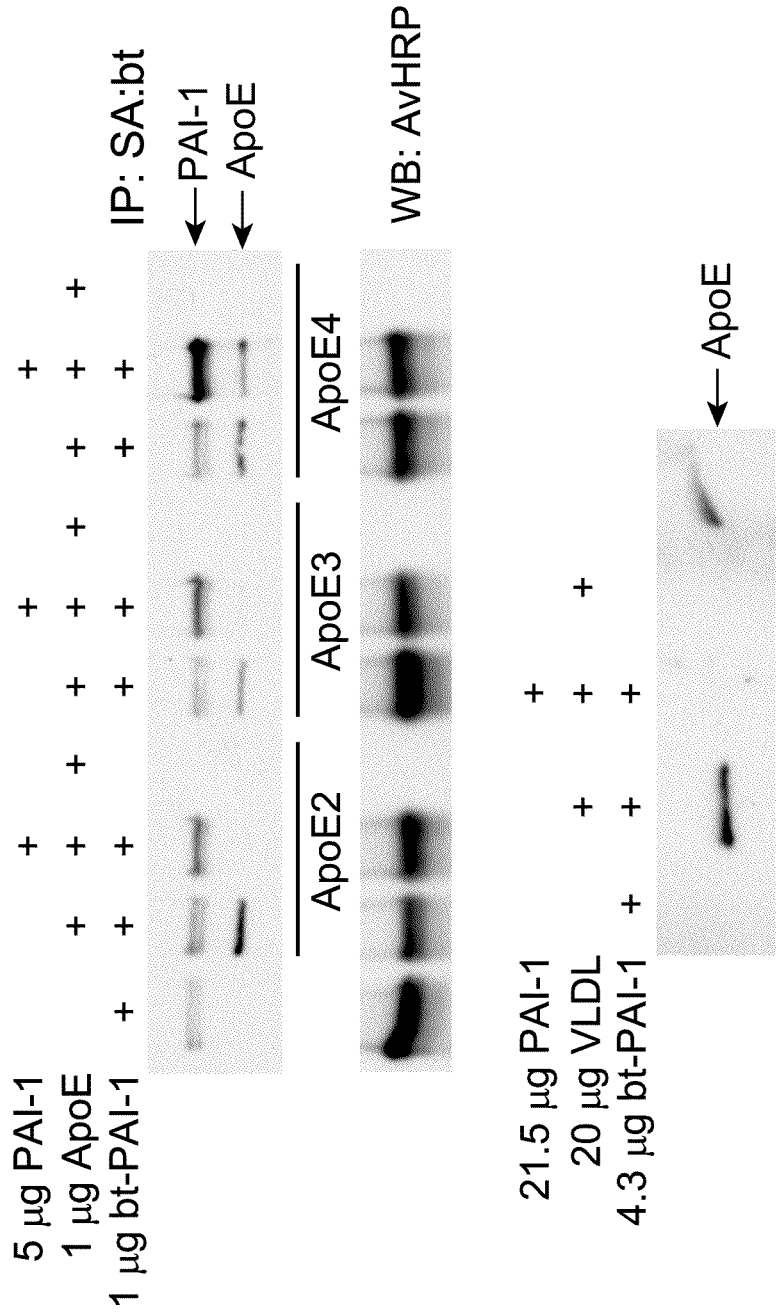
FIG. 13 shows that PAI-1 binds to ApoE isoforms.

To determine if PAI-1 binds different isoforms of ApoE, crosslinking and pull-down studies were carried out with ApoE2, ApoE3, ApoE4, and PAI-1. Biotinylated PAI-1 (bt-PAI-1) in HEPES-buffered saline (HBS), or bt-PAI-1 with a 5-fold excess of unbiotinylated PAI-1, or HBS alone were incubated with ApoE2, ApoE3, or ApoE4 (MBL) or VLDL (Intracel) in a final volume of 100 μl for 1 hour at 37° C. Samples were crosslinked in 5 mM DTSSP (Pierce) for 30 minutes at room temperature and the crosslinker was deactivated by adding 50 mM Tris, pH 7.4. The samples were diluted with 1 volume of HBS with 2% Triton X-100 and 0.2% SDS and then incubated with streptavidin-coated beads for 60 minutes with end over end rotation. Supernatants were collected and the beads were washed 4× with HBS containing 1% Triton X-100 and 0.1% SDS and twice with HBS containing no detergent. Bound proteins were eluted by boiling the beads in Laemmli buffer. The eluants were reduced and separated on 12% gel (Bio-Rad), transferred to PVDF and blotted for ApoE, PAI-1 or biotin. The study showed that PAI-binds ApoE2, ApoE3, ApoE4 (see FIG. 13).

Mutants of PAI-1 are also tested, including mutants that bind vitronectin and the LDL-R family members normally but do not inhibit PAs, and mutants that lack vitronectin binding but retain other functions (Stefansson et al., J. Biol. Chem. 276:8135-8141, 2001; Xu et al., J. Biol. Chem. 279: 17914-17920, 2004). The binding studies are carried out with and without PAI-039. If PAI-039 is affecting the interaction of PAI-1 with ApoE, then PAI-039 treatment will block the association.

These experiments allow for the design of a preliminary map of the binding site for ApoE on PAI-1, because mutants having reduced binding help determine which regions are important for ApoE binding. Likewise, additional pull-down experiments are also carried out with these same forms of PAI-1. A ligand cross-linking strategy followed by high-performance liquid chromatography with tandem mass spectrometry detection (LC-MS-MS) is used to identify the putative binding interface. For these experiments, PAI-1 in its different conformations is biotinylated and allowed to bind to ApoE. The complex is then cross-linked with the reducible homobifunctional and amine-reactive cross-linking agent dithiobis[succinimidylpropionate] (DSP) (Pierce). The cross-linked proteins are then captured with streptavidin beads subjected to tryptic digest either together or after SDS-PAGE without reduction to separate the uncross-linked ApoE and PAI-1. The tryptic fragments are then identified by LC-MS-MS analysis (Proteome Center of the University of Michigan).

Similar cross-linking studies are also carried out with PAI-1 and intact HDL and VLDL. The procedure and analysis are the same except that the non-membrane permeable cross-linking agent 3,3'-dithiobis[sulfosuccinimidylpropionate] (DTSSP) (Pierce) is used to help reduce the potential of the cross-linking agent being sequestered into the lipid core of the lipoprotein particles. The proteins are then detergent extracted from the particles before analysis.

In another set of experiments, PAI-1 is labeled with $^{125}$I-Bolton-Hunter reagent, and the $^{125}$I-PAI-1 is reacted with HDL or VLDL and cross-linked as above. After the extraction step only the $^{125}$I-labeled cross-linked complexes are gel-purified from a low percentage SDS-PAGE. The cross linker is then reduced and the non-radioactive proteins are isolated by another round of SDS-PAGE and analyzed by tryptic digestion and LC-MS-MS. This procedure is carried out to increase the specificity for the cross-linked complex. Together, these experiments identify (i) the site of interaction between PAI-1 and ApoE, and (ii) other lipoproteins present in HDL and/or VLDL that interact with PAI-1.

Example 15

PAI-1 Binds to ApoA and LPL

PAI-1 apparently influences lipid metabolism by interacting with ApoE as set out in Example 14. However, it is also possible that PAI-1 interacts with other protein components of the HDL or VLDL particles or other components on the cell surface. Therefore, a pull-down experiment, similar to the experiment described in Example 14 above, was carried out to determine whether PAI-1 binds ApoA associated with the HDL or VLDL particles.

Because apolipoprotein AI (ApoA-I) and apolipoprotein AII (ApoA-II) are major components of HDL and are directly involved in HDL binding to SR-BI (Xu et al., J. Lipid Res. 38:1289-1298, 1997), they are important candidates for PAI-1 binding. ApoA-I and ApoA-II also mediate the recycling of ApoE in cells (Farkas et al., J. Biol. Chem. 278:9412-9417, 2003; Kockx et al., J. Biol. Chem. 279:25966-25977, 2004). Lipoprotein lipase (LPL) is another important candidate for PAI-1 binding, because it promotes VLDL binding to cells, including macrophages. Moreover, mice that are deficient in the macrophage expression of LPL have reduced plasma ApoE levels, and are markedly protected from the development of atherosclerosis (Eck et al., Atherosclerosis 183:230-237, 2005).

Figure 14:
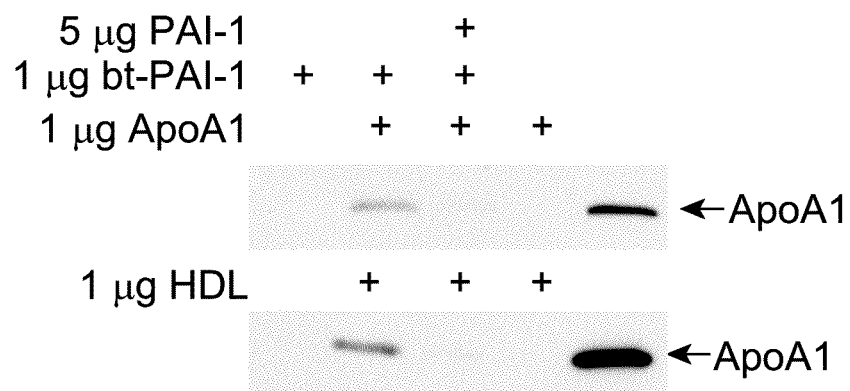
FIG. 14 shows that PAI-1 binds to ApoA1.

To determine if PAI-1 interacts with ApoA1, crosslinking and pull-down studies were carried out with ApoA1 and PAI-1. Biotinylated PAI-1 (bt-PAI-1) in HEPES-buffered saline (HBS), or bt-PAI-1 with a 5-fold excess of unbiotinylated PAI-1, or HBS alone were incubated with ApoA1 (Sigma-Aldrich) or HDL (Intracel) in a final volume of 100 μl for 1 hour at 37° C. Samples were crosslinked in 5 mM DTSSP (Pierce) for 30 minutes at room temperature and the crosslinker was deactivated by adding 50 mM Tris, pH 7.4. The samples were diluted with 1 volume of HBS with 2% Triton X-100 and 0.2% SDS and then incubated with streptavidin-coated beads for 60 minutes with end over end rotation. Supernatants were collected and the beads were washed 4× with HBS containing 1% Triton X-100 and 0.1% SDS and twice with HBS containing no detergent. Bound proteins were eluted by boiling the beads in Laemmli buffer. The eluants were reduced and separated on 12% gel (Bio-Rad), transferred to PVDF and blotted for ApoA1. The study showed that PAI-binds to ApoA1 (see FIG. 14).

Example 16

Characterization of the Binding of PAI-1 to VLDL-R

Previously, it was shown that PAI-1 only binds to LRP with high affinity when it is associated in a complex with a protease (Stefansson et al., J Biol. Chem. 273:6358-6366, 1998; Stefansson et al., J. Biol. Chem. 279: 29981-29987, 2004). However, the binding of PAI-1 to VLDL-R is different than the binding of PAI-1 to LRP, because LRP does not bind latent PAI-1 with significant affinity (Stefansson et al., J Biol. Chem. 273:6358-6366, 1998), whereas latent PAI-1 binds to the VLDL-R with an estimated kDa of ~65 nM. This difference in PAI-1 binding to the VLDL-R and LRP is similar to the difference in the binding of lipid-free ApoE to these two receptors (Ruiz et al., J. Lipid Res. 46:1721-1731, 2005), and suggests that there are functional consequences for these binding differences. Therefore, the aim of this study was to characterize the binding of the different conformational forms of PAI-1 to VLDL-R and compare the binding to that of PAI-1 to LRP.

In an SPR experiment examining the binding of PAI-1 in complex with vitronectin to the VLDL-R, the PAI-1:vitronectin complex was found to bind to the VLDL-R with an approximate kDa of 80 nM. Notably, vitronectin alone did not bind VLDL-R. This finding was unexpected because the vitronectin binding region in PAI-1 is adjacent to the binding region for members of the LDL-R family (Stefansson et al., J Biol. Chem. 273:6358-6366, 1998).

To determine if the PAI-1:vitronectin complex binds to LRP, SPR is also carried out with both LRP and the VLDL-R coupled to separate channels of the same chip. Thus, the same PAI-1 samples are analyzed at the same time. Using this approach, the binding of active, latent, and cleaved, PAI-1 is compared as well as PAI-1 in complex with uPA, tPA, and the PAI-1:vitronectin complex. The effect of PAI-039 on the binding of the different conformational forms of PAI-1 binding to the two receptors is also tested. These experiments are carried out to illustrate any differences in the association of PAI-1 with these receptors and this information is then compared with the results described herein above for the competition binding studies with purified ApoE and with HDL and VLDL binding to the receptors.

Example 17

Characterization of the Effect of PAI-1 on HDL and VLDL Binding to the VLDL-R

These experiments characterize PAI-1 interactions with the major protein components of the RCT pathway. PAI-1 binding to ApoE is proposed as being responsible for the inhibitory effect of PAI-1 on VLDL binding to the VLDL-R, because the PAI-1-R76E mutant inhibited VLDL binding to VLDL-R to the same extent as wild-type PAI-1. Thus, like lipid-free ApoE, the PAI-1-R76E mutant, which is defective in receptor binding, can still block VLDL binding to VLDL-R, very likely through an association with lipid bound ApoE. Together, these experimental findings strongly support the hypothesis that PAI-1 regulates lipoprotein interactions with cellular receptors, but they do not indicate how this interaction with ApoE or VLDL can regulate HDL levels in plasma.

ApoE is known to be a constituent protein of HDL (Vezina et al., J. Lipid Res. 29:573-585, 1988), and recent studies have shown that ApoE secretion from cells, including macrophages, is associated with cholesterol efflux in a process that involves both HDL and ApoA-I (Kockx et al., J. Biol. Chem. 279:25966-25977, 2004; Heeren et al., J. Biol. Chem. 278: 14370-14378, 2003; Heeren et al., Arterioscler. Thromb. Vasc. Biol. 26:442-448, 2006; Matsuura et al., J. Clin. Invest 116:1435-1442, 2006).

To determine whether PAI-1 can affect HDL binding to the isolated VLDL-R directly as it does with VLDL, the present experiments are carried out like those previously described herein with VLDL using fluorescent DiI-HDL (Intracel). If HDL binding to VLDL-R is blocked by the R76E-PAI-1 mutant, this suggests PAI-1 functions via the same mechanism of action, possibly through interaction with HDL-associated ApoE. However, it is also possible that HDL does not bind significantly to the VLDL-R or that it can bind to the VLDL-R, but interactions with other receptors are more important for its ability to transport cholesterol.

Therefore, experiments are also carried out to investigate whether PAI-1 affects the binding of HDL to other receptors, such as LRP-1, or the scavenger receptor BI (SR-BI), which is thought to be a primary HDL receptor on cells (Zannis et al., J. Mol. Med. 84:276-294, 2006; Krieger, J. Clin. Invest 108:793-797, 2001). Recent studies have suggested that LRP may play a role in HDL catabolism in adipocytes (Vassiliou et al., Arterioscler. Thromb. Vasc. Biol. 24:1669-1675, 2004). The analysis with LRP is carried out exactly like that with the VLDL-R, and includes experiments using purified ApoE, HDL and VLDL.

Initially, pull-down studies and cross-linking analyses are carried out with purified SR-BI in reconstituted phospholipid/cholesterol liposomes as described (Liu et al., J. Biol. Chem. 277:34125-34135, 2002) to determine PAI-1 binding to SR-BI.

Experiments with SR-BI are limited to the analysis of the of SR-BI in liposomes because, unlike the members of the LDL-R family of receptors which have a single transmembrane domain and an ectodomain that can be shed from the cell in a ligand binding competent form, SR-BI is a member of the CD36 receptor family. The CD36 receptor family has horseshoe-like membrane topologies with both amino- and carboxy-terminal transmembrane domains, which has not been shown to be functional in membrane-free studies.

SR-BI is expressed in the *Drosophila* S2 cell expression system with an epitope tag for purification as described (Liu et al., J. Biol. Chem. 277:34125-34135, 2002). This cell expression system is remarkably efficient and routinely produces high yields of protein in serum-free growth media. The present experiment is designed to examine whether PAI-1 can interfere with VLDL or HDL binding to SR-BI by binding to the lipoprotein particle.

To determine whether PAI-1 can also regulate the association of HDL and VLDL to SR-BI, PAI-1 is reacted with SR-BI containing liposomes or liposomes alone (control), and the liposomes are separated by centrifugation. If PAI-1 binds to the receptor, it fractionates specifically with the SR-BI liposomes. The association of DiI-labeled HDL or VLDL to SR-BI and the ability of PAI-1 to disrupt this binding is also tested with fluorescently labeled SR-BI monitored by FACs analysis.

Briefly, the purified SR-BI is labeled with Alexa Fluor 488 and then reconstituted into liposomes. The fluorescent green SR-BI is then mixed with the red DiI-VLDL or DiI-HDL with or without increasing concentrations of competing proteins and the samples are subjected to FACs analysis. When DiI-VLDL or DiI-HDL binds to SR-BI, there is a shift in the forward and side scatter of the liposomes and an overlap of the red and green fluorescent signals. Likewise, if PAI-1 competes for HDL and or VLDL binding to SR-BI, there are reductions in the changes in forward and side scatter of the particle and in the overlap of the fluorescent signals. For these studies PAI-1 in the active, latent, cleaved and protease complexed conformations, as well as PAI-1 bound to vitronectin, and the PAI-1 mutants are tested for their ability to inhibit lipoprotein particle binding.

In addition to SR-BI, HDL is also thought to interact with the ABC transporters, ABCA1 and ABCG1, on the cell surface and this association is critical for cholesterol efflux to HDL (Cuchel et al., Circulation 113:2548-2555, 2006). It previously has been shown that the ABCA1 protein can be expressed in *Drosophila* cells, purified, and reconstituted in liposomes into a functional ATPase (Takahashi et al., J. Biol. Chem. 281:10760-10768, 2006). Thus, ABCA1 and ABCG1 are expressed in insect cells with an epitope tag for purification and each protein is reconstituted into liposomes as described for SR-BI herein above. Briefly, the analysis with each of these proteins is carried out like that for SR-BI, as described herein above. ABCA1 and ABCG1 are labeled with Alexa Fluor 488 and FACs analysis is carried out. Likewise, direct binding of PAI-1 is also carried out.

Example 18

The Role of PAI-1 in Cellular Catabolism of VLDL and HDL

Preliminary studies indicate that wild-type mice and PAI-1−/− mice have significantly different plasma lipid profiles when fed a standard chow diet. Because macrophages play an integral role in tissue cholesterol homeostasis and are a major source of PAI-1 in atherosclerotic lesions, macrophages may be an important cell type where cross-talk between PAI-1 and lipid metabolic pathways occurs. To understand how PAI-1 regulates RCT, studies were designed to investigate the role of PAI-1 in macrophage lipid metabolism.

First, HDL and VLDL binding and uptake in PAI-1−/− macrophages was analyzed in primary peritoneal macrophages from wild-type mice and PAI-1−/− mice. To harvest macrophages, mice were injected on day 1 (8-12 weeks old) intraperitoneally with 1.0 ml of sterile 5% thioglycollate (TG) broth (27 G needle ½" long). On day 5, mice were sacrificed and undergo peritoneal lavage to harvest macrophages. (Macrophage isolation is also described by Cao et al. (Blood 106: 3234-3241, 2005).) Isolated macrophages were incubated with fluorescent DiI-VLDL or DiI-HDL.

Macrophages from PAI-1 null mice bind and take-up significantly more VLDL (~25%) than do wild-type macrophages. Likewise, DiI-HDL binding and uptake was also elevated in PAI-1 null mice (~10%), but this difference failed to reach statistical significance (p=0.06) in at least preliminary experiments. These data are consistent with the data for the in vitro studies set out herein above, which indicate that PAI-1 can block VLDL binding to VLDL-R. The data also indicate that VLDL and possibly HDL binding and/or uptake by macrophages is mediated by a ligand-receptor pair that can be modulated by PAI-1.

Experiments were then carried out to determine whether a VLDL-R antagonist, the low density lipoprotein Receptor-Associated Protein (RAP), could block binding and uptake of VLDL and/or HDL. RAP is a general antagonist of members of the LDL-R family, including the VLDL-R (Bu, Curr. Opin. Lipidol. 9:149-155, 1998). RAP can block the association of VLDL with both wild-type and PAI-1−/− macrophages. However, RAP had no affect on HDL binding (data not shown). This result is consistent with the in vitro data set out herein above, but it does not prove that RAP is specifically blocking binding to VLDL-R. Additional experiments are contemplated to identify the specific receptor(s) that is responsible for this binding, and if it is the binding to this receptor that is sensitive to regulation by PAI-1.

The binding of lipoproteins to cell surfaces is complex and involves multiple ligands on the lipoprotein particles and multiple receptors on the cell surface, as well as interactions with other factors such as lipoprotein lipase (LPL), and cell surface glycosaminoglycans (GAGs) (heparan sulfate proteoglycans). Therefore, a number of experiments were designed to identify the RAP-sensitive receptor and to characterize its relationship to the PAI-1 regulation of VLDL, and possibly HDL, binding.

First, peritoneal macrophages are isolated from VLDL-R−/−, and LDL-R−/−, mice; LRP null macrophages are also isolated from tissue-specific conditional LRP knockout mice, LRPlox/lox mice, (Cao et al., EMBO J. 25:1860-1870, 2006). LRPlox/lox mice carry an LRP allele into which loxP sites have been integrated (Rohlmann et al., J Clin. Invest 101:689-695, 1998). To generate a deletion of the LRP gene in macrophages, LRPlox/lox mice are crossed with LysM-cre transgenic mice (Jackson Laboratories), which express the Cre recombinase in macrophages and granulocytes (Boucher et al., Science 300:329-332, 2003; Clausen et al., Transgenic Res. 8:265-277, 1999). While complete deletion of the LRP gene results in embryonic lethality (Herz et al., Cell 71:411-421, 1992 [published erratum appears in Cell 73:428, 1993]), the deletion of LRP macrophages yields viable mice. Once the animals are bred and produced, they are used together with the VLDL-R−/− and LDL-R−/− mice to isolate peritoneal macrophages. VLDL and HDL binding and responsiveness to RAP is then tested in the cells and compared to wild-type cells.

Each of the mouse strains described herein above are then crossed with PAI-1−/− mice to make double knockouts for similar experiments to examine the importance of each receptor for the increased binding of VLDL (and possibly HDL) observed in the PAI-1−/− cells. In addition, peritoneal macrophages are obtained from SR-BI−/− mice. This latter receptor is not thought to be RAP sensitive; however, as noted above, it is a major HDL receptor and therefore analysis of the binding of HDL and VLDL to these cells, with and without RAP and/or PAI-1, will be tested. The SR-BI−/− mice (Jackson Laboratories) are also crossed with the PAI-1−/− mice to make double knockouts. Colonies of VLDL-R−/−, LDL-R−/−, PAI-1−/−, and LRPlox/lox mice are bred and maintained in the lab.

All of the mice have been backcrossed at least 8 generations into C57/B6J, except for the LRPlox/lox mice. Therefore, in all experiments with the LRPlox/lox mice, heterozygous Cre-expressing mice are bred with homozygous LRPlox/lox mice and sibling controls are used. The expression of VLDL-R, LDL-R, LRP, and SR-BI is examined in wild-type macrophage cultures by the use of antibodies and by quantitative PCR (qPCR). PAI-1 expression in the cell culture media is measured by an antigen assay in Core B and by qPCR.

Example 19

The Role of PAI-1 in Regulating Lipoprotein Binding and Uptake by Macrophages

To establish the role of PAI-1 in regulating VLDL and HDL association with macrophages, experiments are carried out to assess the binding, at 4° C., and uptake, at 37° C. of both DiI-VLDL and DiI-HDL in the macrophages of each of the double PAI-1−/− receptor−/− mouse genotypes (receptor wild-type, VLDL-R−/−, LDL-R−/−, LRP−/−, and SR-B1−/−). By crossing each of these receptor null mice into PAI-1 null mice, the potential to see specific effects of PAI-1 is maximized.

Binding and uptake of VLDL and HDL is determined in macrophages ±wild-type PAI-1 in the different conformational forms including active, latent, protease-complexed, and vitronectin-complexed. These data are then compared to the results from the in vitro studies. Also, depending on the results obtained with the PAI-1 mutants in the in vitro binding studies discussed above, competition by any of the PAI-1 mutants that give informative results in the in vitro assay is further examined. These competition binding studies include use of mutants that inhibit lipoprotein binding better than wild-type PAI-1, or mutants that are unable to block binding, but at a minimum, competition binding studies with the R76E PAI-1 mutant are carried out.

The effects of other potential regulators of lipoprotein binding to the cells are also examined with and without added PAI-1. Such potential regulators include LPL, which has been reported to stimulate lipoprotein binding to cells, and heparin, which inhibits lipoprotein binding through inhibition of glycosaminoglycan binding. It is possible that PAI-1 is modulating the interaction with one of these regulators or "co-receptors". If PAI-1 alters lipoprotein binding and/or uptake at the level of a cell receptor, then there should be a loss of PAI-1 sensitivity in the corresponding receptor knockout cells, suggesting that PAI-1 is regulating lipoprotein binding either directly through interaction with that receptor or with a ligand for that receptor that is present on the affected lipoprotein particle.

Example 20

The Effect of PAI-1 Inactivating Agents on Lipid Uptake in Macrophages

The inactivation of PAI-1 by the genetic deletion of PAI-1 led to increased binding/uptake of both VLDL and HDL in macrophages compared to wild-type. Therefore, it stands to reason that the inactivation of PAI-1 using small molecule inhibitors produces the same effect. Consequently, experiments are designed to treat macrophages in cell culture with PAI-1 inactivating compounds to determine the effect on lipoprotein binding and uptake using methods similar to those described herein above. Cells derived from wild-type animals should be affected, but that effect should be lost in cells from PAI-1−/− mice. There is some precedent for the use of PAI-1 inhibiting molecules in cell culture, because PAI-039 affects adipocyte differentiation (Crandall et al., Arterioscler. Thromb. Vasc. Biol. 26: 2209-2215, 2006).

Thus, cells are treated overnight with increasing concentration of PAI-039 after which VLDL and HDL binding and uptake are measured. It is contemplated that PAI-1 inhibitors such as, but not limited to, PAI-039 and the other PAI-1 inhibitors of the invention increase binding and uptake of both VLDL and HDL in macrophages.

Example 21

The Role of PAI-1 in Foam Cell Formation and RCT

Macrophage foam cell formation occurs following uptake of excess cholesterol from circulating triglyceride rich lipoprotein remnants, and following phagocytosis of cells or parts of cells whose membranes contain large amounts of cholesterol. RCT from macrophages by HDL returns cholesterol to the liver where it may be excreted in the bile. The removal of cholesterol from macrophages appears to be particularly important for protection against atherosclerosis, whereas efflux of cholesterol from other peripheral tissues may comprise the greatest mass of cholesterol in RCT. It has been hypothesized that RCT is more efficient in PAI-1−/− macrophages than in macrophages from wild-type mice. Thus, this experiment was designed to determine the role of PAI-1 in foam cell formation and RCT using macrophages from PAI-1 null mice and PAI-1 inactivating drugs.

Macrophages, preincubated with unlabeled oxLDL for 1 hour, increased DiI-HDL binding/uptake over 3-fold in both wild-type and PAI-1−/− cells. Peritoneal macrophages were isolated and plated and pretreated with 20 µg/ml of oxLDL in RPMI-0.5% BSA for 1 hour. DiI HDL (10 µg/ml) was then added and incubated for 2 hours. Cells were rinsed, fixed, DAPI stained, and then fluorescent intensity was measured.

This experiment demonstrated a small but significant elevation of DiI HDL binding following oxLDL pretreatment in PAI-1−/− macrophages compared to wild-type cells. This is consistent with the hypothesis that RCT from PAI-1−/− macrophages may occur more efficiently. Therefore, experiments were designed to study both cholesterol efflux and ApoE recycling in preloaded macrophages (Kockx et al., J. Biol. Chem. 279:25966-25977, 2004; Hasty et al., Lipid Res. 46:1433-1439, 2005).

To measure cholesterol efflux, peritoneal macrophages are preloaded with $^{3}$H-cholesterol from AcLDL (Intracel). Cholesterol efflux is measured following ApoA-I (PeproTech) treatment. Efflux of ApoE from macrophages can occur in response to both ApoA-I, as well as ApoE, and both proteins are utilized to stimulate ApoE efflux. If PAI-1−/− macrophages are indeed more capable of RCT, then there should be a greater cholesterol efflux and greater ApoE efflux from these cells when compared to wild-type macrophages.

Example 22

The Role of PAI-1 in Adipocyte Lipid Metabolism

Lipoprotein binding and uptake on adipocytes is highly dependent on cell surface GAGs, as well as endocytic receptors and lipid transporters. To examine lipoprotein binding on adipocytes, binding/uptake of DiI-VLDL and DiI-HDL was carried out in adipocytes five days post-differentiation.

3T3-L1 cells were cultured in DMEM/10% BCS in a 12-well dish (50,000 cells/cm$^{2}$). Two days after reaching confluency, cells were incubated in Differentiation Media (ZenBio) for 3 days and then in Adipocyte Maintenance Media (ZenBio). After 5 days of lipid accumulation, adipocytes were rinsed in DMEM-0.5% BSA and incubated with 10 µg/ml of DiI-labeled VLDL or HDL for 3 hours with either no addition or RAP (50 µg/ml) in DMEM-0.5% BSA. Cells were rinsed, fixed, and DAPI-stained. Images were taken with a Nikon TE2000 and MetaMorph software. Fluorescence was measured and expressed as mean±SEM RFU from a duplicate determination (*$p<0.05$ compared to control (no RAP) treatment). Binding/uptake of both labeled fluorophores after 3 hours of incubation was inhibited by the receptor antagonist RAP. Thus, RAP inhibited VLDL and HDL binding in adipocytes.

To determine how the binding and uptake of labeled lipoproteins is altered by various forms of PAI-1, the binding and uptake of HDL and VLDL by murine adipocytes is measured in the presence and absence of various forms of PAI-1. Mature adipocytes (5-10 days post-differentiation) are incubated with increasing concentrations of PAI-1 (wild-type active, latent, cleaved, PA-complexed, active site-deficient, vitronectin binding-deficient, LDL-R family binding-deficient) and binding and uptake of the labeled lipoproteins is measured. 3T3-L1 adipocytes express PAI-1 and release it into the medium. For this reason, it may be necessary to carry out these experiments in adipocytes differentiated from preadipocytes collected from wild-type and PAI-1−/− mice (as described herein below).

To further understand the role of PAI-1 in lipid metabolism, adipocyte lipid metabolism is measured in PAI-1−/− cells and with PAI-1 inactivating drugs. Preadipocytes are isolated from the epididymal fat pads of mice (the same animals as used in the experiments described herein above). To obtain fat pads, mice are euthanized and epididymal white fat pads excised, weighed, and rinsed in an isolation buffer (120 mM NaCl, 0.5 mM KCl, 1.2 mM $KH_2PO_4$, 0.6 mM $MgSO_4.7H_2O$ and 0.9 mM $CaCl_2.6H_2O$, 20 mM HEPES, 200 mM adenosine, and 2.5% BSA). Fat pads are then cut into small pieces in isolation buffer supplemented with 1 mg/mL type I collagenase (Worthington Biochemical Corp., Lakewood, N.J.) and digested at 37° C. in shaking water bath at 100 rpm per minute for 45 minutes. The digested adipose tissue is then filtered through 100 μm mesh (TETKO Inc., Briarcliff Manor, N.Y.) to obtain a single cell suspension of cells rinsed with isolation buffer. The adipocytes are matured using the same methods as for 3T3-L1 cells (as set out above). Binding and uptake of labeled lipoproteins is assessed in matured adipocytes by treating with vehicle or increasing concentrations of either PAI-039 or another small PAI-1 inactivating molecule from the drug screen (as set out herein above). The inactivation of PAI-1 should result in greater binding of the lipoproteins to the cell surface and possibly greater uptake.

Because large differences in lipid profile were seen between the PAI-1−/− and wild-type mice, cholesterol efflux from adipocytes is measured based on the methods of Le Lay et al (J. Lipid Res. 44:1499-1507, 2003). Adipocytes (five days after differentiation) are incubated with $^3$H-cholesterol under serum free conditions. After rinsing out unincorporated $^3$H-cholesterol, cells are incubated with ApoA-I and cholesterol efflux is measured by the $^3$H released in the media compared to the addition of no ApoA-1. It is expected that a greater efflux occurs in adipocytes from PAI-1−/− animals, which could, in part, explain the differences observed in serum cholesterol levels, particularly HDL and total cholesterol between these two genotypes.

The infiltration of adipose tissue by macrophages in obesity leads to inflammatory changes in adipose tissue, including expression of inflammatory cytokines. These changes are thought to reduce insulin sensitivity and lead to a diabetic phenotype. Recent cell culture studies using adipocytes and macrophages (Suganami et al., Arterioscler. Thromb. Vasc. Biol. 25:2062-2068, 2005) have shown that whether cultured together or treated with media from the other cell type, adipocytes and macrophages release greater levels of proinflammatory factors, such as MCP-1, IL-6 and TNF-α☐ but lesser levels of the anti-inflammatory molecule adiponectin. PAI-1-deficient mice were protected from high-fat diet induced obesity and insulin resistance (Ma et al., Diabetes 53:336-346, 2004), suggesting that macrophage infiltration or the usual inflammation that accompanies this infiltration may be decreased in the absence of PAI-1. Therefore, a PAI-1 deficiency may be protective for development of obesity and insulin resistance by decreasing expression and secretion of inflammatory mediators in adipose tissue. Therefore, to determine the role of PAI-1 in obesity and/or insulin resistance, differentiated adipocytes and peritoneal macrophages were co-cultured.

3T3-L1 cells were cultured as described herein above. Adipocytes were rinsed and kept in DMEM-0.5% BSA. Peritoneal macrophages ($6 \times 10^5$ cells/well) from wild-type PAI-1 null mice, or no cells were added. After two days in culture, cell were rinsed, fixed, washed, and stained with Oil Red O. Unbound dye was removed and nonspecific binding was blocked before incubating with α-mouse-CD-11B. The primary antibody was detected with Alexa-488-conjugated α-rat IgG and cells were DAPI-stained. Cells were photographed at 20× with a Nikon TE2000 and Metamorph software. TNF-α, was quantified using a 0 kit. Data represent mean±SEM of a duplicate determination. The macrophages in each well were quantified based on the Alexa 488 signal over the blank (ex 490 nm; em 530 nm; cutoff 515 nm).

The adipocytes clearly contained lipid droplets and adherent macrophages were easily visualized. In addition, the preliminary experiment suggests that macrophages from wild-type mice release more TNF-α, than macrophages from PAI-1−/− mice in the presence of differentiated 3T3-L1 cells.

Primary preadipocytes from wild-type and PAI-1−/− mice are isolated and then differentiated similarly to 3T3-L1 cells. The cells are then cultured and adipocytokines (adiponectin, IL-6, MCP-1, resistin, TNF-α, and total PAI-1) are measured after culture in the presence of absence of peritoneal macrophages collected from wild-type and PAI-1−/− mice. All combinations of adipocytes and macrophages are studied and the adipocytokines (adiponectin, IL-6, MCP-1, resistin, TNF-α and total PAI-1) are measured.

Example 23

The Characterization of Lipid Profiles in Mice Lacking PAI-1, uPA, tPA, and Vitronectin Mice lacking PAI-1 have higher total cholesterol levels compared to wild-type mice, primarily due to their higher HDL levels. PAI-039 treatment raises HDL levels and lowers VLDL levels, but only in mice that express PAI-1. These data strongly support the hypothesis that PAI-1 plays a direct role in lipid metabolism. It is possible, however, that the PAI-1 effect is not direct, but indirect via some factor that PAI-1 regulates. Therefore, plasma lipid profiles in mice that lack the principal protease targets of PAI-1, uPA, tPA, and the double uPA/tPA nulls are measured. If the changes in lipid levels observed in the PAI-1−/− mice are due to unregulated proteolytic activity by uPA and/or tPA, then lipid levels in these null strains should either be normal or should show an opposite profile to the PAI-1−/− mice, such as reduced HDL. Alternately, if PAI-1 is acting on an unrelated factor, such as ApoE or another apolipoprotein or receptor, then the presence or absence of proteases would be expected to have little effect on plasma lipid profiles. If the protease-deficient mice show the same lipid profiles as wild-type mice, PAI-1 is most likely influencing lipid levels through interaction with another factor.

Plasma lipid profiles in mice that lack the PAI-1 cofactor, vitronectin, are also measured. Because vitronectin stabilizes plasma PAI-1 and because in vitronectin null mice plasma PAI-1 is undetectable under non-pathologic conditions, plasma lipid profiles may be particularly informative regarding the site of PAI-1's action on lipid metabolism. However, these mice express PAI-1 normally in their tissues, and the tissue levels of PAI-1 may be more analogous to normal levels than would be predicted based on measurements of plasma PAI-1. Accordingly, if PAI-1 is acting primarily locally in the tissue, then the vitronectin status of the mice would not be expected to affect the lipid profiles. However, if PAI-1 is acting via the blood, the vitronectin null mice should have a lipid profile very similar to PAI-1−/− mice.

In all of the experiments set out above, six mice per group of age-matched, 9-12 week old, male mice null for either uPA, tPA, double uPA/tPA or vitronectin are used. All strains are available and are back crossed into C57BL/6J at least eight generations. These groups are likewise compared to wild-type C57BL/6J mice and to PAI-1−/− mice. The mice are kept in micro-isolation cages on a 12 h day-night cycle with water and standard mouse chow ad libidum.

After two weeks, blood is collected for a full lipid panel analysis, including total cholesterol, triglycerides, HDL, VLDL, and LDL. An aliquot of blood from each animal is also stored at −80° C. for further analysis as needed. Each experiment is repeated 3 times. If there are significant variations in lipid levels within groups, then the same protocol is to be repeated, except that mice are fasted overnight prior to the blood draw. Together, these experiments should provide information as to whether PAI-1 is acting through the inhibition of plasminogen activators and/or if vitronectin influences PAI-1 activity.

Example 24

The Effect of Novel PAI-1 Inhibitors on Lipid Profiles In Vivo

PAI-039 and various novel PAI-1 inactivating agents are tested in vivo in various transgenic knock-out or knock-in mice to determine their effects on lipid profiles in vivo. Plasma lipid profiles in mice that lack PAI-1, uPA, tPA, uPA and tPA, and vitronectin are measured after treatment with PAI-039 or any other PAI-1 inhibitor compound of the invention (as disclosed herein) for the two week period of the experiment. PAI-039 or other PAI-1 inhibitor compound (as disclosed herein) is formulated into the mouse chow at 5 mg/gram of chow, as in the experiments set out herein above, and feeding and analysis is also the same as described in experiments described herein.

If PAI-1 is acting through inhibition of tPA and mice lacking tPA show an opposite phenotype from PAI-1 null mice, i.e. decreased HDL levels, then treatment of tPA null mice with PAI-039 or other PAI-1 inhibitor compound (as disclosed herein) should have no effect on plasma lipid levels in these mice. Conversely, if PAI-1 is acting on a non-plasminogen activator protein, then even in the protease null background, drug treatment should be fully effective and raise HDL levels.

The same scenario should be true with the vitronectin null mice. For example, if mice lacking vitronectin show an opposite phenotype from PAI-1−/− mice, with decreased HDL levels, then treatment of vitronectin null mice with PAI-039 or other PAI-1 inhibitor compound (as disclosed herein) should have no effect on plasma lipid levels in these mice. Alternately, if PAI-1's action is vitronectin-independent, then even in vitronectin null mice, drug treatment should be effective and raise HDL levels.

In order to probe the mechanism of PAI-1's regulation of lipid metabolism in vivo, a series of experiments are carried out with PAI-039 or other PAI-1 inhibitor compound (as disclosed herein) treatment of mice either (i) over-expressing wild-type or stable murine PAI-1, or (ii) expressing murine PAI-1 at normal levels, but expressing a form of PAI-1 with single functional sites ablated. These latter experiments utilize three specific PAI-1 knock-in strains, wherein the gene coding for native PAI-1 has been replaced with PAI-1 containing mutations that either disable the protease inhibitory activity only, or disable the PAI-1 interaction with vitronectin or with members of LDL-R family.

The mice over-expressing wild-type murine PAI-1 have been previously described (Eitzman et al., Blood 87:4718-4722, 1996; Eitzman et al., J. Clin. Invest 97:232-237, 1996). These mice drive PAI-1 expression from a CMV promoter and have plasma PAI-1 levels ~100-fold over normal levels (Stefansson et al., J. Biol. Chem. 276:8135-8141, 2001). A second set of mice will be expressing a stabilized form of murine PAI-1 that is based on a stabilized variant of human PAI-1 (14-1b) (Berkenpas et al., EMBO J. 14:2969-2977, 1995), with expression driven by a composite CMV enhancer/β-actin promoter (Sawicki et al., Exp. Cell Res. 244:367-369, 1998).

The initial analysis of these mice is set out to compare their baseline plasma lipid profiles to the profiles of wild-type mice and PAI-1−/− mice. These studies follow the same protocol as set out above with the uPA and tPA null mice. If PAI-1 is regulating lipid metabolism in wild-type mice, then the ~100-fold over-expression of wild-type PAI-1 in the transgenic mice should demonstrate a significant reduction in HDL levels compared to wild-type mice and an even greater reduction compared to PAI-1−/− mice.

The treatment of these mice with PAI-039 or other PAI-1 inhibitor compound (as disclosed herein) is also examined (using the treatment protocol as set out herein above), and its effects on lipid profiles in these mice is evaluated for its efficacy in reducing the extreme levels of PAI-1 in these mice. By comparing these mice, with and without drug treatment, to wild-type mice and PAI-1 null mice, with and without drug treatment, one can determine whether there is a direct in vivo correlation between plasma PAI-1 levels and plasma lipid profiles.

The plasma lipid profiles of the transgenic mice over-expressing the stable PAI-1 are also examined, with and without drug treatment, and these mice serve as another control for the efficacy of the drug or candidate compound to alter lipid profiles in a PAI-1-specific manner, since previous work with the human form of this stable variant of PAI-1 (14-1b) indicates that this PAI-1 mutant is resistant to inhibition by PAI-039 (not shown). Thus, it is likely that in these mice the drug will not be effective at altering lipid profiles.

The knock-in mice to be used in these studies are all on the murine PAI-1 background expressed from the native PAI-1 locus. This means that the knock-in genes expressed by the mice are murine PAI-1 proteins (as opposed to human or some other species) and that their expression is driven at the genetic locus where murine PAI-1 normally resides in the mouse genome. These studies follow the same protocol as set out herein above. The three knock-in strains are described herein below.

The first knock-in strain: 1-PAI-1 with two substitutions/mutations that disable the protease inhibitory activity only. The substitutions are T333R and A335R, and these mutations have been shown to specifically disrupt PAI-1 inhibitory activity (Stefansson et al., J. Biol. Chem. 276:8135-8141, 2001). The second knock-in strain: 2—are mice with two mutations that specifically disable the PAI-1 interaction with vitronectin, the mutations are R101A and Q123K. The third knock-in strain: 3—are mice that have a single mutation that specifically disables the PAI-1 interaction with members of LDL-R family R76E. Each of these mutations and their functional consequences have been described previously (Xu et al, J. Biol. Chem. 279:17914-17920, 2004), and the latter two strains have been produced by Dr. Victoria Ploplis of the University of Notre Dame. Each of these strains has either been constructed in the C57BL/6J background or has been backcrossed in this background.

These mice are used to probe the mechanism of PAI-1's regulation of lipid metabolism by analyzing the effect of PAI-039 treatment on plasma lipid profiles in mice with these single functions ablated. These studies follow the same protocol as set out herein above, with each strain being fed mouse chow with or without PAI-039 for two weeks. Plasma lipid profiles of each strain are then compared to wild-type C57BL/6J and PAI-1−/− mice (also, with or without PAI-039 treatment).

If the interaction of PAI-1 with any of the proteases, vitronectin, or the LDL-R family of receptors is critical for its activity in lipid metabolism, then this effect should be apparent in the strain with that critical function ablated, as these mice having lipid profiles similar to PAI-1−/− mice. Likewise, the identified strain should no longer respond to drug treatment. However, if PAI-1 is interacting with a previously unidentified ligand through a novel mechanism, then the lipid metabolism profiles in these mice should be indistinguishable from wild-type mice, either with or without drug treatment.

Example 25

The Effect of Novel PAI-1 Inhibitor Compounds on Lipid Profiles In Vivo

The lipid profiles in transgenic knockout mice lacking VLDL-R, SR-BI, ApoE, and ApoA-I are examined after treatment with PAI-039 or other PAI-1 inhibitor compound (as disclosed herein). If PAI-1 is exerting its effect on plasma lipid levels through its association with ApoE, or potentially other lipoproteins or receptors, then the treatment of mice lacking ApoE with PAI-039 or other PAI-1 inhibitor compound (as disclosed herein) should not alter plasma lipid levels. Therefore, the effect of PAI-039 or other PAI-1 inhibitor compound (as disclosed herein) treatment on mice genetically deficient in lipoproteins ApoE, ApoA-I, and the receptors, VLDL-R and SR-BI is investigated in these experiments.

VLDL-R null mice, ApoE null mice, SR-BI null mice and ApoA-I null mice have all been backcrossed into the C57BL/6J background. Plasma lipid profiles of each of these strains is compared to wild type C57BL/6J and PAI-1 null mice with or without PAI-039 treatment. PAI-039 is formulated into mouse chow at 5 mg/gram as set out herein above. VLDL-R, SR-BI, ApoE, and ApoA-I were chosen for the initial analysis because all are thought to be important in RCT. Specifically, PAI-1 interacts with purified ApoE and with VLDL, and PAI-1 blocks VLDL binding to the purified VLDL-R. Likewise, the importance of ApoA-I and SR-BI in specifically regulating HDL metabolism and RCT is well established (Zannis et al., J. Mol. Med. 84:276-294, 2006; Krieger, J. Clin. Invest 108:793-797, 2001). These experiments should confirm whether PAI-1 can regulate the activities of any of ApoE, ApoA-I, VLDL-R and SR-BI.

Example 26

PAI-1 Binds to ApoA1 in HDL and Inhibits Cholesterol Efflux from Macrophages

PAI-1 binds directly to HDL via ApoA1. Moreover, PAI-1 can inhibit cholesterol capture from macrophages by HDL or purified ApoA1. In preliminary studies, it was shown that by reducing PAI-1, either genetically or pharmacologically, plasma HDL levels increased. However, the mechanism of this increase was not identified. It was hypothesized that the inverse correlations between PAI-1 levels and plasma HDL, and increased PAI-1 synthesis and reduced RCT in macrophages was due to PAI-1 regulation of HDL interactions with macrophages, which leads to lower levels of plasma HDL and reduced RCT. To test this hypothesis, ApoA1 crosslinking and pull-down studies with biotinylated PAI-1 and purified human HDL were carried out.

Biotinylated stable PAI-1 (Bt-PAI-1) 1 μM in HEPES-buffered saline (HBS), or Bt-PAI-1 with a 5-fold excess of unbiotinylated PAI-1, or HBS alone were incubated with A: 20 μg of HDL (Intracel) or B: 20 μg ApoA1 (Sigma-Aldrich) in a final volume of 100 μl for 1 hour at 37° C. Samples were crosslinked in 5 mM DTSSP (Pierce) for 30 minutes at room temperature and the crosslinker was deactivated by adding 50 mM Tris, pH 7.4. The samples were diluted with 1 volume of HBS with 2% Triton X-100 and 0.2% SDS and then incubated with streptavidin-coated beads (Av) for 60 minutes with end over end rotation. Supernatants were collected and the beads were washed 4x with HBS containing 1% Triton X-100 and 0.1% SDS, and twice with HBS containing no detergent. Bound proteins were eluted by boiling the beads in Laemmli buffer. The eluants were reduced and separated on 4-15% gel (Bio-Rad). The gels were stained with Sypro Ruby (Invitrogen), and the proteins were visualized under UV light.

Stable human PAI-1 can be cross-linked specifically to a single protein present on the HDL particle with a molecular weight of approximately 25 kDa. The specificity of this interaction is demonstrated by the observations that the band is not pulled-down in the absence of PAI-1 and that the cross-linking can be competed by unbiotinylated PAI-1. This 25 kDa band was excised from the gel and subjected to a trypsin digest and mass spectra analysis, which unambiguously identified the protein as apolipoprotein A1 (ApoA1).

To confirm this result, cross-linking studies with purified ApoA1 were carried out. Just as with HDL, the biotinylated PAI-1 specifically cross-linked to purified ApoA1, as the cross-linking could be competed by unbiotinylated PAI-1 and no pull down was observed in that absence of PAI-1. Together, these data demonstrate that PAI-1 interacts directly with ApoA1 in the HDL particle.

Example 27

PAI-1 Inhibits Both HDL and ApoA1-Mediated Cholesterol Efflux from Macrophages

To test whether the binding of PAI-1 to ApoA1 affects RCT, experiments were carried out to examine if PAI-1 regulates the ability of HDL or purified ApoA1 to capture cholesterol from macrophages that had been previously loaded with acetylated-LDL. For these studies thioglycollate-elicited peritoneal macrophages were isolated from wild-type C57BL/6J mice, placed in culture, and loaded with acetylated-LDL for 24-48 hours. Experiments were then undertaken with a dose response of either HDL or purified ApoA1 and the efflux of cholesterol into the media was analyzed.

Peritoneal macrophages were isolated by lavage with cold PBS 4 days after IP injection of 1 ml of 5% thioglycollate. Following RBC lysis, cells were plated to a density of $3 \times 10^5$/$cm^2$ in 24-well plates in RPMI 1640-10% FBS (Invitrogen), and cultured for 5-24 hours. The cells were rinsed twice with RPMI 1640 and loaded with acetylated-LDL (50 μg/ml, Intracel) in RPMI 1640-0.5% FBS for 24-48 hours. The cells were rinsed twice with RPMI 1640 and incubated with either purified human ApoA1 (Sigma-Aldrich) or human HDL (Intracel) and increasing concentrations of stable PAI-1. Thus, the effect of PAI-1 on the process of cholesterol capture by HDL and ApoA1 was examined by incubating the cholesterol loaded macrophages with HDL or ApoA1 together with increasing concentrations of stable PAI-1. Cholesterol in the media was quantified 15-18 hours later using the Amplex Red Cholesterol Assay kit (Invitrogen). Cells were cultured and loaded with acetylated-LDL as above and then incubated with increasing amounts of HDL or ApoA1.

These studies indicated that both ApoA1 and HDL showed a dose-dependent and saturable ability to capture cholesterol from macrophages. These studies also demonstrated that PAI-1 could inhibit the capture of cholesterol from the macrophages by either HDL or ApoA1. Taken together, these data suggest that in vivo PAI-1 may be able to regulate the process of cholesterol capture from peripheral tissues by HDL, and that in the absence of PAI-1 reverse cholesterol transport by HDL may be more efficient. Thus, the data suggest for the first time a direct link between PAI-1 and HDL metabolism.

The effects of the novel PAI-1 inactivating drugs (provided herein) are also contemplated to be examined in this cholesterol efflux assay. Likewise, the relative rates of cholesterol efflux by macrophages isolated from PAI-1 null mice and the roles of tPA, uPA, plasminogen, vitronectin, and the VLDL-receptor can be examined.

Example 28

Different Conformation Forms of PAI-1 Inhibit ApoA1-Induced Cholesterol from Lipid Loaded Macrophages To determine the effect of different forms of PAI-1 on ApoA1-induced cholesterol efflux from macrophages, experiments were carried out as set out in the previous example except for the use of increasing concentrations of various forms of PAI-1. Latent PAI-1, mutant PAI-1 (R76E), and mutant PAI-1 (141b). 141b is human PAI-1 that contains 4 amino acid substitutions that provide stabilization of the protein (Berkenpas et al, EMBO J. 14:2969-77, 1995). 141b was used in this experiment to ensure that the majority of the protein remains in its active conformation for the duration of the experiment.

Figure 12A:
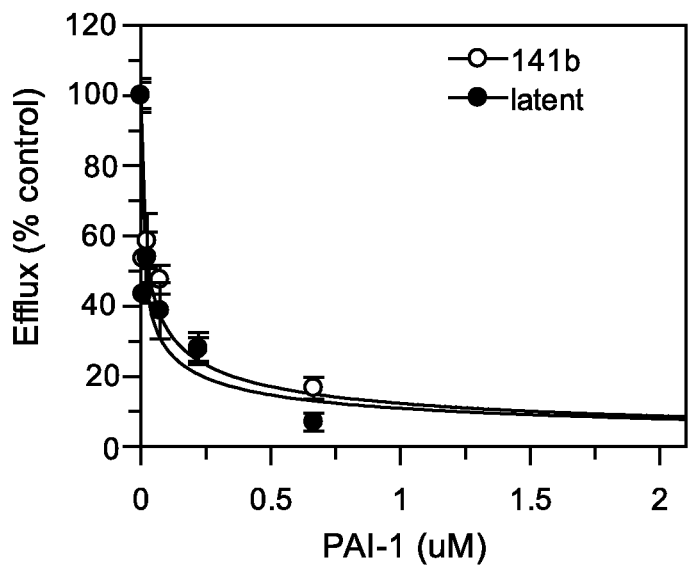
FIGS. 12A-12B show that different conformational forms of PAI-1 inhibit ApoA1 induced cholesterol efflux from lipid loaded macrophages.
Figure 12B:
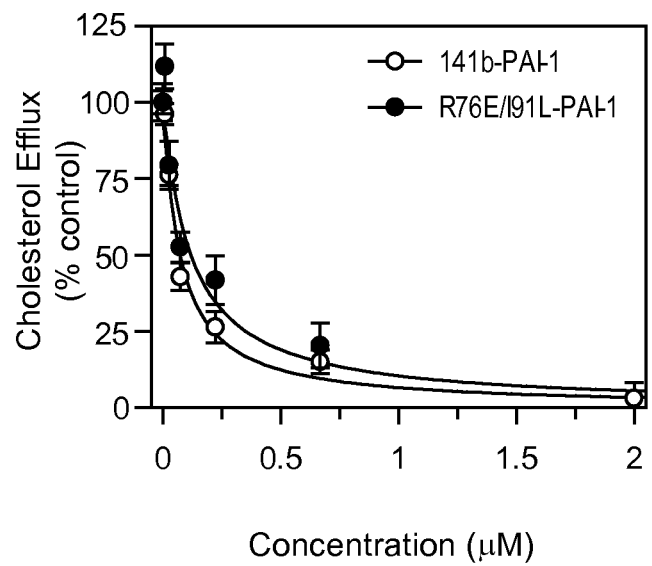

Results indicated that these different conformational forms of PAI-1 inhibited ApoA1-induced/-mediated cholesterol efflux regardless of the active or latent conformation, or of PAI-1's ability to bind LRP or other family members (FIG. 12).

Example 29

PAI-1 Binds to HDL and VLDL

Figure 15:
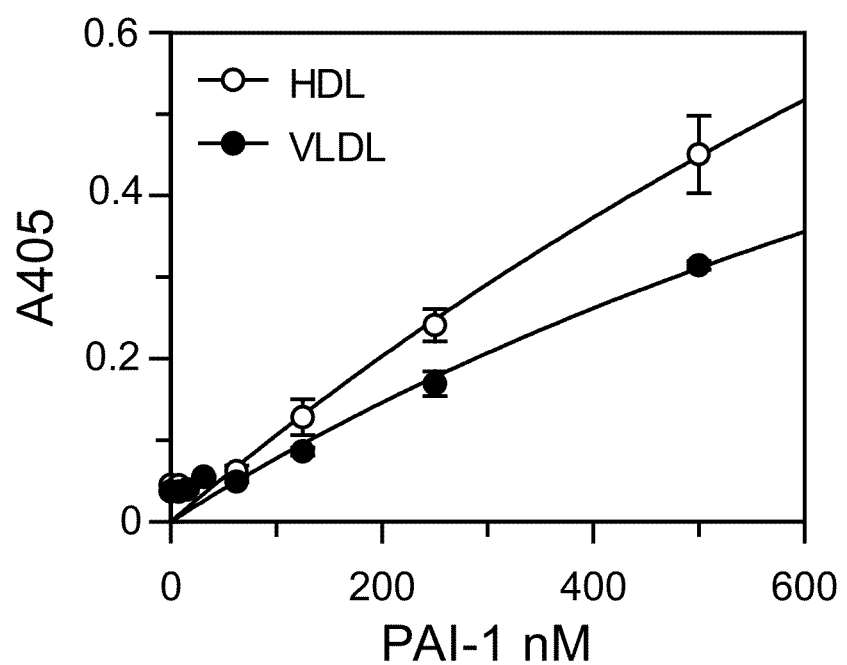
FIG. 15 demonstrates results from an ELISA showing PAI-1 binding to HDL and VLDL.

To determine if PAI-1 binds to HDL and VLDL an ELISA binding assay was carried out. Immulon 2HB microtiter plates were coated with HDL or VLDL overnight (10 mg/ml in PBS, pH 7.4) at 4° C. After blocking wells with 3% BSA in PBS, coated and control wells were incubated with blocking buffer containing increasing concentrations of PAI-1. The wells were then washed with PBS and bound PAI-1 was detected with a Rabbit-anti-Human PAI-1 antibody and a secondary anti-Rabbit antibody conjugated to HRP. Detection of the secondary antibody was performed with ABTS [2,2'-azino-bis(3-ethylbenzthiazoline-6-sulphonic acid)] using a SpectraMax M5 reading at an absorbance of 405 nm. Data clearly indicate that PAI-1 binds to HDL and VLDL (see FIG. 15).

Example 30

CDE-008 Inhibits PAI-1 in the Presence of Vitronectin and is Specific for PAI-1

Figure 9B:
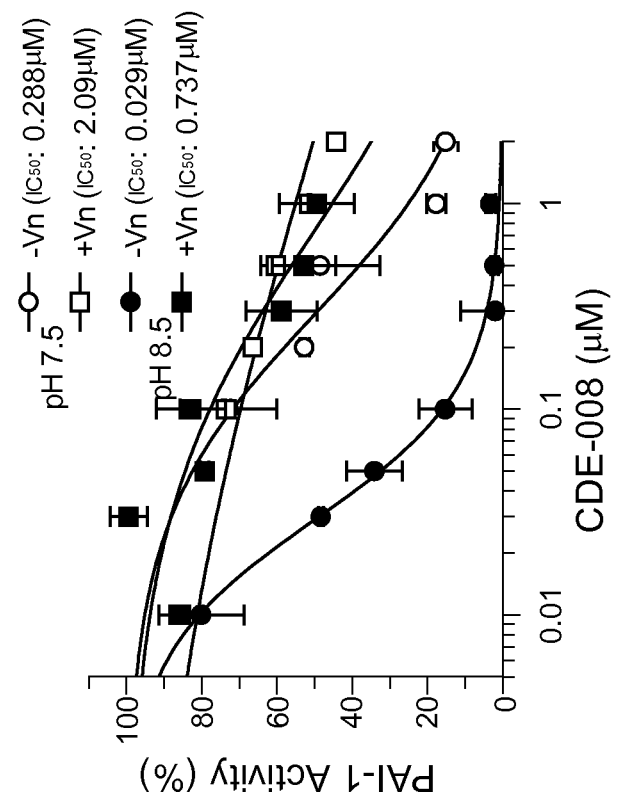
FIGS. 9A-9B show that CDE-008 inhibits PAI-1 in the presence of vitronectin at pH 7.5 and pH 8.5.
Figure 9A:
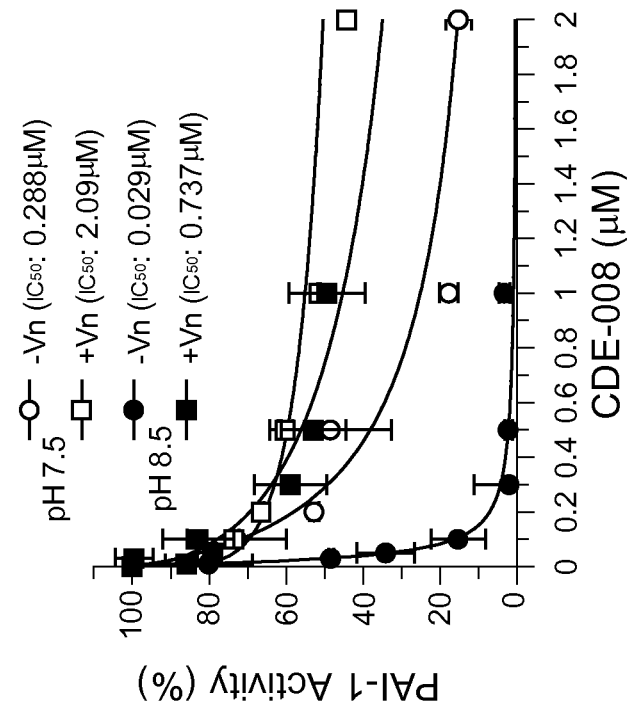

To determine if CDE-008 inhibits PAI-1 in the presence of vitronectin, the following experiment was carried out. PAI-1 (40 nM) was incubated either alone or with 200 nM vitronectin for 30 min at 23° C. 10 µL of PAI-1/vitronectin was then added to wells containing 80 µL of increasing inhibitor concentrations and incubated for 15 min at 23° C. Next 10 µL of 50 nM uPA was added to each well and incubated for 5 min at 37° C. before addition of substrate (Z-Gly-Gly-Arg-AMC, final 50 µM). The rate of AMC release by uPA was measured at an excitation wavelength of 370 nm and an emission of 440 nm for 15 min. Data were expressed as residual PAI-1 activity as a percent of control PAI-1 activity (FIG. 9). The data demonstrate that CDE-008 inhibits PAI-1 in the presence of vitronectin at both pH 7.5 and pH 8.5. There was a lesser inhibition in the presence of vitronectin at each pH, but the $IC_{50}$ was altered by only 1 log value in each case. Additionally, the data demonstrate that in the presence of vitronectin, pH did not have as great an effect as it did in the absence of vitronectin.

Figure 10:
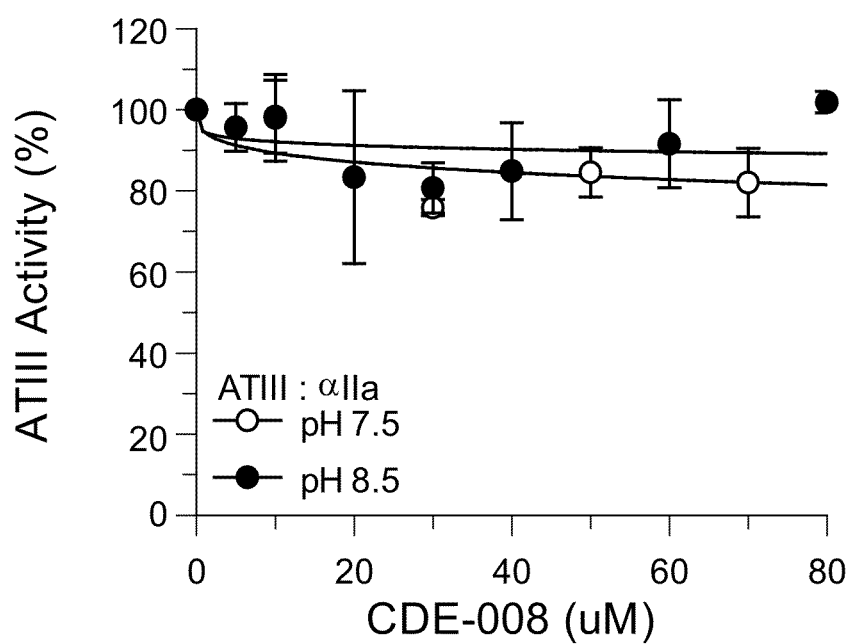
FIG. 10 shows that CDE-008 had no effect on anti-thrombin III at pH 7.5 or pH 8.5, and indicate that CDE-008 is specific for PAI-1.

To determine if CDE-008 is specific for PAI-1, an experiment was carried out to see if CDE-008 had any effect on the PAI-1-related protein, anti-thrombin III (ATIII). ATIII (final 3.2 nM) and heparin (final 3 U/mL) were incubated for 30 min at 37° C. with increasing concentrations of each compound. Human a-thrombin (final 4 nM) was added to each reaction well, and incubated for an additional 15 min at 37° C. Thrombin activity in each reaction mixture was determined with Z-Gly-Gly-Arg-AMC (Bachem) fluorgenic substrate (final 50 µM). The rate of AMC release by thrombin was measured at an excitation wavelength of 370 nm and an emission of 440 nm for 25 min. Data are expressed as residual ATIII activity as a percent of control ATIII activity. (FIG. 10). The data show that CDE-008 had no effect on ATIII at pH 7.5 or pH 8.5, and indicate that CDE-008 is specific for PAI-1.

Example 31

Inhibition of PAI-1 by CDE-008 is pH Sensitive

Figure 11:
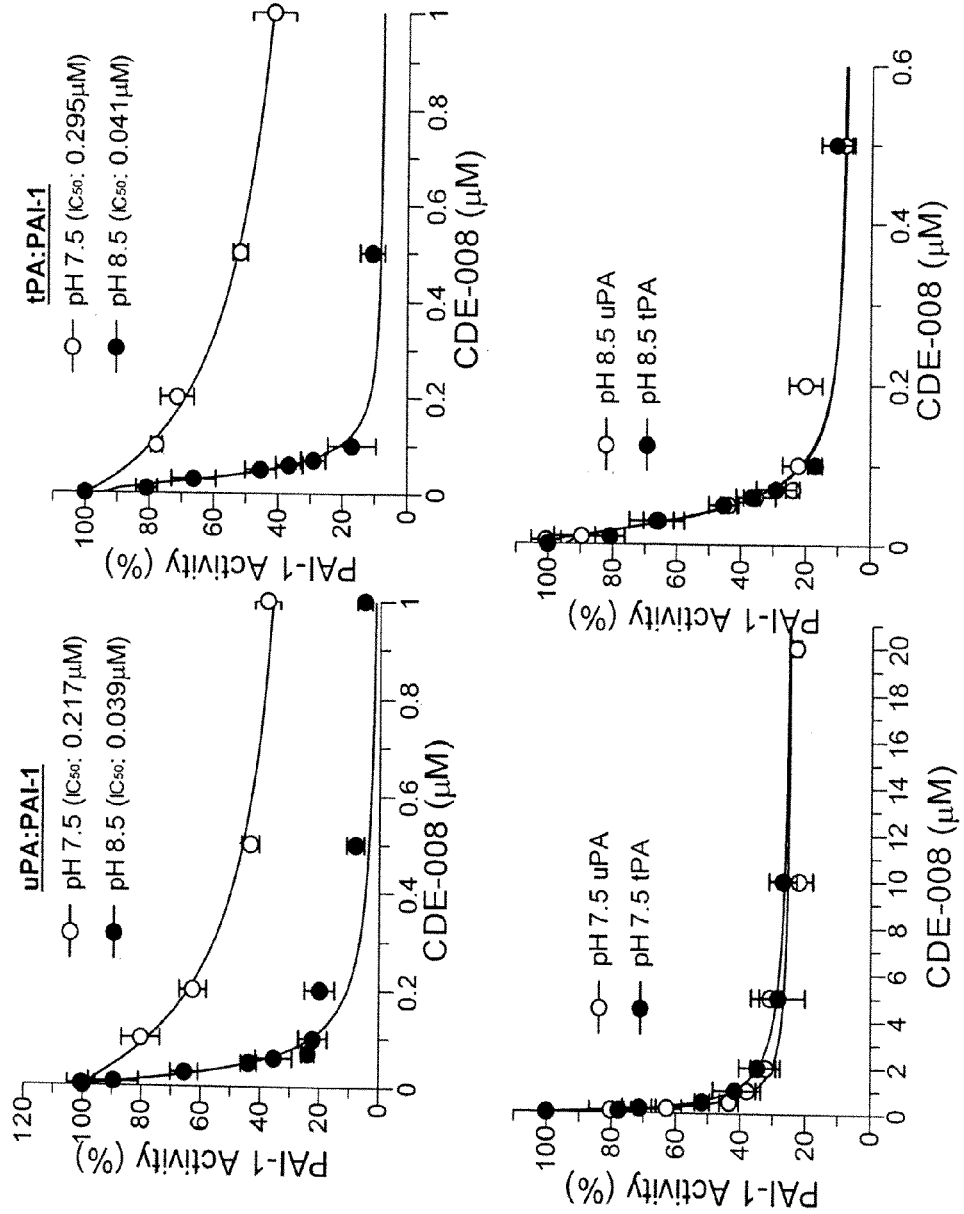
FIG. 11 shows that the inhibition of PAI-1 by CDE-008 is pH sensitive.

To determine if the inhibition of PAI-1 by CDE-008 is pH sensitive, PAI-1 activity was measured in the presence of PAI-1 in complex with uPA and tPA at pH 7.5 and pH 8.5 (FIG. 11).

Recombinant active human PAI-1 (final 3.2 nM) was incubated for 15 min at 23° C. with increasing concentrations of CDE-008. Next uPA (final 4 nM) or tPA (final 4 nM) was added to each reaction well and incubated for an additional 5 min at 37° C. PA activity in each reaction mixture was determined with Z-Gly-Gly-Arg-AMC (Bachem) fluorgenic substrate (final 50 µM). The rate of AMC release by either uPA or tPA was measured at an excitation wavelength of 370 nm and an emission of 440 nm for 15 min. Data are expressed as residual PAI-1 activity as a percent of control PAI-1 activity (FIG. 11).

The data demonstrate that the inhibition of PAI-1 by CDE-008 is pH sensitive. Moreover, the data show that CDE-008 was a more effective inhibitor at pH 8.5 than at pH 7.5.

Example 32

The Effect of PAI-1 Inhibitor Compounds in Models of Obesity and Diabetes

Genetically obese and diabetic ob/ob mice are treated with a PAI-1 inhibitor of the invention. The inhibitors are administered orally to the mice. Age- and sex-matched control groups are fed standard mouse chow (#5001, Harlan Teklad, Indianapolis, Ind.) with or without an inhibitor of the invention (5 mg inhibitor/gram of chow). All diets are formulated by the manufacturer and the concentration of drug in the diet is validated by mass spectrometry. Mice are fed for two weeks after which citrated plasma is prepared from each group and lipid profiles are determined by enzyme assays and HPLC analysis.

Plasma PAI-1 activity is expected to decrease in mice receiving an inhibitor of the invention. It is expected that HDL cholesterol increases and VLDL and/or LDL decreases in inhibitor-treated mice.

The invention has been described in terms of particular embodiments found or proposed to comprise preferred modes for the practice of the invention. It will be appreciated by those of ordinary skill in the art that, in light of the disclosure, numerous modifications and changes can be made in the particular embodiments exemplified without departing from the intended scope of the invention. Therefore, it is intended that the appended claims cover all such equivalent variations which come within the scope of the invention as claimed.

What is claimed is:

1. A compound of formula (XXII):

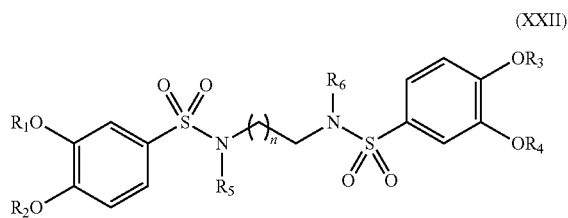

(XXII)

wherein:
n=1 to 5;
$R_1$ to $R_4$ are H; and
$R_5$ and $R_6$ are independently selected from the group consisting of H, methyl, ethyl, n-prolyl, iso-prolyl, n-butyl, iso-butyl, tert-butyl, phenyl, tolyl, benzyl.

2. The compound of claim 1 having a formula (XXIII):

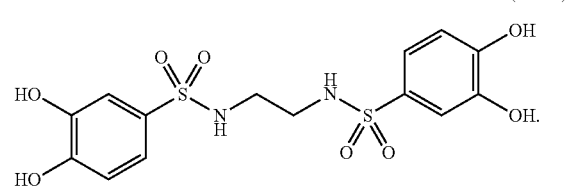

(XXIII)

3. The compound of claim 1 having a formula (XXVI):

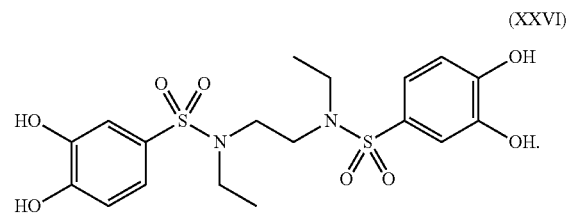 [SMILES: CCN(CCN(CC)S(=O)(=O)c1ccc(O)c(O)c1)S(=O)(=O)c1ccc(O)c(O)c1]

(XXVI)

4. A compound of formula (XXVII):

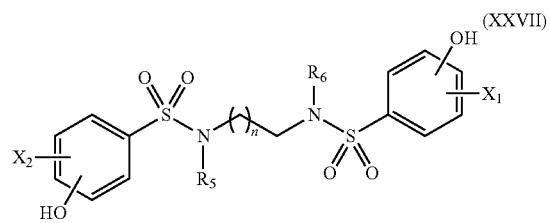

(XXVII)

wherein:
n=1 to 5;
$R_5$ to $R_6$ are independently selected from the group consisting of H, methyl, ethyl, n-propyl, iso-propyl, n-butyl, iso-butyl, tert-butyl, phenyl, tolyl, and benzyl;
$X_1$ to $X_2$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S=O, aryl, substituted aryl, and heteroaryl; and
R is $C_1$ to $C_6$ alkyl, $C_3$ to $C_6$ cycloalkyl, —CH$_2$—C$_3$-C$_6$ cycloalkyl, phenyl, tolyl, or benzyl.

5. A compound of formula (XXIX), formula (XXXIV), formula (XXXII), or formula (XXXIII):

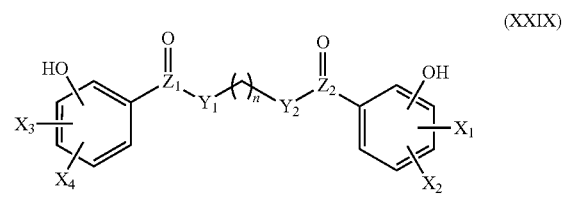

(XXIX)

wherein:
n=0 to 6;
$X_1$ to $X_4$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S=O, aryl, substituted aryl, and heteroaryl;
$Y_1$ to $Y_2$ are independently selected from the group consisting of O, NH, NR, S, and CH$_2$;
$Z_1$ to $Z_2$ are independently selected from the group consisting of C, S, and S=O; and
R is $C_1$ to $C_6$ alkyl, $C_3$ to $C_6$ cycloalkyl, CH$_2$—C$_3$-C$_6$ cycloalkyl, phenyl, tolyl, or benzyl;

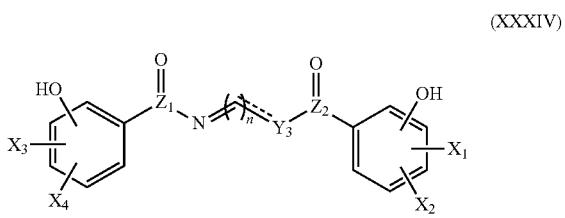

(XXXIV)

wherein:

n=0 to 5;

$X_1$ to $X_4$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S=O, aryl, substituted aryl, and heteroaryl;

$Y_3$ is O, N, NH, NR, S, and CH$_2$;

$Z_1$ to $Z_2$ are independently selected from the group consisting of C, S, and S=O;

---- is an optional double bond; and

R is $C_1$ to $C_6$ alkyl, $C_3$ to $C_6$ cycloalkyl, —CH$_2$—C$_3$-C$_6$ cycloalkyl, phenyl, tolyl, or benzyl;

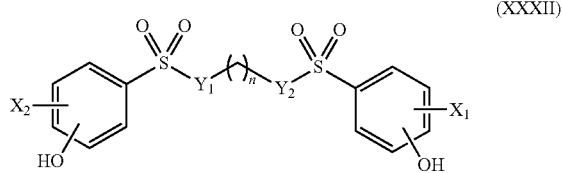

(XXXII)

wherein:

n=0 to 5;

$X_1$ to $X_2$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S=O, aryl, substituted aryl, and heteroaryl;

$Y_1$ to $Y_2$ are independently selected from the group consisting of O, NH, NR, S, and CH$_2$; and R is $C_1$ to $C_6$ alkyl, $C_3$ to $C_6$ cycloalkyl, —CH$_2$—C$_3$-C$_6$ cycloalkyl, phenyl, tolyl, or benzyl; or

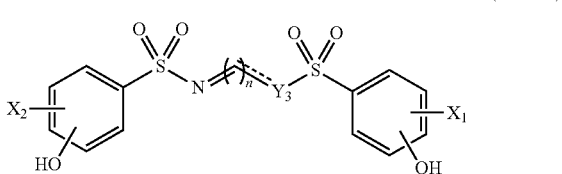

(XXXIII)

wherein:

n=0 to 5;

$X_1$ to $X_2$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S=O, aryl, substituted aryl, and heteroaryl;

$Y_3$ is O, N, NH, NR, S, and CH$_2$;

---- is an optional double bond; and

R is $C_1$ to $C_6$ alkyl, $C_3$ to $C_6$ cycloalkyl, —CH$_2$—C$_3$-C$_6$ cycloalkyl, phenyl, tolyl, or benzyl.

6. A compound of formula (XXXI):

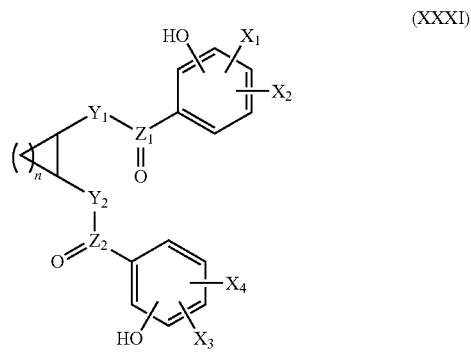

(XXXI)

wherein:

n=1 to 6;

$X_1$ to $X_4$ are independently selected from the group consisting of —OH, —F, —Cl, —Br, —NO$_2$, —NO, —NR$_3^+$, —C(O)R, —C(O)OR, —CHO, —C(O)NH$_2$, —C(O)SR, —CN, —S(O)$_2$R, —SO$_3$R, —SO$_3$H, —SO$_2$NR$_2$, —S=O, aryl, substituted aryl, and heteroaryl;

$Y_1$ to $Y_2$ are independently selected from the group consisting of O, NH, NR, S, and CH$_2$;

$Z_1$ to $Z_2$ are independently selected from the group consisting of C, S, and S=O; and R is $C_1$ to $C_6$ alkyl, $C_3$ to $C_6$ cycloalkyl, —CH$_2$—C$_3$-C$_6$ cycloalkyl, phenyl, tolyl, or benzyl.

* * * * *